US008459520B2

(12) United States Patent
Giordano et al.

(10) Patent No.: US 8,459,520 B2
(45) Date of Patent: Jun. 11, 2013

(54) SURGICAL INSTRUMENT WITH WIRELESS COMMUNICATION BETWEEN CONTROL UNIT AND REMOTE SENSOR

(75) Inventors: James R. Giordano, Milford, OH (US); Jeffrey S. Swayze, Hamilton, OH (US); Frederick E. Shelton, IV, New Vienna, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 941 days.

(21) Appl. No.: 11/651,807

(22) Filed: Jan. 10, 2007

(65) Prior Publication Data
US 2008/0167672 A1 Jul. 10, 2008

(51) Int. Cl.
*A61B 17/32* (2006.01)
(52) U.S. Cl.
USPC .......... 227/175.1; 227/180.1; 227/181.1; 227/2; 227/19; 606/219; 606/50; 606/51; 606/52; 606/45; 606/46; 606/47
(58) Field of Classification Search
USPC ....... 227/175.1, 180.1, 181.1, 2, 19; 606/219, 606/50–52, 45, 46–47, 159; 74/DIG. 7
See application file for complete search history.

(56) References Cited

U.S. PATENT DOCUMENTS

| 66,052 | A | 6/1867 | Smith |
| 662,587 | A | 11/1900 | Blake |
| 951,393 | A | 3/1910 | Hahn |
| 2,037,727 | A | 4/1936 | La Chapelle |
| 2,132,295 | A | 10/1938 | Hawkins |
| 2,161,632 | A | 6/1939 | Nattenheimer |
| 2,211,117 | A | 8/1940 | Hess |
| 2,214,870 | A | 9/1940 | West |
| 2,441,096 | A | 5/1948 | Happe |
| 2,526,902 | A | 10/1950 | Rublee |
| 2,674,149 | A | 4/1954 | Benson |
| 2,804,848 | A | 9/1957 | O'Farrell et al. |
| 2,808,482 | A | 10/1957 | Zanichkowsky et al. |
| 2,853,074 | A | 9/1958 | Olson |

(Continued)

FOREIGN PATENT DOCUMENTS

| CA | 2458946 A1 | 3/2003 |
| CA | 2512960 A1 | 1/2006 |

(Continued)

OTHER PUBLICATIONS

European Search Report, Application No. 08250080.2, dated Nov. 4, 2009 (7 pages).

(Continued)

*Primary Examiner* — Brian D Nash
*Assistant Examiner* — Michelle Lopez

(57) ABSTRACT

A surgical instrument, such as an endoscopic or laparoscopic instrument. The surgical instrument may comprise an end effector comprising at least one sensor. The surgical instrument may also comprise an electrically conductive shaft having a distal end connected to the end effector wherein the sensor is electrically insulated from the shaft. The surgical instrument may also comprise a handle connected to a proximate end of the shaft. The handle may comprise a control unit electrically coupled to the shaft such that the shaft radiates signals as an antenna from the control unit to the sensor and receives radiated signals from the sensor. Other components electrically coupled to the shaft may also radiate the signals.

21 Claims, 21 Drawing Sheets

U.S. PATENT DOCUMENTS

| | | | |
|---|---|---|---|
| 3,032,769 A | 5/1962 | Palmer | |
| 3,075,062 A | 1/1963 | Iaccarino | |
| 3,078,465 A | 2/1963 | Bobrov | |
| 3,166,072 A | 1/1965 | Sullivan, Jr. | |
| 3,266,494 A | 8/1966 | Brownrigg et al. | |
| 3,269,630 A | 8/1966 | Fleischer | |
| 3,357,296 A | 12/1967 | Lefever | |
| 3,490,675 A | 1/1970 | Green et al. | |
| 3,551,987 A | 1/1971 | Wilkinson | |
| 3,598,943 A | 8/1971 | Barrett | |
| 3,643,851 A | 2/1972 | Green et al. | |
| 3,662,939 A | 5/1972 | Bryan | |
| 3,717,294 A | 2/1973 | Green | |
| 3,734,207 A | 5/1973 | Fishbein | |
| 3,740,994 A | 6/1973 | DeCarlo, Jr. | |
| 3,744,495 A | 7/1973 | Johnson | |
| 3,746,002 A | 7/1973 | Haller | |
| 3,751,902 A | 8/1973 | Kingsbury et al. | |
| 3,819,100 A | 6/1974 | Noiles et al. | |
| 3,821,919 A | 7/1974 | Knohl | |
| 3,885,491 A | 5/1975 | Curtis | |
| 3,892,228 A | 7/1975 | Mitsui | |
| 3,894,174 A | 7/1975 | Cartun | |
| 3,940,844 A | 3/1976 | Colby et al. | |
| RE28,932 E | 8/1976 | Noiles et al. | |
| 4,060,089 A | 11/1977 | Noiles | |
| 4,129,059 A | 12/1978 | Van Eck | |
| 4,213,562 A | 7/1980 | Garrett et al. | |
| 4,250,436 A | 2/1981 | Weissman | |
| 4,261,244 A | 4/1981 | Becht et al. | |
| 4,272,662 A | 6/1981 | Simpson | |
| 4,275,813 A | 6/1981 | Noiles | |
| 4,289,133 A | 9/1981 | Rothfuss | |
| 4,305,539 A | 12/1981 | Korolkov et al. | |
| 4,317,451 A | 3/1982 | Cerwin et al. | |
| 4,321,002 A | 3/1982 | Froehlich | |
| 4,331,277 A | 5/1982 | Green | |
| 4,340,331 A | 7/1982 | Savino | |
| 4,347,450 A | 8/1982 | Colligan | |
| 4,349,028 A | 9/1982 | Green | |
| 4,353,371 A * | 10/1982 | Cosman | 606/42 |
| 4,379,457 A | 4/1983 | Gravener et al. | |
| 4,380,312 A | 4/1983 | Landrus | |
| 4,383,634 A | 5/1983 | Green | |
| 4,396,139 A | 8/1983 | Hall et al. | |
| 4,402,445 A | 9/1983 | Green | |
| 4,408,692 A | 10/1983 | Siegel et al. | |
| 4,415,112 A | 11/1983 | Green | |
| 4,428,376 A | 1/1984 | Mericle | |
| 4,429,695 A | 2/1984 | Green | |
| 4,434,796 A | 3/1984 | Karapetian et al. | |
| 4,442,964 A | 4/1984 | Becht | |
| 4,451,743 A | 5/1984 | Suzuki et al. | |
| 4,454,887 A | 6/1984 | Krüger | |
| 4,467,805 A | 8/1984 | Fukuda | |
| 4,475,679 A | 10/1984 | Fleury, Jr. | |
| 4,485,816 A | 12/1984 | Krumme | |
| 4,489,875 A | 12/1984 | Crawford et al. | |
| 4,500,024 A | 2/1985 | DiGiovanni et al. | |
| 4,505,273 A | 3/1985 | Braun et al. | |
| 4,505,414 A | 3/1985 | Filipi | |
| 4,506,671 A | 3/1985 | Green | |
| 4,520,817 A | 6/1985 | Green | |
| 4,522,327 A | 6/1985 | Korthoff et al. | |
| 4,526,174 A | 7/1985 | Froehlich | |
| 4,527,724 A | 7/1985 | Chow et al. | |
| 4,530,453 A | 7/1985 | Green | |
| 4,548,202 A | 10/1985 | Duncan | |
| 4,565,189 A | 1/1986 | Mabuchi | |
| 4,566,620 A | 1/1986 | Green et al. | |
| 4,573,469 A | 3/1986 | Golden et al. | |
| 4,573,622 A | 3/1986 | Green et al. | |
| 4,576,167 A | 3/1986 | Noiles et al. | |
| 4,580,712 A | 4/1986 | Green | |
| 4,589,416 A | 5/1986 | Green | |
| 4,591,085 A | 5/1986 | Di Giovanni | |
| 4,604,786 A | 8/1986 | Howie, Jr. | |
| 4,605,001 A | 8/1986 | Rothfuss et al. | |
| 4,606,343 A | 8/1986 | Conta et al. | |
| 4,607,638 A | 8/1986 | Crainich | |
| 4,608,981 A | 9/1986 | Rothfuss et al. | |
| 4,610,250 A | 9/1986 | Green | |
| 4,610,383 A | 9/1986 | Rothfuss et al. | |
| 4,619,262 A | 10/1986 | Taylor | |
| 4,629,107 A | 12/1986 | Fedotov et al. | |
| 4,632,290 A | 12/1986 | Green et al. | |
| 4,633,874 A | 1/1987 | Chow et al. | |
| 4,641,076 A | 2/1987 | Linden | |
| 4,646,722 A | 3/1987 | Silverstein et al. | |
| 4,655,222 A | 4/1987 | Florez et al. | |
| 4,663,874 A | 5/1987 | Sano et al. | |
| 4,664,305 A | 5/1987 | Blake, III et al. | |
| 4,665,916 A | 5/1987 | Green | |
| 4,667,674 A | 5/1987 | Korthoff et al. | |
| 4,671,445 A | 6/1987 | Barker et al. | |
| 4,676,245 A | 6/1987 | Fukuda | |
| 4,693,248 A | 9/1987 | Failla | |
| 4,709,120 A | 11/1987 | Pearson | |
| 4,715,520 A | 12/1987 | Roehr, Jr. et al. | |
| 4,719,917 A | 1/1988 | Barrows et al. | |
| 4,728,020 A | 3/1988 | Green et al. | |
| 4,728,876 A | 3/1988 | Mongeon et al. | |
| 4,729,260 A | 3/1988 | Dudden | |
| 4,741,336 A | 5/1988 | Failla et al. | |
| 4,752,024 A | 6/1988 | Green et al. | |
| 4,754,909 A | 7/1988 | Barker et al. | |
| 4,767,044 A | 8/1988 | Green | |
| 4,777,780 A | 10/1988 | Holzwarth | |
| 4,787,387 A | 11/1988 | Burbank, III et al. | |
| 4,790,225 A | 12/1988 | Moody et al. | |
| 4,805,617 A | 2/1989 | Bedi et al. | |
| 4,805,823 A | 2/1989 | Rothfuss | |
| 4,809,695 A | 3/1989 | Gwathmey et al. | |
| 4,817,847 A | 4/1989 | Redtenbacher et al. | |
| 4,819,853 A | 4/1989 | Green | |
| 4,821,939 A | 4/1989 | Green | |
| 4,827,911 A | 5/1989 | Broadwin et al. | |
| 4,844,068 A | 7/1989 | Arata et al. | |
| 4,869,414 A | 9/1989 | Green et al. | |
| 4,869,415 A | 9/1989 | Fox | |
| 4,880,015 A | 11/1989 | Nierman | |
| 4,890,613 A | 1/1990 | Golden et al. | |
| 4,892,244 A | 1/1990 | Fox et al. | |
| 4,915,100 A | 4/1990 | Green | |
| 4,930,503 A | 6/1990 | Pruitt | |
| 4,932,960 A | 6/1990 | Green et al. | |
| 4,938,408 A | 7/1990 | Bedi et al. | |
| 4,941,623 A | 7/1990 | Pruitt | |
| 4,944,443 A | 7/1990 | Oddsen et al. | |
| 4,955,959 A | 9/1990 | Tompkins et al. | |
| 4,978,049 A | 12/1990 | Green | |
| 4,986,808 A | 1/1991 | Broadwin et al. | |
| 4,988,334 A | 1/1991 | Hornlein et al. | |
| 5,002,553 A | 3/1991 | Shiber | |
| 5,009,661 A | 4/1991 | Michelson | |
| 5,014,899 A | 5/1991 | Presty et al. | |
| 5,015,227 A | 5/1991 | Broadwin et al. | |
| 5,027,834 A | 7/1991 | Pruitt | |
| 5,031,814 A | 7/1991 | Tompkins et al. | |
| 5,040,715 A | 8/1991 | Green et al. | |
| 5,042,707 A | 8/1991 | Taheri | |
| 5,061,269 A | 10/1991 | Muller | |
| 5,062,563 A | 11/1991 | Green et al. | |
| 5,065,929 A | 11/1991 | Schulze et al. | |
| 5,071,052 A | 12/1991 | Rodak et al. | |
| 5,071,430 A | 12/1991 | de Salis et al. | |
| 5,074,454 A | 12/1991 | Peters | |
| 5,080,556 A | 1/1992 | Carreno | |
| 5,083,695 A | 1/1992 | Foslien et al. | |
| 5,084,057 A | 1/1992 | Green et al. | |
| 5,088,979 A | 2/1992 | Filipi et al. | |
| 5,088,997 A | 2/1992 | Delahuerga et al. | |
| 5,094,247 A | 3/1992 | Hernandez et al. | |
| 5,100,420 A | 3/1992 | Green et al. | |
| 5,104,025 A | 4/1992 | Main et al. | |
| 5,106,008 A | 4/1992 | Tompkins et al. | |
| 5,111,987 A | 5/1992 | Moeinzadeh et al. | |

| | | | | | | |
|---|---|---|---|---|---|---|
| 5,116,349 A | 5/1992 | Aranyi | 5,359,231 A | 10/1994 | Flowers et al. | |
| 5,129,570 A | 7/1992 | Schulze et al. | D352,780 S | 11/1994 | Glaeser et al. | |
| 5,137,198 A | 8/1992 | Nobis et al. | 5,360,428 A | 11/1994 | Hutchinson, Jr. | |
| 5,139,513 A | 8/1992 | Segato | 5,364,003 A | 11/1994 | Williamson, IV | |
| 5,141,144 A | 8/1992 | Foslien et al. | 5,366,134 A | 11/1994 | Green et al. | |
| 5,156,315 A | 10/1992 | Green et al. | 5,366,479 A | 11/1994 | McGarry et al. | |
| 5,156,614 A | 10/1992 | Green et al. | 5,368,015 A * | 11/1994 | Wilk | 600/104 |
| 5,158,567 A | 10/1992 | Green | 5,370,645 A | 12/1994 | Klicek et al. | |
| D330,699 S | 11/1992 | Gill | 5,372,596 A | 12/1994 | Klicek et al. | |
| 5,163,598 A | 11/1992 | Peters et al. | 5,372,602 A | 12/1994 | Burke | |
| 5,171,247 A | 12/1992 | Hughett et al. | 5,374,277 A | 12/1994 | Hassler | |
| 5,171,249 A | 12/1992 | Stefanchik et al. | 5,379,933 A | 1/1995 | Green et al. | |
| 5,188,111 A | 2/1993 | Yates et al. | 5,381,782 A | 1/1995 | DeLaRama et al. | |
| 5,190,517 A | 3/1993 | Zieve et al. | 5,382,247 A | 1/1995 | Cimino et al. | |
| 5,195,968 A | 3/1993 | Lundquist et al. | 5,383,880 A | 1/1995 | Hooven | |
| 5,197,648 A | 3/1993 | Gingold | 5,383,881 A | 1/1995 | Green et al. | |
| 5,200,280 A | 4/1993 | Karasa | 5,383,888 A | 1/1995 | Zvenyatsky et al. | |
| 5,205,459 A | 4/1993 | Brinkerhoff et al. | 5,383,895 A | 1/1995 | Holmes et al. | |
| 5,207,697 A | 5/1993 | Carusillo et al. | 5,389,098 A | 2/1995 | Tsuruta et al. | |
| 5,209,747 A | 5/1993 | Knoepfler | 5,391,180 A | 2/1995 | Tovey et al. | |
| 5,211,649 A | 5/1993 | Kohler et al. | 5,392,979 A | 2/1995 | Green et al. | |
| 5,217,457 A | 6/1993 | Delahuerga et al. | 5,395,030 A | 3/1995 | Kuramoto et al. | |
| 5,217,478 A | 6/1993 | Rexroth | 5,395,033 A | 3/1995 | Byrne et al. | |
| 5,219,111 A | 6/1993 | Bilotti et al. | 5,395,312 A | 3/1995 | Desai | |
| 5,221,036 A | 6/1993 | Takase | 5,397,046 A | 3/1995 | Savage et al. | |
| 5,221,281 A | 6/1993 | Klicek | 5,397,324 A | 3/1995 | Carroll et al. | |
| 5,222,963 A | 6/1993 | Brinkerhoff et al. | 5,403,312 A | 4/1995 | Yates et al. | |
| 5,222,975 A | 6/1993 | Crainich | 5,405,072 A | 4/1995 | Zlock et al. | |
| 5,222,976 A | 6/1993 | Yoon | 5,405,344 A | 4/1995 | Williamson et al. | |
| 5,223,675 A | 6/1993 | Taft | 5,407,293 A | 4/1995 | Crainich | |
| 5,234,447 A | 8/1993 | Kaster et al. | 5,409,498 A | 4/1995 | Braddock et al. | |
| 5,236,440 A | 8/1993 | Hlavacek | 5,411,508 A | 5/1995 | Bessler et al. | |
| 5,239,981 A | 8/1993 | Anapliotis | 5,413,267 A | 5/1995 | Solyntjes et al. | |
| 5,240,163 A | 8/1993 | Stein et al. | 5,413,268 A | 5/1995 | Green et al. | |
| 5,242,457 A | 9/1993 | Akopov et al. | 5,413,272 A | 5/1995 | Green et al. | |
| 5,244,462 A | 9/1993 | Delahuerga et al. | 5,415,334 A | 5/1995 | Williamson, IV et al. | |
| 5,246,156 A | 9/1993 | Rothfuss et al. | 5,415,335 A | 5/1995 | Knodell, Jr. | |
| 5,246,443 A | 9/1993 | Mai | 5,417,361 A | 5/1995 | Williamson, IV | |
| 5,253,793 A | 10/1993 | Green et al. | 5,421,829 A | 6/1995 | Olichney et al. | |
| 5,258,009 A | 11/1993 | Conners | 5,422,567 A | 6/1995 | Matsunaga | |
| 5,258,012 A | 11/1993 | Luscombe et al. | 5,423,809 A | 6/1995 | Klicek | |
| 5,259,366 A | 11/1993 | Reydel et al. | 5,425,745 A | 6/1995 | Green et al. | |
| 5,260,637 A | 11/1993 | Pizzi | 5,431,322 A | 7/1995 | Green et al. | |
| 5,263,629 A | 11/1993 | Trumbull et al. | 5,431,668 A | 7/1995 | Burbank, III et al. | |
| 5,263,973 A | 11/1993 | Cook | 5,433,721 A | 7/1995 | Hooven et al. | |
| 5,268,622 A | 12/1993 | Philipp | 5,438,302 A | 8/1995 | Goble | |
| 5,271,543 A | 12/1993 | Grant et al. | 5,439,479 A | 8/1995 | Shichman et al. | |
| 5,271,544 A | 12/1993 | Fox et al. | 5,441,193 A | 8/1995 | Gravener | |
| RE34,519 E | 1/1994 | Fox et al. | 5,441,494 A | 8/1995 | Ortiz | |
| 5,275,323 A | 1/1994 | Schulze et al. | 5,445,304 A | 8/1995 | Plyley et al. | |
| 5,275,608 A | 1/1994 | Forman et al. | 5,445,644 A | 8/1995 | Pietrafitta et al. | |
| 5,281,216 A | 1/1994 | Klicek | 5,447,417 A | 9/1995 | Kuhl et al. | |
| 5,282,806 A | 2/1994 | Haber et al. | 5,447,513 A | 9/1995 | Davison et al. | |
| 5,282,829 A | 2/1994 | Hermes | 5,449,355 A | 9/1995 | Rhum et al. | |
| 5,297,714 A | 3/1994 | Kramer | 5,449,365 A | 9/1995 | Green et al. | |
| 5,304,204 A | 4/1994 | Bregen | 5,452,836 A | 9/1995 | Huitema et al. | |
| 5,307,976 A | 5/1994 | Olson et al. | 5,452,837 A | 9/1995 | Williamson, IV et al. | |
| 5,309,927 A | 5/1994 | Welch | 5,454,827 A | 10/1995 | Aust et al. | |
| 5,312,023 A | 5/1994 | Green et al. | 5,456,401 A | 10/1995 | Green et al. | |
| 5,312,329 A | 5/1994 | Beaty et al. | 5,458,579 A | 10/1995 | Chodorow et al. | |
| 5,314,424 A | 5/1994 | Nicholas | 5,462,215 A | 10/1995 | Viola et al. | |
| 5,318,221 A | 6/1994 | Green et al. | 5,464,300 A | 11/1995 | Crainich | |
| 5,330,502 A | 7/1994 | Hassler et al. | 5,465,894 A | 11/1995 | Clark et al. | |
| 5,332,142 A | 7/1994 | Robinson et al. | 5,465,895 A | 11/1995 | Knodel et al. | |
| 5,333,422 A | 8/1994 | Warren et al. | 5,465,896 A | 11/1995 | Allen et al. | |
| 5,334,183 A | 8/1994 | Wuchinich | 5,466,020 A | 11/1995 | Page et al. | |
| 5,336,232 A | 8/1994 | Green et al. | 5,467,911 A | 11/1995 | Tsuruta et al. | |
| 5,339,799 A | 8/1994 | Kami et al. | 5,470,006 A | 11/1995 | Rodak | |
| 5,341,724 A | 8/1994 | Vatel | 5,470,007 A | 11/1995 | Plyley et al. | |
| 5,341,810 A | 8/1994 | Dardel | 5,472,132 A | 12/1995 | Savage et al. | |
| 5,342,395 A | 8/1994 | Jarrett et al. | 5,472,442 A | 12/1995 | Klicek | |
| 5,342,396 A | 8/1994 | Cook | 5,473,204 A | 12/1995 | Temple | |
| 5,344,060 A | 9/1994 | Gravener et al. | 5,474,057 A | 12/1995 | Makower et al. | |
| 5,350,400 A | 9/1994 | Esposito et al. | 5,474,566 A | 12/1995 | Alesi et al. | |
| 5,352,235 A | 10/1994 | Koros et al. | 5,476,206 A | 12/1995 | Green et al. | |
| 5,352,238 A | 10/1994 | Green et al. | 5,476,479 A | 12/1995 | Green et al. | |
| 5,354,303 A | 10/1994 | Spaeth et al. | 5,478,003 A | 12/1995 | Green et al. | |
| 5,356,006 A | 10/1994 | Alpern et al. | 5,478,354 A | 12/1995 | Tovey et al. | |
| 5,358,510 A | 10/1994 | Luscombe et al. | 5,480,089 A | 1/1996 | Blewett | |

| Patent No. | Kind | Date | Inventor |
|---|---|---|---|
| 5,480,409 | A | 1/1996 | Riza |
| 5,482,197 | A | 1/1996 | Green et al. |
| 5,484,095 | A | 1/1996 | Green et al. |
| 5,484,398 | A | 1/1996 | Stoddard |
| 5,484,451 | A | 1/1996 | Akopov et al. |
| 5,485,947 | A | 1/1996 | Olson et al. |
| 5,485,952 | A | 1/1996 | Fontayne |
| 5,487,499 | A | 1/1996 | Sorrentino et al. |
| 5,487,500 | A | 1/1996 | Knodel et al. |
| 5,489,058 | A | 2/1996 | Plyley et al. |
| 5,489,256 | A | 2/1996 | Adair |
| 5,496,312 | A | 3/1996 | Klicek |
| 5,496,317 | A | 3/1996 | Goble et al. |
| 5,497,933 | A | 3/1996 | DeFonzo et al. |
| 5,503,320 | A | 4/1996 | Webster et al. |
| 5,503,635 | A | 4/1996 | Sauer et al. |
| 5,503,638 | A | 4/1996 | Cooper et al. |
| 5,505,363 | A | 4/1996 | Green et al. |
| 5,507,426 | A | 4/1996 | Young et al. |
| 5,509,596 | A | 4/1996 | Green et al. |
| 5,509,916 | A | 4/1996 | Taylor |
| 5,511,564 | A | 4/1996 | Wilk |
| 5,514,129 | A | 5/1996 | Smith |
| 5,514,157 | A | 5/1996 | Nicholas et al. |
| 5,518,163 | A | 5/1996 | Hooven |
| 5,518,164 | A | 5/1996 | Hooven |
| 5,520,678 | A | 5/1996 | Heckele et al. |
| 5,520,700 | A | 5/1996 | Beyar et al. |
| 5,522,817 | A | 6/1996 | Sander et al. |
| 5,527,320 | A | 6/1996 | Carruthers et al. |
| 5,529,235 | A | 6/1996 | Boiarski et al. |
| D372,086 | S | 7/1996 | Grasso et al. |
| 5,531,744 | A | 7/1996 | Nardella et al. |
| 5,533,521 | A | 7/1996 | Granger |
| 5,533,581 | A | 7/1996 | Barth et al. |
| 5,533,661 | A | 7/1996 | Main et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,541,376 | A | 7/1996 | Ladtkow et al. |
| 5,542,594 | A | 8/1996 | McKean et al. |
| 5,543,119 | A | 8/1996 | Sutter et al. |
| 5,547,117 | A | 8/1996 | Hamblin et al. |
| 5,549,621 | A | 8/1996 | Bessler et al. |
| 5,549,628 | A | 8/1996 | Cooper et al. |
| 5,549,637 | A | 8/1996 | Crainich |
| 5,553,675 | A | 9/1996 | Pitzen et al. |
| 5,553,765 | A | 9/1996 | Knodel et al. |
| 5,554,169 | A | 9/1996 | Green et al. |
| 5,556,416 | A | 9/1996 | Clark et al. |
| 5,558,665 | A | 9/1996 | Kieturakis |
| 5,558,671 | A | 9/1996 | Yates |
| 5,560,530 | A | 10/1996 | Bolanos et al. |
| 5,560,532 | A | 10/1996 | DeFonzo et al. |
| 5,562,239 | A * | 10/1996 | Boiarski et al. ............ 227/175.2 |
| 5,562,241 | A | 10/1996 | Knodel et al. |
| 5,562,682 | A | 10/1996 | Oberlin et al. |
| 5,562,701 | A | 10/1996 | Huitema et al. |
| 5,562,702 | A | 10/1996 | Huitema et al. |
| 5,564,615 | A | 10/1996 | Bishop et al. |
| 5,569,161 | A | 10/1996 | Ebling et al. |
| 5,571,090 | A | 11/1996 | Sherts |
| 5,571,100 | A | 11/1996 | Goble et al. |
| 5,571,116 | A | 11/1996 | Bolanos et al. |
| 5,573,543 | A | 11/1996 | Akopov et al. |
| 5,574,431 | A | 11/1996 | McKeown et al. |
| 5,575,789 | A | 11/1996 | Bell et al. |
| 5,575,799 | A | 11/1996 | Bolanos et al. |
| 5,575,803 | A | 11/1996 | Cooper et al. |
| 5,577,654 | A | 11/1996 | Bishop |
| 5,579,978 | A | 12/1996 | Green et al. |
| 5,580,067 | A | 12/1996 | Hamblin et al. |
| 5,582,611 | A | 12/1996 | Tsuruta et al. |
| 5,582,617 | A | 12/1996 | Klieman et al. |
| 5,584,425 | A | 12/1996 | Savage et al. |
| 5,586,711 | A | 12/1996 | Plyley et al. |
| 5,588,579 | A | 12/1996 | Schnut et al. |
| 5,588,580 | A | 12/1996 | Paul et al. |
| 5,588,581 | A | 12/1996 | Conlon et al. |
| 5,591,170 | A | 1/1997 | Spievack et al. |
| 5,591,187 | A | 1/1997 | Dekel |
| 5,597,107 | A | 1/1997 | Knodel et al. |
| 5,599,151 | A | 2/1997 | Daum et al. |
| 5,599,344 | A | 2/1997 | Paterson |
| 5,599,350 | A | 2/1997 | Schulze et al. |
| 5,601,224 | A | 2/1997 | Bishop et al. |
| 5,603,443 | A | 2/1997 | Clark et al. |
| 5,605,272 | A | 2/1997 | Witt et al. |
| 5,605,273 | A | 2/1997 | Hamblin et al. |
| 5,607,094 | A | 3/1997 | Clark et al. |
| 5,607,095 | A | 3/1997 | Smith et al. |
| 5,607,450 | A | 3/1997 | Zvenyatsky et al. |
| 5,609,285 | A | 3/1997 | Grant et al. |
| 5,611,709 | A | 3/1997 | McAnulty |
| 5,613,966 | A | 3/1997 | Makower et al. |
| 5,618,294 | A | 4/1997 | Aust et al. |
| 5,618,303 | A | 4/1997 | Marlow et al. |
| 5,620,289 | A | 4/1997 | Curry |
| 5,620,452 | A | 4/1997 | Yoon |
| 5,624,452 | A | 4/1997 | Yates |
| 5,626,587 | A | 5/1997 | Bishop et al. |
| 5,628,446 | A | 5/1997 | Geiste et al. |
| 5,628,743 | A | 5/1997 | Cimino |
| 5,630,539 | A | 5/1997 | Plyley et al. |
| 5,630,540 | A | 5/1997 | Blewett |
| 5,630,782 | A | 5/1997 | Adair |
| 5,632,432 | A | 5/1997 | Schulze et al. |
| 5,632,433 | A | 5/1997 | Grant et al. |
| 5,634,584 | A | 6/1997 | Okorocha et al. |
| 5,636,779 | A | 6/1997 | Palmer |
| 5,636,780 | A | 6/1997 | Green et al. |
| 5,639,008 | A | 6/1997 | Gallagher et al. |
| 5,643,291 | A | 7/1997 | Pier et al. |
| 5,645,209 | A | 7/1997 | Green et al. |
| 5,647,526 | A | 7/1997 | Green et al. |
| 5,647,869 | A | 7/1997 | Goble et al. |
| 5,649,937 | A | 7/1997 | Bito et al. |
| 5,651,491 | A | 7/1997 | Heaton et al. |
| 5,653,373 | A | 8/1997 | Green et al. |
| 5,653,374 | A | 8/1997 | Young et al. |
| 5,653,677 | A | 8/1997 | Okada et al. |
| 5,653,721 | A | 8/1997 | Knodel et al. |
| 5,655,698 | A | 8/1997 | Yoon |
| 5,657,921 | A | 8/1997 | Young et al. |
| 5,658,281 | A | 8/1997 | Heard |
| 5,658,300 | A | 8/1997 | Bito et al. |
| 5,662,258 | A | 9/1997 | Knodel et al. |
| 5,662,260 | A | 9/1997 | Yoon |
| 5,662,662 | A | 9/1997 | Bishop et al. |
| 5,667,517 | A | 9/1997 | Hooven |
| 5,667,526 | A | 9/1997 | Levin |
| 5,667,527 | A | 9/1997 | Cook |
| 5,669,544 | A | 9/1997 | Schulze et al. |
| 5,669,904 | A | 9/1997 | Platt, Jr. et al. |
| 5,669,907 | A | 9/1997 | Platt, Jr. et al. |
| 5,669,918 | A | 9/1997 | Balazs et al. |
| 5,673,840 | A | 10/1997 | Schulze et al. |
| 5,673,841 | A | 10/1997 | Schulze et al. |
| 5,673,842 | A | 10/1997 | Bittner et al. |
| 5,678,748 | A | 10/1997 | Plyley et al. |
| 5,680,981 | A | 10/1997 | Mililli et al. |
| 5,680,982 | A | 10/1997 | Schulze et al. |
| 5,680,983 | A | 10/1997 | Plyley et al. |
| 5,683,349 | A | 11/1997 | Makower et al. |
| 5,685,474 | A | 11/1997 | Seeber |
| 5,688,270 | A | 11/1997 | Yates et al. |
| 5,690,269 | A | 11/1997 | Bolanos et al. |
| 5,692,668 | A | 12/1997 | Schulze et al. |
| 5,693,042 | A | 12/1997 | Boiarski et al. |
| 5,693,051 | A | 12/1997 | Schulze et al. |
| 5,695,494 | A | 12/1997 | Becker |
| 5,695,504 | A | 12/1997 | Gifford, III et al. |
| 5,695,524 | A | 12/1997 | Kelley et al. |
| 5,697,543 | A | 12/1997 | Burdorff |
| 5,697,943 | A | 12/1997 | Sauer et al. |
| 5,700,270 | A | 12/1997 | Peyser et al. |
| 5,702,387 | A | 12/1997 | Arts et al. |

| | | |
|---|---|---|
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,121 A | 3/1998 | Bimbo et al. |
| 5,730,758 A | 3/1998 | Allgeyer |
| 5,732,871 A | 3/1998 | Clark et al. |
| 5,732,872 A | 3/1998 | Bolduc et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,807,378 A | 9/1998 | Jensen et al. |
| 5,807,393 A | 9/1998 | Williamson, IV et al. |
| 5,809,441 A | 9/1998 | McKee |
| 5,810,811 A | 9/1998 | Yates et al. |
| 5,810,855 A | 9/1998 | Rayburn et al. |
| 5,813,813 A | 9/1998 | Daum et al. |
| 5,814,057 A | 9/1998 | Oi et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,827,271 A | 10/1998 | Buysse et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,132 A | 12/1998 | Ilvento |
| 5,846,254 A | 12/1998 | Schulze et al. |
| 5,849,011 A | 12/1998 | Jones et al. |
| 5,855,311 A | 1/1999 | Hamblin et al. |
| 5,855,583 A | 1/1999 | Wang et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,894,979 A | 4/1999 | Powell |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,693 A | 5/1999 | Dicesare et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,948,030 A | 9/1999 | Miller et al. |
| 5,951,552 A | 9/1999 | Long et al. |
| 5,951,574 A | 9/1999 | Stefanchik et al. |
| 5,954,259 A | 9/1999 | Viola et al. |
| 5,964,774 A | 10/1999 | McKean et al. |
| 5,971,916 A | 10/1999 | Koren |
| 5,988,479 A | 11/1999 | Palmer |
| 6,003,517 A | 12/1999 | Sheffield et al. |
| 6,004,319 A | 12/1999 | Goble et al. |
| 6,010,054 A | 1/2000 | Johnson et al. |
| 6,012,494 A | 1/2000 | Balazs |
| 6,013,076 A | 1/2000 | Goble et al. |
| 6,015,406 A | 1/2000 | Goble et al. |
| 6,017,322 A | 1/2000 | Snoke et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,039,733 A | 3/2000 | Buysse et al. |
| 6,039,734 A * | 3/2000 | Goble .................. 606/41 |
| 6,045,560 A | 4/2000 | McKean et al. |
| 6,050,472 A | 4/2000 | Shibata |
| 6,053,390 A | 4/2000 | Green et al. |
| 6,056,746 A | 5/2000 | Goble et al. |

| | | | |
|---|---|---|---|
| 6,063,097 A | 5/2000 | Oi et al. |
| 6,063,098 A | 5/2000 | Houser et al. |
| 6,068,627 A | 5/2000 | Orszulak et al. |
| 6,071,233 A | 6/2000 | Ishikawa et al. |
| 6,074,386 A | 6/2000 | Goble et al. |
| 6,077,286 A | 6/2000 | Cuschieri et al. |
| 6,079,606 A | 6/2000 | Milliman et al. |
| 6,082,577 A | 7/2000 | Coates et al. |
| 6,083,234 A | 7/2000 | Nicholas et al. |
| 6,083,242 A | 7/2000 | Cook |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,109,500 A | 8/2000 | Alli et al. |
| 6,117,158 A | 9/2000 | Measamer et al. |
| 6,119,913 A | 9/2000 | Adams et al. |
| 6,120,433 A | 9/2000 | Mizuno et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,132,368 A | 10/2000 | Cooper |
| 6,139,546 A | 10/2000 | Koenig et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,162,208 A | 12/2000 | Hipps |
| 6,165,175 A | 12/2000 | Wampler et al. |
| 6,165,184 A | 12/2000 | Verdura et al. |
| 6,168,605 B1 | 1/2001 | Measamer et al. |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,179,776 B1 | 1/2001 | Adams et al. |
| 6,181,105 B1 | 1/2001 | Cutolo et al. |
| 6,193,129 B1 | 2/2001 | Bittner et al. |
| 6,197,042 B1 | 3/2001 | Ginn et al. |
| 6,202,914 B1 | 3/2001 | Geiste et al. |
| 6,214,028 B1 | 4/2001 | Yoon et al. |
| 6,220,368 B1 | 4/2001 | Ark et al. |
| 6,223,835 B1 | 5/2001 | Habedank et al. |
| 6,228,081 B1 | 5/2001 | Goble |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,723 B1 | 6/2001 | Heim et al. |
| 6,249,076 B1 | 6/2001 | Madden et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,306,134 B1 | 10/2001 | Goble et al. |
| 6,309,403 B1 | 10/2001 | Minor et al. |
| 6,315,184 B1 | 11/2001 | Whitman |
| 6,320,123 B1 | 11/2001 | Reimers |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,334,860 B1 | 1/2002 | Dorn |
| 6,336,926 B1 | 1/2002 | Goble |
| 6,346,077 B1 | 2/2002 | Taylor et al. |
| 6,352,503 B1 | 3/2002 | Matsui et al. |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,373,152 B1 | 4/2002 | Wang et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,398,781 B1 | 6/2002 | Goble et al. |
| 6,398,797 B2 | 6/2002 | Bombard et al. |
| 6,406,440 B1 | 6/2002 | Stefanchik |
| 6,409,724 B1 | 6/2002 | Penny et al. |
| H2037 H | 7/2002 | Yates et al. |
| 6,416,486 B1 | 7/2002 | Wampler |
| 6,416,509 B1 | 7/2002 | Goble et al. |
| 6,419,695 B1 | 7/2002 | Gabbay |
| RE37,814 E | 8/2002 | Allgeyer |
| 6,436,097 B1 | 8/2002 | Nardella |
| 6,436,107 B1 | 8/2002 | Wang et al. |
| 6,436,122 B1 | 8/2002 | Frank et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,450,391 B1 | 9/2002 | Kayan et al. |
| 6,468,275 B1 | 10/2002 | Wampler et al. |
| 6,471,106 B1 | 10/2002 | Reining |
| 6,482,200 B2 | 11/2002 | Shippert |
| 6,485,490 B2 | 11/2002 | Wampler et al. |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,543,456 B1 | 4/2003 | Freeman |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,558,379 B1 | 5/2003 | Batchelor et al. |
| 6,565,560 B1 | 5/2003 | Goble et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,588,643 B2 | 7/2003 | Bolduc et al. |
| 6,589,164 B1 | 7/2003 | Flaherty |
| 6,592,597 B2 | 7/2003 | Grant et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,605,078 B2 | 8/2003 | Adams |
| 6,605,669 B2 | 8/2003 | Awokola et al. |
| 6,616,686 B2 | 9/2003 | Coleman et al. |
| 6,619,529 B2 | 9/2003 | Green et al. |
| 6,620,166 B2 | 9/2003 | Wenstrom, Jr. et al. |
| 6,629,630 B2 | 10/2003 | Adams |
| 6,629,974 B2 | 10/2003 | Penny et al. |
| 6,629,988 B2 | 10/2003 | Weadock |
| 6,636,412 B2 | 10/2003 | Smith |
| 6,638,108 B2 | 10/2003 | Tachi |
| 6,638,285 B2 | 10/2003 | Gabbay |
| 6,641,528 B2 | 11/2003 | Torii |
| 6,644,532 B2 | 11/2003 | Green et al. |
| 6,648,816 B2 | 11/2003 | Irion et al. |
| D484,243 S | 12/2003 | Ryan et al. |
| D484,595 S | 12/2003 | Ryan et al. |
| D484,596 S | 12/2003 | Ryan et al. |

| | | |
|---|---|---|
| 6,656,193 B2 | 12/2003 | Grant et al. |
| 6,666,875 B1 | 12/2003 | Sakurai et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,692,507 B2 | 2/2004 | Pugsley et al. |
| 6,695,199 B2 | 2/2004 | Whitman |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,767,352 B2 | 7/2004 | Field et al. |
| 6,767,356 B2 | 7/2004 | Kanner et al. |
| 6,769,594 B2 | 8/2004 | Orban, III |
| 6,773,438 B1 | 8/2004 | Knodel et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,790,173 B2 | 9/2004 | Saadat et al. |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,821,273 B2 | 11/2004 | Mollenauer |
| 6,821,284 B2 | 11/2004 | Sturtz et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,832,998 B2 | 12/2004 | Goble |
| 6,834,001 B2 | 12/2004 | Myono |
| 6,835,199 B2 | 12/2004 | McGuckin, Jr. et al. |
| 6,843,403 B2 | 1/2005 | Whitman |
| 6,843,789 B2 | 1/2005 | Goble |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,866,178 B2 | 3/2005 | Adams et al. |
| 6,866,671 B2 | 3/2005 | Tierney et al. |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,905,057 B2 | 6/2005 | Swayze et al. |
| 6,905,497 B2 | 6/2005 | Truckai et al. |
| 6,913,608 B2 | 7/2005 | Liddicoat et al. |
| 6,913,613 B2 | 7/2005 | Schwarz et al. |
| 6,923,803 B2 | 8/2005 | Goble |
| 6,929,641 B2 | 8/2005 | Goble et al. |
| 6,931,830 B2 | 8/2005 | Liao |
| 6,936,042 B2 | 8/2005 | Wallace et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,851 B2 | 11/2005 | Heinrich |
| 6,959,852 B2 | 11/2005 | Shelton, IV et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,972,199 B2 * | 12/2005 | Lebouitz et al. .................. 438/5 |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,052,494 B2 | 5/2006 | Goble et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,508 B2 | 6/2006 | Shelton, IV et al. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,070,083 B2 | 7/2006 | Jankowski |
| 7,070,559 B2 | 7/2006 | Adams et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,684 B2 | 8/2006 | McGuckin, Jr. et al. |
| 7,094,202 B2 | 8/2006 | Nobis et al. |
| 7,097,089 B2 | 8/2006 | Marczyk |
| 7,098,794 B2 | 8/2006 | Lindsay et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |

| | | |
|---|---|---|
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 * | 1/2007 | Sonnenschein et al. ...... 606/219 |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,179,223 B2 | 2/2007 | Motoki et al. |
| 7,179,267 B2 | 2/2007 | Nolan et al. |
| 7,182,239 B1 | 2/2007 | Myers |
| 7,188,758 B2 | 3/2007 | Viola et al. |
| 7,195,627 B2 | 3/2007 | Amoah et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,213,736 B2 | 5/2007 | Wales et al. |
| 7,214,224 B2 | 5/2007 | Goble |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,258,262 B2 | 8/2007 | Mastri et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,994 B2 | 10/2007 | Goble |
| 7,282,048 B2 | 10/2007 | Goble et al. |
| 7,295,907 B2 | 11/2007 | Lu et al. |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,556 B2 | 12/2007 | Metzger |
| 7,308,998 B2 | 12/2007 | Mastri et al. |
| 7,324,572 B2 | 1/2008 | Chang |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,334,717 B2 | 2/2008 | Rethy et al. |
| 7,336,184 B2 | 2/2008 | Smith et al. |
| 7,338,513 B2 | 3/2008 | Lee et al. |
| 7,343,920 B2 | 3/2008 | Toby et al. |
| 7,348,763 B1 | 3/2008 | Reinhart et al. |
| 7,351,258 B2 | 4/2008 | Ricotta et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,388,217 B2 | 6/2008 | Buschbeck et al. |
| 7,396,356 B2 | 7/2008 | Mollenauer |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,418,078 B2 | 8/2008 | Blanz et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,455,208 B2 | 11/2008 | Wales et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,473,253 B2 | 1/2009 | Dycus et al. |
| 7,479,608 B2 | 1/2009 | Smith |
| 7,481,347 B2 | 1/2009 | Roy |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,501,198 B2 | 3/2009 | Barlev et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,524,320 B2 | 4/2009 | Tierney et al. |
| 7,530,985 B2 | 5/2009 | Takemoto et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,563,862 B2 | 7/2009 | Sieg et al. |
| 7,566,300 B2 | 7/2009 | Devierre et al. |

| Patent/Pub No. | Kind | Date | Inventor(s) |
|---|---|---|---|
| 7,568,603 | B2 | 8/2009 | Shelton, IV et al. |
| 7,568,604 | B2 | 8/2009 | Ehrenfels et al. |
| 7,575,144 | B2 | 8/2009 | Ortiz et al. |
| 7,588,175 | B2 | 9/2009 | Timm et al. |
| 7,588,176 | B2 | 9/2009 | Timm et al. |
| 7,597,229 | B2 | 10/2009 | Boudreaux et al. |
| 7,600,663 | B2 | 10/2009 | Green |
| 7,604,150 | B2 | 10/2009 | Boudreaux |
| 7,604,151 | B2 | 10/2009 | Hess et al. |
| 7,607,557 | B2 | 10/2009 | Shelton, IV et al. |
| 7,611,038 | B2 | 11/2009 | Racenet et al. |
| 7,615,003 | B2 | 11/2009 | Stefanchik et al. |
| 7,624,902 | B2 | 12/2009 | Marczyk et al. |
| 7,631,793 | B2 | 12/2009 | Rethy et al. |
| 7,637,409 | B2 | 12/2009 | Marczyk |
| 7,641,092 | B2 | 1/2010 | Kruszynski et al. |
| 7,641,093 | B2 | 1/2010 | Doll et al. |
| 7,644,848 | B2 | 1/2010 | Swayze et al. |
| 7,651,498 | B2 | 1/2010 | Shifrin et al. |
| 7,656,131 | B2 | 2/2010 | Embrey et al. |
| 7,658,312 | B2 | 2/2010 | Vidal et al. |
| 7,665,646 | B2 | 2/2010 | Prommersberger |
| 7,674,255 | B2 | 3/2010 | Braun |
| 7,682,307 | B2 | 3/2010 | Danitz et al. |
| 7,686,826 | B2 | 3/2010 | Lee et al. |
| 7,691,098 | B2 | 4/2010 | Wallace et al. |
| 7,699,204 | B2 | 4/2010 | Viola |
| 7,699,859 | B2 | 4/2010 | Bombard et al. |
| 7,708,180 | B2 | 5/2010 | Murray et al. |
| 7,708,758 | B2 | 5/2010 | Lee et al. |
| 7,714,239 | B2 | 5/2010 | Smith |
| 7,721,930 | B2 | 5/2010 | McKenna et al. |
| 7,722,610 | B2 | 5/2010 | Viola et al. |
| 7,726,537 | B2 | 6/2010 | Olson et al. |
| 7,726,538 | B2 | 6/2010 | Holsten et al. |
| 7,743,960 | B2 | 6/2010 | Whitman et al. |
| 7,744,627 | B2 | 6/2010 | Orban, III et al. |
| 7,766,821 | B2 | 8/2010 | Brunnen et al. |
| 7,766,894 | B2 | 8/2010 | Weitzner et al. |
| 7,771,396 | B2 | 8/2010 | Stefanchik et al. |
| 7,772,720 | B2 | 8/2010 | McGee et al. |
| 7,776,060 | B2 | 8/2010 | Mooradian et al. |
| 7,780,054 | B2 | 8/2010 | Wales |
| 7,780,055 | B2 | 8/2010 | Scirica et al. |
| 7,780,663 | B2 | 8/2010 | Yates et al. |
| 7,780,685 | B2 | 8/2010 | Hunt et al. |
| 7,784,662 | B2 | 8/2010 | Wales et al. |
| 7,803,151 | B2 | 9/2010 | Whitman |
| 7,806,891 | B2 | 10/2010 | Nowlin et al. |
| 7,815,565 | B2 | 10/2010 | Stefanchik et al. |
| 7,824,401 | B2 | 11/2010 | Manzo et al. |
| 7,828,794 | B2 | 11/2010 | Sartor |
| 7,828,808 | B2 | 11/2010 | Hinman et al. |
| 7,832,611 | B2 | 11/2010 | Boyden et al. |
| 7,836,400 | B2 | 11/2010 | May et al. |
| 7,837,081 | B2 | 11/2010 | Holsten et al. |
| 7,845,533 | B2 | 12/2010 | Marczyk et al. |
| 7,845,534 | B2 | 12/2010 | Viola et al. |
| 7,846,149 | B2 | 12/2010 | Jankowski |
| 7,870,989 | B2 | 1/2011 | Viola et al. |
| 7,887,530 | B2 | 2/2011 | Zemlok et al. |
| 7,905,380 | B2 | 3/2011 | Shelton, IV et al. |
| 7,905,381 | B2 | 3/2011 | Baxter, III et al. |
| 7,909,191 | B2 | 3/2011 | Baker et al. |
| 7,909,221 | B2 | 3/2011 | Viola et al. |
| 7,913,891 | B2 | 3/2011 | Doll et al. |
| 7,914,543 | B2 | 3/2011 | Roth et al. |
| 7,918,377 | B2 | 4/2011 | Measamer et al. |
| 7,922,061 | B2 | 4/2011 | Shelton, IV et al. |
| 7,922,063 | B2 | 4/2011 | Zemlok et al. |
| 7,934,630 | B2 | 5/2011 | Shelton, IV et al. |
| 7,938,307 | B2 | 5/2011 | Bettuchi |
| 7,942,303 | B2 | 5/2011 | Shah |
| 7,942,890 | B2 | 5/2011 | D'Agostino et al. |
| 7,950,560 | B2 | 5/2011 | Zemlok et al. |
| 7,954,682 | B2 | 6/2011 | Giordano et al. |
| 7,954,684 | B2 | 6/2011 | Boudreaux |
| 7,954,686 | B2 | 6/2011 | Baxter, III et al. |
| 7,959,050 | B2 | 6/2011 | Smith et al. |
| 7,963,963 | B2 | 6/2011 | Francischelli et al. |
| 7,967,180 | B2 | 6/2011 | Scirica |
| 7,972,298 | B2 | 7/2011 | Wallace et al. |
| 8,002,795 | B2 | 8/2011 | Beetel |
| 8,011,551 | B2 | 9/2011 | Marczyk et al. |
| 8,011,555 | B2 | 9/2011 | Tarinelli et al. |
| 8,028,883 | B2 | 10/2011 | Stopek |
| 8,034,077 | B2 | 10/2011 | Smith et al. |
| 8,038,045 | B2 | 10/2011 | Bettuchi et al. |
| 8,038,046 | B2 | 10/2011 | Smith et al. |
| 8,062,330 | B2 | 11/2011 | Prommersberger et al. |
| D650,074 | S | 12/2011 | Hunt et al. |
| 8,091,756 | B2 | 1/2012 | Viola |
| 8,097,017 | B2 | 1/2012 | Viola |
| 8,108,072 | B2 | 1/2012 | Zhao et al. |
| 8,123,103 | B2 | 2/2012 | Milliman |
| 8,152,041 | B2 | 4/2012 | Kostrzewski |
| 8,157,152 | B2 | 4/2012 | Holsten et al. |
| 8,167,895 | B2 | 5/2012 | D'Agostino et al. |
| 8,211,125 | B2 | 7/2012 | Spivey |
| 8,220,468 | B2 | 7/2012 | Cooper et al. |
| 8,225,799 | B2 | 7/2012 | Bettuchi |
| 8,241,271 | B2 | 8/2012 | Millman et al. |
| 8,245,898 | B2 | 8/2012 | Smith et al. |
| 8,245,901 | B2 | 8/2012 | Stopek |
| 8,256,654 | B2 | 9/2012 | Bettuchi et al. |
| 8,257,391 | B2 | 9/2012 | Orban, III et al. |
| 2002/0022836 | A1 | 2/2002 | Goble et al. |
| 2002/0029036 | A1 | 3/2002 | Goble et al. |
| 2002/0117534 | A1 | 8/2002 | Green et al. |
| 2002/0134811 | A1 | 9/2002 | Napier et al. |
| 2002/0165541 | A1 | 11/2002 | Whitman |
| 2003/0093103 | A1 | 5/2003 | Malackowski et al. |
| 2003/0105478 | A1 | 6/2003 | Whitman et al. |
| 2003/0130677 | A1 | 7/2003 | Whitman et al. |
| 2003/0139741 | A1 | 7/2003 | Goble et al. |
| 2003/0153908 | A1 | 8/2003 | Goble et al. |
| 2003/0195387 | A1 | 10/2003 | Kortenbach et al. |
| 2003/0205029 | A1 | 11/2003 | Chapolini et al. |
| 2003/0216732 | A1 | 11/2003 | Truckai et al. |
| 2003/0220660 | A1 | 11/2003 | Kortenbach et al. |
| 2004/0002726 | A1 | 1/2004 | Nunez et al. |
| 2004/0006335 | A1 | 1/2004 | Garrison |
| 2004/0006340 | A1 | 1/2004 | Latterell et al. |
| 2004/0006372 | A1 | 1/2004 | Racenet et al. |
| 2004/0030333 | A1 | 2/2004 | Goble |
| 2004/0034357 | A1 | 2/2004 | Beane et al. |
| 2004/0034369 | A1 | 2/2004 | Sauer et al. |
| 2004/0044364 | A1 | 3/2004 | DeVries et al. |
| 2004/0068161 | A1 | 4/2004 | Couvillon, Jr. |
| 2004/0068307 | A1 | 4/2004 | Goble |
| 2004/0078037 | A1 | 4/2004 | Batchelor et al. |
| 2004/0093024 | A1 | 5/2004 | Lousararian et al. |
| 2004/0094597 | A1 | 5/2004 | Whitman et al. |
| 2004/0097987 | A1 | 5/2004 | Pugsley et al. |
| 2004/0101822 | A1 | 5/2004 | Weisner et al. |
| 2004/0108357 | A1 | 6/2004 | Milliman et al. |
| 2004/0111081 | A1 | 6/2004 | Whitman et al. |
| 2004/0115022 | A1 | 6/2004 | Albertson et al. |
| 2004/0116952 | A1 | 6/2004 | Sakurai et al. |
| 2004/0147909 | A1 | 7/2004 | Johnston et al. |
| 2004/0164123 | A1 | 8/2004 | Racenet et al. |
| 2004/0167572 | A1 | 8/2004 | Roth et al. |
| 2004/0173659 | A1 | 9/2004 | Green et al. |
| 2004/0181219 | A1 | 9/2004 | Goble et al. |
| 2004/0186470 | A1 | 9/2004 | Goble et al. |
| 2004/0193189 | A1 | 9/2004 | Kortenbach et al. |
| 2004/0222268 | A1 | 11/2004 | Bilotti et al. |
| 2004/0230214 | A1 | 11/2004 | Donofrio et al. |
| 2004/0232201 | A1 | 11/2004 | Wenchell et al. |
| 2004/0243151 | A1 | 12/2004 | Demmy et al. |
| 2004/0243163 | A1 | 12/2004 | Casiano et al. |
| 2004/0243176 | A1 | 12/2004 | Hahnen et al. |
| 2004/0254566 | A1 | 12/2004 | Plicchi et al. |
| 2004/0254608 | A1 | 12/2004 | Huitema et al. |
| 2004/0267310 | A1 | 12/2004 | Racenet et al. |
| 2005/0032511 | A1 | 2/2005 | Malone et al. |
| 2005/0033357 | A1 | 2/2005 | Braun |
| 2005/0054946 | A1 | 3/2005 | Krzyzanowski |

| Publication No. | Date | Inventor |
|---|---|---|
| 2005/0059997 A1 | 3/2005 | Bauman et al. |
| 2005/0070929 A1 | 3/2005 | Dalessandro et al. |
| 2005/0080454 A1 | 4/2005 | Drews et al. |
| 2005/0085693 A1 | 4/2005 | Belson et al. |
| 2005/0090817 A1 | 4/2005 | Phan |
| 2005/0099290 A1* | 5/2005 | Govari ............... 340/539.13 |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0145675 A1 | 7/2005 | Hartwick et al. |
| 2005/0154258 A1 | 7/2005 | Tartaglia et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0184121 A1 | 8/2005 | Heinrich |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0274768 A1 | 12/2005 | Cummins et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0100643 A1 | 5/2006 | Laufer et al. |
| 2006/0108393 A1 | 5/2006 | Heinrich et al. |
| 2006/0111710 A1 | 5/2006 | Goble et al. |
| 2006/0111711 A1 | 5/2006 | Goble |
| 2006/0111723 A1 | 5/2006 | Chapolini et al. |
| 2006/0122636 A1 | 6/2006 | Bailly et al. |
| 2006/0129140 A1* | 6/2006 | Todd et al. ............... 606/1 |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0173470 A1 | 8/2006 | Oray et al. |
| 2006/0180634 A1 | 8/2006 | Shelton, IV et al. |
| 2006/0183246 A1 | 8/2006 | Wiesner et al. |
| 2006/0200123 A1 | 9/2006 | Ryan |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0245971 A1 | 11/2006 | Burns et al. |
| 2006/0258904 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0273135 A1 | 12/2006 | Beetel |
| 2006/0278680 A1 | 12/2006 | Viola et al. |
| 2006/0278681 A1 | 12/2006 | Viola et al. |
| 2006/0289602 A1 | 12/2006 | Wales et al. |
| 2006/0291981 A1 | 12/2006 | Viola et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |
| 2007/0034668 A1 | 2/2007 | Holsten et al. |
| 2007/0045379 A1 | 3/2007 | Shelton, IV |
| 2007/0055219 A1 | 3/2007 | Whitman et al. |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0083193 A1 | 4/2007 | Werneth et al. |
| 2007/0084897 A1 | 4/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106113 A1 | 5/2007 | Ravo |
| 2007/0106317 A1 | 5/2007 | Shelton, IV et al. |
| 2007/0114261 A1 | 5/2007 | Ortiz et al. |
| 2007/0118175 A1 | 5/2007 | Butler et al. |
| 2007/0129605 A1 | 6/2007 | Schaaf |
| 2007/0135803 A1 | 6/2007 | Belson |
| 2007/0158358 A1 | 7/2007 | Mason, II et al. |
| 2007/0158385 A1 | 7/2007 | Hueil et al. |
| 2007/0170225 A1 | 7/2007 | Shelton, IV et al. |
| 2007/0173806 A1* | 7/2007 | Orszulak et al. ............... 606/34 |
| 2007/0173813 A1* | 7/2007 | Odom ............... 606/51 |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175957 A1 | 8/2007 | Shelton, IV et al. |
| 2007/0175958 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0203510 A1 | 8/2007 | Bettuchi |
| 2007/0213750 A1 | 9/2007 | Weadock |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0233053 A1 | 10/2007 | Shelton, IV et al. |
| 2007/0239028 A1 | 10/2007 | Houser et al. |
| 2007/0246505 A1 | 10/2007 | Pace-Floridia et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0288044 A1 | 12/2007 | Jinno et al. |
| 2007/0295780 A1 | 12/2007 | Shelton et al. |
| 2007/0299427 A1 | 12/2007 | Yeung et al. |

| Publication No. | Date | Inventor |
|---|---|---|
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082114 A1 | 4/2008 | McKenna et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0114385 A1 | 5/2008 | Byrum et al. |
| 2008/0129253 A1 | 6/2008 | Shiue et al. |
| 2008/0140115 A1 | 6/2008 | Stopek |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0185419 A1 | 8/2008 | Smith et al. |
| 2008/0197167 A1 | 8/2008 | Viola et al. |
| 2008/0200835 A1 | 8/2008 | Monson et al. |
| 2008/0210738 A1 | 9/2008 | Shelton et al. |
| 2008/0228029 A1 | 9/2008 | Mikkaichi et al. |
| 2008/0237296 A1 | 10/2008 | Boudreaux et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0262654 A1 | 10/2008 | Omori et al. |
| 2008/0283570 A1 | 11/2008 | Boyden et al. |
| 2008/0287944 A1 | 11/2008 | Pearson et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314954 A1 | 12/2008 | Boudreaux |
| 2008/0314955 A1 | 12/2008 | Boudreaux et al. |
| 2008/0314957 A1 | 12/2008 | Boudreaux |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001128 A1 | 1/2009 | Weisenburgh, II et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012534 A1 | 1/2009 | Madhani et al. |
| 2009/0012556 A1 | 1/2009 | Boudreaux et al. |
| 2009/0020958 A1 | 1/2009 | Soul |
| 2009/0054908 A1* | 2/2009 | Zand et al. .................. 606/130 |
| 2009/0057369 A1 | 3/2009 | Smith et al. |
| 2009/0076534 A1 | 3/2009 | Shelton, IV et al. |
| 2009/0090763 A1 | 4/2009 | Zemlok et al. |
| 2009/0093728 A1 | 4/2009 | Hyde et al. |
| 2009/0108048 A1 | 4/2009 | Zemlok et al. |
| 2009/0114701 A1 | 5/2009 | Zemlok et al. |
| 2009/0143805 A1 | 6/2009 | Palmer et al. |
| 2009/0149871 A9 | 6/2009 | Kagan et al. |
| 2009/0157067 A1* | 6/2009 | Kane et al. .................. 606/33 |
| 2009/0200355 A1 | 8/2009 | Baxter, III et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206135 A1 | 8/2009 | Hall et al. |
| 2009/0206136 A1 | 8/2009 | Moore et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0213685 A1 | 8/2009 | Mak et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0289096 A1 | 11/2009 | Shelton, IV et al. |
| 2009/0292283 A1* | 11/2009 | Odom .................. 606/51 |
| 2009/0308907 A1 | 12/2009 | Nalagatla et al. |
| 2010/0001036 A1 | 1/2010 | Marczyk et al. |
| 2010/0012704 A1 | 1/2010 | Tarinelli Racenet et al. |
| 2010/0023024 A1 | 1/2010 | Zeiner et al. |
| 2010/0032470 A1 | 2/2010 | Hess et al. |
| 2010/0049084 A1 | 2/2010 | Nock et al. |
| 2010/0065605 A1 | 3/2010 | Shelton, IV et al. |
| 2010/0065609 A1 | 3/2010 | Schwemberger |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072254 A1 | 3/2010 | Aranyi et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0096431 A1 | 4/2010 | Smith et al. |
| 2010/0096435 A1 | 4/2010 | Fuchs et al. |
| 2010/0108740 A1 | 5/2010 | Pastorelli et al. |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0145146 A1 | 6/2010 | Melder |
| 2010/0163598 A1 | 7/2010 | Belzer |
| 2010/0179382 A1 | 7/2010 | Shelton, IV et al. |

| | | | | | | |
|---|---|---|---|---|---|---|
| 2010/0181364 A1 | 7/2010 | Shelton, IV et al. | | 2011/0233258 A1 | 9/2011 | Boudreaux |
| 2010/0186219 A1 | 7/2010 | Smith | | 2011/0253766 A1 | 10/2011 | Baxter, III et al. |
| 2010/0193566 A1 | 8/2010 | Scheib et al. | | 2011/0275901 A1 | 11/2011 | Shelton, IV |
| 2010/0193567 A1 | 8/2010 | Scheib et al. | | 2011/0276083 A1 | 11/2011 | Shelton, IV et al. |
| 2010/0193568 A1 | 8/2010 | Scheib et al. | | 2011/0288573 A1 | 11/2011 | Yates et al. |
| 2010/0193569 A1 | 8/2010 | Yates et al. | | 2011/0290851 A1 | 12/2011 | Shelton, IV |
| 2010/0198220 A1 | 8/2010 | Boudreaux et al. | | 2011/0290853 A1 | 12/2011 | Shelton, IV et al. |
| 2010/0200637 A1 | 8/2010 | Beetel | | 2011/0290854 A1 | 12/2011 | Timm et al. |
| 2010/0213241 A1 | 8/2010 | Bedi et al. | | 2011/0290855 A1 | 12/2011 | Moore et al. |
| 2010/0222901 A1 | 9/2010 | Swayze et al. | | 2011/0290856 A1 | 12/2011 | Shelton, IV et al. |
| 2010/0224669 A1 | 9/2010 | Shelton, IV et al. | | 2011/0290857 A1 | 12/2011 | Shelton, IV et al. |
| 2010/0230465 A1 | 9/2010 | Smith et al. | | 2011/0295242 A1 | 12/2011 | Spivey et al. |
| 2010/0237132 A1 | 9/2010 | Measamer et al. | | 2011/0295269 A1 | 12/2011 | Swensgard et al. |
| 2010/0243707 A1 | 9/2010 | Olson et al. | | 2011/0295270 A1 | 12/2011 | Giordano et al. |
| 2010/0243708 A1 | 9/2010 | Aranyi et al. | | 2011/0295295 A1 | 12/2011 | Shelton, IV et al. |
| 2010/0243709 A1 | 9/2010 | Hess et al. | | 2012/0022523 A1 | 1/2012 | Smith et al. |
| 2010/0258611 A1 | 10/2010 | Smith et al. | | 2012/0024934 A1 | 2/2012 | Shelton, IV et al. |
| 2010/0264193 A1 | 10/2010 | Huang et al. | | 2012/0024935 A1 | 2/2012 | Shelton, IV et al. |
| 2010/0264194 A1 | 10/2010 | Huang et al. | | 2012/0024936 A1 | 2/2012 | Baxter, III et al. |
| 2010/0276471 A1 | 11/2010 | Whitman | | 2012/0029272 A1 | 2/2012 | Shelton, IV et al. |
| 2010/0294827 A1 | 11/2010 | Boyden et al. | | 2012/0029544 A1 | 2/2012 | Shelton, IV et al. |
| 2010/0294829 A1 | 11/2010 | Giordano et al. | | 2012/0029547 A1 | 2/2012 | Shelton, IV et al. |
| 2010/0301095 A1 | 12/2010 | Shelton, IV et al. | | 2012/0046692 A1 | 2/2012 | Smith et al. |
| 2010/0301096 A1 | 12/2010 | Moore et al. | | 2012/0061448 A1 | 3/2012 | Zingman |
| 2010/0305552 A1 | 12/2010 | Shelton, IV et al. | | 2012/0071711 A1 | 3/2012 | Shelton, IV et al. |
| 2010/0308100 A1 | 12/2010 | Boudreaux | | 2012/0071866 A1 | 3/2012 | Kerr et al. |
| 2010/0312261 A1 | 12/2010 | Suzuki et al. | | 2012/0074196 A1 | 3/2012 | Shelton, IV et al. |
| 2011/0006099 A1 | 1/2011 | Hall et al. | | 2012/0074198 A1 | 3/2012 | Huitema et al. |
| 2011/0006101 A1 | 1/2011 | Hall et al. | | 2012/0074200 A1 | 3/2012 | Schmid et al. |
| 2011/0006103 A1 | 1/2011 | Laurent et al. | | 2012/0074201 A1 | 3/2012 | Baxter, III et al. |
| 2011/0011914 A1 | 1/2011 | Baxter, III et al. | | 2012/0080332 A1 | 4/2012 | Shelton, IV et al. |
| 2011/0011915 A1 | 1/2011 | Shelton, IV | | 2012/0080333 A1 | 4/2012 | Woodard, Jr. et al. |
| 2011/0017801 A1 | 1/2011 | Zemlok et al. | | 2012/0080334 A1 | 4/2012 | Shelton, IV et al. |
| 2011/0022032 A1 | 1/2011 | Zemlok et al. | | 2012/0080335 A1 | 4/2012 | Shelton, IV et al. |
| 2011/0024477 A1 | 2/2011 | Hall et al. | | 2012/0080336 A1 | 4/2012 | Shelton, IV et al. |
| 2011/0024478 A1 | 2/2011 | Shelton, IV | | 2012/0080337 A1 | 4/2012 | Shelton, IV et al. |
| 2011/0024479 A1 | 2/2011 | Swensgard et al. | | 2012/0080338 A1 | 4/2012 | Shelton, IV et al. |
| 2011/0036887 A1 | 2/2011 | Zemlok et al. | | 2012/0080339 A1 | 4/2012 | Shelton, IV et al. |
| 2011/0042441 A1 | 2/2011 | Shelton, IV et al. | | 2012/0080340 A1 | 4/2012 | Shelton, IV et al. |
| 2011/0060363 A1 | 3/2011 | Hess et al. | | 2012/0080344 A1 | 4/2012 | Shelton, IV |
| 2011/0062212 A1 | 3/2011 | Shelton, IV et al. | | 2012/0080345 A1 | 4/2012 | Morgan et al. |
| 2011/0068145 A1 | 3/2011 | Bedi et al. | | 2012/0080475 A1 | 4/2012 | Smith et al. |
| 2011/0068148 A1 | 3/2011 | Hall et al. | | 2012/0080477 A1 | 4/2012 | Leimbach et al. |
| 2011/0084112 A1 | 4/2011 | Kostrzewski | | 2012/0080478 A1 | 4/2012 | Morgan et al. |
| 2011/0084113 A1 | 4/2011 | Bedi et al. | | 2012/0080479 A1 | 4/2012 | Shelton, IV |
| 2011/0084115 A1 | 4/2011 | Bedi et al. | | 2012/0080480 A1 | 4/2012 | Woodard, Jr. et al. |
| 2011/0087276 A1 | 4/2011 | Bedi et al. | | 2012/0080481 A1 | 4/2012 | Widenhouse et al. |
| 2011/0087279 A1 | 4/2011 | Shah et al. | | 2012/0080482 A1 | 4/2012 | Schall et al. |
| 2011/0095068 A1 | 4/2011 | Patel | | 2012/0080483 A1 | 4/2012 | Riestenberg et al. |
| 2011/0101065 A1 | 5/2011 | Milliman | | 2012/0080484 A1 | 4/2012 | Morgan et al. |
| 2011/0114697 A1 | 5/2011 | Baxter, III et al. | | 2012/0080485 A1 | 4/2012 | Woodard, Jr. et al. |
| 2011/0114698 A1 | 5/2011 | Baxter, III et al. | | 2012/0080486 A1 | 4/2012 | Woodard, Jr. et al. |
| 2011/0114699 A1 | 5/2011 | Baxter, III et al. | | 2012/0080487 A1 | 4/2012 | Woodard, Jr. et al. |
| 2011/0114700 A1 | 5/2011 | Baxter, III et al. | | 2012/0080488 A1 | 4/2012 | Shelton, IV et al. |
| 2011/0118761 A1 | 5/2011 | Baxter, III et al. | | 2012/0080489 A1 | 4/2012 | Shelton, IV et al. |
| 2011/0121051 A1 | 5/2011 | Shelton, IV et al. | | 2012/0080490 A1 | 4/2012 | Shelton, IV et al. |
| 2011/0121052 A1 | 5/2011 | Shelton, IV et al. | | 2012/0080491 A1 | 4/2012 | Shelton, IV et al. |
| 2011/0125176 A1 | 5/2011 | Yates et al. | | 2012/0080493 A1 | 4/2012 | Shelton, IV et al. |
| 2011/0125177 A1 | 5/2011 | Yates et al. | | 2012/0080496 A1 | 4/2012 | Schall et al. |
| 2011/0132962 A1 | 6/2011 | Hall et al. | | 2012/0080498 A1 | 4/2012 | Shelton, IV et al. |
| 2011/0132963 A1 | 6/2011 | Giordano et al. | | 2012/0080499 A1 | 4/2012 | Schall et al. |
| 2011/0132964 A1 | 6/2011 | Weisenburgh, II et al. | | 2012/0080500 A1 | 4/2012 | Morgan et al. |
| 2011/0132965 A1 | 6/2011 | Moore et al. | | 2012/0080501 A1 | 4/2012 | Morgan et al. |
| 2011/0139852 A1 | 6/2011 | Zingman | | 2012/0080502 A1 | 4/2012 | Morgan et al. |
| 2011/0144430 A1 | 6/2011 | Spivey et al. | | 2012/0080503 A1 | 4/2012 | Woodard, Jr. et al. |
| 2011/0147433 A1 | 6/2011 | Shelton, IV et al. | | 2012/0083833 A1 | 4/2012 | Shelton, IV et al. |
| 2011/0147434 A1 | 6/2011 | Hueil et al. | | 2012/0083834 A1 | 4/2012 | Shelton, IV et al. |
| 2011/0155780 A1 | 6/2011 | Boudreaux | | 2012/0083835 A1 | 4/2012 | Shelton, IV et al. |
| 2011/0155781 A1 | 6/2011 | Swensgard et al. | | 2012/0083836 A1 | 4/2012 | Shelton, IV et al. |
| 2011/0155785 A1 | 6/2011 | Laurent et al. | | 2012/0132450 A1 | 5/2012 | Timm et al. |
| 2011/0155787 A1 | 6/2011 | Baxter, III et al. | | 2012/0138660 A1 | 6/2012 | Shelton, IV |
| 2011/0163147 A1 | 7/2011 | Laurent et al. | | 2012/0160721 A1 | 6/2012 | Shelton, IV et al. |
| 2011/0174860 A1 | 7/2011 | Shelton, IV et al. | | 2012/0175399 A1 | 7/2012 | Shelton et al. |
| 2011/0174861 A1 | 7/2011 | Shelton, IV et al. | | 2012/0187179 A1 | 7/2012 | Gleiman |
| 2011/0174863 A1 | 7/2011 | Shelton, IV et al. | | 2012/0199630 A1 | 8/2012 | Shelton, IV et al. |
| 2011/0178536 A1 | 7/2011 | Kostrzewski | | 2012/0199631 A1 | 8/2012 | Shelton, IV et al. |
| 2011/0192882 A1 | 8/2011 | Hess et al. | | 2012/0199632 A1 | 8/2012 | Spivey et al. |
| 2011/0210156 A1 | 9/2011 | Smith et al. | | 2012/0199633 A1 | 8/2012 | Shelton, IV et al. |
| 2011/0226837 A1 | 9/2011 | Baxter, III et al. | | 2012/0203247 A1 | 8/2012 | Shelton, IV et al. |

| | | | | | | | |
|---|---|---|---|---|---|---|---|
| 2012/0205421 | A1 | 8/2012 | Shelton, IV | EP | 0324636 | B1 | 3/1994 |
| 2012/0211546 | A1 | 8/2012 | Shelton, IV | EP | 0593920 | A1 | 4/1994 |
| 2012/0234890 | A1 | 9/2012 | Aronhalt et al. | EP | 0594148 | A1 | 4/1994 |
| 2012/0234891 | A1 | 9/2012 | Aronhalt et al. | EP | 0427949 | B1 | 6/1994 |
| 2012/0234892 | A1 | 9/2012 | Aronhalt et al. | EP | 0523174 | B1 | 6/1994 |
| 2012/0234893 | A1 | 9/2012 | Schuckmann et al. | EP | 0600182 | A2 | 6/1994 |
| 2012/0234895 | A1 | 9/2012 | O'Connor et al. | EP | 0310431 | B1 | 11/1994 |
| 2012/0234896 | A1 | 9/2012 | Ellerhorst et al. | EP | 0375302 | B1 | 11/1994 |
| 2012/0234897 | A1 | 9/2012 | Shelton, IV et al. | EP | 0376562 | B1 | 11/1994 |
| 2012/0234898 | A1 | 9/2012 | Shelton, IV et al. | EP | 0630612 | A1 | 12/1994 |
| 2012/0234899 | A1 | 9/2012 | Scheib et al. | EP | 0634144 | A1 | 1/1995 |
| 2012/0234900 | A1 | 9/2012 | Swayze | EP | 0646356 | A2 | 4/1995 |
| 2012/0238823 | A1 | 9/2012 | Hagerty et al. | EP | 0646357 | A1 | 4/1995 |
| 2012/0238824 | A1 | 9/2012 | Widenhouse et al. | EP | 0653189 | A2 | 5/1995 |
| 2012/0238826 | A1 | 9/2012 | Yoo et al. | EP | 0669104 | A1 | 8/1995 |
| 2012/0238829 | A1 | 9/2012 | Shelton, IV et al. | EP | 0511470 | B1 | 10/1995 |
| 2012/0239009 | A1 | 9/2012 | Mollere et al. | EP | 0679367 | A2 | 11/1995 |
| 2012/0239010 | A1 | 9/2012 | Shelton, IV et al. | EP | 0392547 | B1 | 12/1995 |
| 2012/0239012 | A1 | 9/2012 | Laurent et al. | EP | 0685204 | A1 | 12/1995 |
| 2012/0239075 | A1 | 9/2012 | Widenhouse et al. | EP | 0364216 | B1 | 1/1996 |
| 2012/0239082 | A1 | 9/2012 | Shelton, IV et al. | EP | 0699418 | A1 | 3/1996 |
| 2012/0241491 | A1 | 9/2012 | Aldridge et al. | EP | 0702937 | A1 | 3/1996 |
| 2012/0241492 | A1 | 9/2012 | Shelton, IV et al. | EP | 0705571 | A1 | 4/1996 |
| 2012/0241493 | A1 | 9/2012 | Baxter, III et al. | EP | 0711611 | A2 | 5/1996 |
| 2012/0241496 | A1 | 9/2012 | Vasudevan et al. | EP | 0484677 | B2 | 6/1996 |
| 2012/0241497 | A1 | 9/2012 | Vasudevan et al. | EP | 0541987 | B1 | 7/1996 |
| 2012/0241498 | A1 | 9/2012 | Gonzalez et al. | EP | 0667119 | B1 | 7/1996 |
| 2012/0241499 | A1 | 9/2012 | Baxter, III et al. | EP | 0708618 | B1 | 3/1997 |
| 2012/0241500 | A1 | 9/2012 | Timmer et al. | EP | 0770355 | A1 | 5/1997 |
| 2012/0241501 | A1 | 9/2012 | Swayze et al. | EP | 0503662 | B1 | 6/1997 |
| 2012/0241502 | A1 | 9/2012 | Aldridge et al. | EP | 0447121 | B1 | 7/1997 |
| 2012/0241503 | A1 | 9/2012 | Baxter, III et al. | EP | 0625077 | B1 | 7/1997 |
| 2012/0241505 | A1 | 9/2012 | Alexander, III et al. | EP | 0633749 | B1 | 8/1997 |
| 2012/0248169 | A1 | 10/2012 | Widenhouse et al. | EP | 0710090 | B1 | 8/1997 |
| 2012/0253298 | A1 | 10/2012 | Henderson et al. | EP | 0578425 | B1 | 9/1997 |
| 2012/0265230 | A1 | 10/2012 | Yates et al. | EP | 0625335 | B1 | 11/1997 |
| 2012/0273551 | A1 | 11/2012 | Shelton, IV et al. | EP | 0552423 | B1 | 1/1998 |
| 2012/0283707 | A1 | 11/2012 | Giordano et al. | EP | 0592244 | B1 | 1/1998 |
| 2012/0286019 | A1 | 11/2012 | Hueil et al. | EP | 0648476 | B1 | 1/1998 |
| 2012/0292367 | A1 | 11/2012 | Morgan et al. | EP | 0649290 | B1 | 3/1998 |
| 2012/0292370 | A1 | 11/2012 | Hess et al. | EP | 0598618 | B1 | 9/1998 |
| 2012/0298719 | A1 | 11/2012 | Shelton, IV et al. | EP | 0676173 | B1 | 9/1998 |
| 2013/0012931 | A1 | 1/2013 | Spivey et al. | EP | 0678007 | B1 | 9/1998 |
| 2013/0012957 | A1 | 1/2013 | Shelton, IV et al. | EP | 0603472 | B1 | 11/1998 |
| | | | | EP | 0605351 | B1 | 11/1998 |
| | FOREIGN PATENT DOCUMENTS | | | EP | 0878169 | A1 | 11/1998 |
| CA | 2514274 | A1 | 1/2006 | EP | 0879742 | A1 | 11/1998 |
| CN | 1634601 | A | 7/2005 | EP | 0695144 | B1 | 12/1998 |
| CN | 1868411 | A | 11/2006 | EP | 0722296 | B1 | 12/1998 |
| CN | 1915180 | A | 2/2007 | EP | 0760230 | B1 | 2/1999 |
| CN | 101095621 | A | 1/2008 | EP | 0623316 | B1 | 3/1999 |
| DE | 273689 | C | 5/1914 | EP | 0650701 | B1 | 3/1999 |
| DE | 1775926 | A | 1/1972 | EP | 0537572 | B1 | 6/1999 |
| DE | 3036217 | A1 | 4/1982 | EP | 0923907 | A1 | 6/1999 |
| DE | 3210466 | A1 | 9/1983 | EP | 0843906 | B1 | 3/2000 |
| DE | 9412228 | U | 9/1994 | EP | 0552050 | B1 | 5/2000 |
| DE | 19509116 | A1 | 9/1996 | EP | 0833592 | B1 | 5/2000 |
| DE | 19851291 | A1 | 1/2000 | EP | 0830094 | B1 | 9/2000 |
| DE | 19924311 | A1 | 11/2000 | EP | 1034747 | A1 | 9/2000 |
| DE | 69328576 | T2 | 1/2001 | EP | 1034748 | A1 | 9/2000 |
| DE | 10052679 | A1 | 5/2001 | EP | 0694290 | B1 | 11/2000 |
| DE | 20112837 | U1 | 10/2001 | EP | 1050278 | A1 | 11/2000 |
| DE | 20121753 | U1 | 4/2003 | EP | 1053719 | A1 | 11/2000 |
| DE | 10314072 | A1 | 10/2004 | EP | 1053720 | A1 | 11/2000 |
| DE | 202007003114 | U1 | 6/2007 | EP | 1055399 | A1 | 11/2000 |
| EP | 0122046 | A1 | 10/1984 | EP | 1055400 | A1 | 11/2000 |
| EP | 0070230 | B1 | 10/1985 | EP | 1080694 | B1 | 3/2001 |
| EP | 0156774 | A2 | 10/1985 | EP | 1090592 | A1 | 4/2001 |
| EP | 0387980 | B1 | 10/1985 | EP | 1095627 | A1 | 5/2001 |
| EP | 0033548 | B1 | 5/1986 | EP | 1256318 | B1 | 5/2001 |
| EP | 0129442 | B1 | 11/1987 | EP | 0806914 | B1 | 9/2001 |
| EP | 0276104 | A2 | 7/1988 | EP | 0768840 | B1 | 12/2001 |
| EP | 0178941 | B1 | 1/1991 | EP | 0908152 | B1 | 1/2002 |
| EP | 0248844 | B1 | 1/1993 | EP | 0872213 | B1 | 5/2002 |
| EP | 0545029 | A1 | 6/1993 | EP | 0862386 | B1 | 6/2002 |
| EP | 0277959 | B1 | 10/1993 | EP | 0949886 | B1 | 9/2002 |
| EP | 0233940 | B1 | 11/1993 | EP | 1238634 | A2 | 9/2002 |
| EP | 0261230 | B1 | 11/1993 | EP | 0858295 | B1 | 12/2002 |
| EP | 0639349 | A2 | 2/1994 | EP | 0656188 | B1 | 1/2003 |

| | | | | | | |
|---|---|---|---|---|---|---|
| EP | 1284120 | A1 | 2/2003 | EP | 1767163 A1 | 3/2007 |
| EP | 1287788 | A1 | 3/2003 | EP | 1769756 A1 | 4/2007 |
| EP | 0717966 | B1 | 4/2003 | EP | 1769758 A1 | 4/2007 |
| EP | 0869742 | B1 | 5/2003 | EP | 1581128 B1 | 5/2007 |
| EP | 0829235 | B1 | 6/2003 | EP | 1785097 A2 | 5/2007 |
| EP | 0887046 | B1 | 7/2003 | EP | 1790293 A2 | 5/2007 |
| EP | 0852480 | B1 | 8/2003 | EP | 1800610 A1 | 6/2007 |
| EP | 0891154 | B1 | 9/2003 | EP | 1300117 B1 | 8/2007 |
| EP | 0813843 | B1 | 10/2003 | EP | 1813199 A1 | 8/2007 |
| EP | 0873089 | B1 | 10/2003 | EP | 1813201 A1 | 8/2007 |
| EP | 0856326 | B1 | 11/2003 | EP | 1813203 A2 | 8/2007 |
| EP | 1374788 | A1 | 1/2004 | EP | 1813207 A1 | 8/2007 |
| EP | 0741996 | B1 | 2/2004 | EP | 1813209 A1 | 8/2007 |
| EP | 0814712 | B1 | 2/2004 | EP | 1487359 B1 | 10/2007 |
| EP | 1402837 | A1 | 3/2004 | EP | 1599146 B1 | 10/2007 |
| EP | 0705570 | B1 | 4/2004 | EP | 1839596 A1 | 10/2007 |
| EP | 0959784 | B1 | 4/2004 | EP | 2110083 A2 | 10/2007 |
| EP | 1407719 | A2 | 4/2004 | EP | 1857057 A2 | 11/2007 |
| EP | 1086713 | B1 | 5/2004 | EP | 1402821 B1 | 12/2007 |
| EP | 0996378 | B1 | 6/2004 | EP | 1872727 A1 | 1/2008 |
| EP | 1426012 | A1 | 6/2004 | EP | 1897502 A1 | 3/2008 |
| EP | 0833593 | B2 | 7/2004 | EP | 1330201 B1 | 6/2008 |
| EP | 1442694 | A1 | 8/2004 | EP | 1702568 B1 | 7/2008 |
| EP | 0888749 | B1 | 9/2004 | EP | 1943957 A2 | 7/2008 |
| EP | 0959786 | B1 | 9/2004 | EP | 1943964 A1 | 7/2008 |
| EP | 1459695 | A1 | 9/2004 | EP | 1943976 A2 | 7/2008 |
| EP | 1473819 | A1 | 11/2004 | EP | 1593337 B1 | 8/2008 |
| EP | 1477119 | A1 | 11/2004 | EP | 1970014 A1 | 9/2008 |
| EP | 1479345 | A1 | 11/2004 | EP | 1980213 A2 | 10/2008 |
| EP | 1479347 | A1 | 11/2004 | EP | 1759645 B1 | 11/2008 |
| EP | 1479348 | A1 | 11/2004 | EP | 1990014 A2 | 11/2008 |
| EP | 0754437 | B2 | 12/2004 | EP | 1693008 B1 | 12/2008 |
| EP | 1025807 | B1 | 12/2004 | EP | 1759640 B1 | 12/2008 |
| EP | 1001710 | B1 | 1/2005 | EP | 2000102 A2 | 12/2008 |
| EP | 1520521 | A1 | 4/2005 | EP | 2008595 A2 | 12/2008 |
| EP | 1520523 | A1 | 4/2005 | EP | 1736104 B1 | 3/2009 |
| EP | 1520525 | A1 | 4/2005 | EP | 1749486 B1 | 3/2009 |
| EP | 1522264 | A1 | 4/2005 | EP | 2039316 A2 | 3/2009 |
| EP | 1523942 | A2 | 4/2005 | EP | 1721576 B1 | 4/2009 |
| EP | 1550408 | A1 | 7/2005 | EP | 1733686 B1 | 4/2009 |
| EP | 1557129 | A1 | 7/2005 | EP | 2044890 A1 | 4/2009 |
| EP | 1064883 | B1 | 8/2005 | EP | 1550413 B1 | 6/2009 |
| EP | 1067876 | B1 | 8/2005 | EP | 1745748 B1 | 8/2009 |
| EP | 0870473 | B1 | 9/2005 | EP | 2090237 A1 | 8/2009 |
| EP | 1157666 | B1 | 9/2005 | EP | 2090244 A2 | 8/2009 |
| EP | 0880338 | B1 | 10/2005 | EP | 2090245 A1 | 8/2009 |
| EP | 1158917 | B1 | 11/2005 | EP | 2090256 A2 | 8/2009 |
| EP | 1344498 | B1 | 11/2005 | EP | 2095777 A2 | 9/2009 |
| EP | 1330989 | B1 | 12/2005 | EP | 2110082 A1 | 10/2009 |
| EP | 0771176 | B2 | 1/2006 | EP | 1813208 B1 | 11/2009 |
| EP | 1621138 | A2 | 2/2006 | EP | 2116195 A1 | 11/2009 |
| EP | 1621139 | A2 | 2/2006 | EP | 1607050 B1 | 12/2009 |
| EP | 1621141 | A2 | 2/2006 | EP | 1815804 B1 | 12/2009 |
| EP | 1621145 | A2 | 2/2006 | EP | 1566150 B1 | 4/2010 |
| EP | 1621151 | A2 | 2/2006 | EP | 1813206 B1 | 4/2010 |
| EP | 1034746 | B1 | 3/2006 | EP | 1769754 B1 | 6/2010 |
| EP | 1632191 | A2 | 3/2006 | EP | 1535565 B1 | 10/2010 |
| EP | 1065981 | B1 | 5/2006 | EP | 1702570 B1 | 10/2010 |
| EP | 1082944 | B1 | 5/2006 | EP | 1785098 B1 | 10/2010 |
| EP | 1652481 | A2 | 5/2006 | EP | 2030578 B1 | 11/2010 |
| EP | 1382303 | B1 | 6/2006 | EP | 1627605 B1 | 12/2010 |
| EP | 1253866 | B1 | 7/2006 | EP | 1813205 B1 | 6/2011 |
| EP | 1032318 | B1 | 8/2006 | EP | 1785102 B1 | 1/2012 |
| EP | 1045672 | B1 | 8/2006 | FR | 999646 A | 2/1952 |
| EP | 1617768 | B1 | 8/2006 | FR | 1112936 A | 3/1956 |
| EP | 1693015 | A2 | 8/2006 | FR | 2598905 A1 | 11/1987 |
| EP | 1400214 | B1 | 9/2006 | FR | 2765794 A | 1/1999 |
| EP | 1702567 | A2 | 9/2006 | GB | 939929 A | 10/1963 |
| EP | 1129665 | B1 | 11/2006 | GB | 1210522 A | 10/1970 |
| EP | 1400206 | B1 | 11/2006 | GB | 1217159 A | 12/1970 |
| EP | 1721568 | A1 | 11/2006 | GB | 1339394 A | 12/1973 |
| EP | 1256317 | B1 | 12/2006 | GB | 2109241 A | 6/1983 |
| EP | 1285633 | B1 | 12/2006 | GB | 2272159 A | 5/1994 |
| EP | 1728473 | A1 | 12/2006 | GB | 2284242 A | 5/1995 |
| EP | 1728475 | A2 | 12/2006 | GB | 2336214 A | 10/1999 |
| EP | 1479346 | B1 | 1/2007 | GB | 2425903 A | 11/2006 |
| EP | 1484024 | B1 | 1/2007 | JP | S 58500053 A | 1/1983 |
| EP | 1754445 | A2 | 2/2007 | JP | 61-98249 A | 5/1986 |
| EP | 1759812 | A1 | 3/2007 | JP | 63-203149 | 8/1988 |

| | | | | | | |
|---|---|---|---|---|---|---|
| JP | 3-12126 | A | 1/1991 | WO | WO 96/24301 A1 | 8/1996 |
| JP | 5-212039 | A | 8/1993 | WO | WO 96/27337 A1 | 9/1996 |
| JP | 6007357 | A | 1/1994 | WO | WO 96/31155 A1 | 10/1996 |
| JP | 7051273 | A | 2/1995 | WO | WO 96/35464 A1 | 11/1996 |
| JP | 8033641 | A | 2/1996 | WO | WO 96/39085 A1 | 12/1996 |
| JP | 8229050 | A | 9/1996 | WO | WO 96/39086 A1 | 12/1996 |
| JP | 2000033071 | A | 2/2000 | WO | WO 96/39087 A1 | 12/1996 |
| JP | 2000171730 | A | 6/2000 | WO | WO 96/39088 A1 | 12/1996 |
| JP | 2000287987 | A | 10/2000 | WO | WO 96/39089 A1 | 12/1996 |
| JP | 2000325303 | A | 11/2000 | WO | WO 97/00646 A1 | 1/1997 |
| JP | 2001-514541 | A | 9/2001 | WO | WO 97/00647 A1 | 1/1997 |
| JP | 2001286477 | A | 10/2001 | WO | WO 97/06582 A1 | 2/1997 |
| JP | 2002143078 | A | 5/2002 | WO | WO 97/10763 A1 | 3/1997 |
| JP | 2002369820 | A | 12/2002 | WO | WO 97/10764 A1 | 3/1997 |
| JP | 2003-500153 | A | 1/2003 | WO | WO 97/11648 A2 | 4/1997 |
| JP | 2004-344663 | | 12/2004 | WO | WO 97/11649 A1 | 4/1997 |
| JP | 2005-028149 | A | 2/2005 | WO | WO 97/15237 A1 | 5/1997 |
| JP | 2005505322 | T | 2/2005 | WO | WO 97/24073 A1 | 7/1997 |
| JP | 2005103293 | A | 4/2005 | WO | WO 97/24993 A1 | 7/1997 |
| JP | 2005131163 | A | 5/2005 | WO | WO 97/30644 A1 | 8/1997 |
| JP | 2005131164 | A | 5/2005 | WO | WO 97/34533 A1 | 9/1997 |
| JP | 2005131173 | A | 5/2005 | WO | WO 97/37598 A1 | 10/1997 |
| JP | 2005131211 | A | 5/2005 | WO | WO 97/39688 A2 | 10/1997 |
| JP | 2005131212 | A | 5/2005 | WO | WO 98/17180 A1 | 4/1998 |
| JP | 2005137423 | A | 6/2005 | WO | WO 98/27880 A1 | 7/1998 |
| JP | 2005152416 | A | 6/2005 | WO | WO 98/30153 A1 | 7/1998 |
| JP | 2005-523105 | A | 8/2005 | WO | WO 98/47436 A1 | 10/1998 |
| JP | 2005524474 | A | 8/2005 | WO | WO 99/03407 A1 | 1/1999 |
| JP | 2006-281405 | A | 10/2006 | WO | WO 99/03408 A1 | 1/1999 |
| RU | 2008830 | C1 | 3/1994 | WO | WO 99/03409 A1 | 1/1999 |
| RU | 2187249 | C2 | 8/2002 | WO | WO 99/12483 A1 | 3/1999 |
| RU | 2225170 | C2 | 3/2004 | WO | WO 99/12487 A1 | 3/1999 |
| SU | 189517 | A | 1/1967 | WO | WO 99/12488 A1 | 3/1999 |
| SU | 328636 | A | 9/1972 | WO | WO 99/15086 A1 | 4/1999 |
| SU | 886900 | A1 | 12/1981 | WO | WO 99/15091 A1 | 4/1999 |
| SU | 1009439 | A | 4/1983 | WO | WO 99/23933 A2 | 5/1999 |
| SU | 1333319 | A2 | 8/1987 | WO | WO 99/23959 A1 | 5/1999 |
| SU | 1377053 | A1 | 2/1988 | WO | WO 99/25261 A1 | 5/1999 |
| SU | 1561964 | A1 | 5/1990 | WO | WO 99/29244 A1 | 6/1999 |
| SU | 1722476 | A1 | 3/1992 | WO | WO 99/34744 A1 | 7/1999 |
| WO | WO 82/02824 | A1 | 9/1982 | WO | WO 99/45849 A1 | 9/1999 |
| WO | WO 91/15157 | A1 | 10/1991 | WO | WO 99/48430 A1 | 9/1999 |
| WO | WO 92/20295 | A1 | 11/1992 | WO | WO 99/51158 A1 | 10/1999 |
| WO | WO 92/21300 | A1 | 12/1992 | WO | WO 00/24322 A1 | 5/2000 |
| WO | WO 93/08755 | A1 | 5/1993 | WO | WO 00/24330 A1 | 5/2000 |
| WO | WO 93/13718 | A1 | 7/1993 | WO | WO 00/41638 A1 | 7/2000 |
| WO | WO 93/14690 | A1 | 8/1993 | WO | WO 00/48506 A1 | 8/2000 |
| WO | WO 93/15850 | A1 | 8/1993 | WO | WO 00/53112 A2 | 9/2000 |
| WO | WO 9315648 | A1 * | 8/1993 | WO | WO 00/54653 A1 | 9/2000 |
| WO | WO 93/19681 | A1 | 10/1993 | WO | WO 00/57796 A1 | 10/2000 |
| WO | WO 94/00060 | A1 | 1/1994 | WO | WO 00/64365 A1 | 11/2000 |
| WO | WO 94/11057 | A1 | 5/1994 | WO | WO 00/72762 A1 | 12/2000 |
| WO | WO 94/12108 | A1 | 6/1994 | WO | WO 00/72765 A1 | 12/2000 |
| WO | WO 94/18893 | A1 | 9/1994 | WO | WO 01/03587 A1 | 1/2001 |
| WO | WO 94/22378 | A1 | 10/1994 | WO | WO 01/05702 A1 | 1/2001 |
| WO | WO 94/23659 | A1 | 10/1994 | WO | WO 01/10482 A1 | 2/2001 |
| WO | WO 95/02369 | A1 | 1/1995 | WO | WO 01/35845 A1 | 5/2001 |
| WO | WO 95/03743 | A1 | 2/1995 | WO | WO 01/54594 A1 | 8/2001 |
| WO | WO 95/06817 | A1 | 3/1995 | WO | WO 01/58371 A1 | 8/2001 |
| WO | WO 95/09576 | A1 | 4/1995 | WO | WO 01/62158 A2 | 8/2001 |
| WO | WO 95/09577 | A1 | 4/1995 | WO | WO 01/62161 A1 | 8/2001 |
| WO | WO 95/14436 | A1 | 6/1995 | WO | WO 01/62162 A1 | 8/2001 |
| WO | WO 95/17855 | A1 | 7/1995 | WO | WO 01/62164 A2 | 8/2001 |
| WO | WO 95/18383 | A1 | 7/1995 | WO | WO 01/62169 A2 | 8/2001 |
| WO | WO 95/18572 | A1 | 7/1995 | WO | WO 01/78605 A2 | 10/2001 |
| WO | WO 95/19739 | A1 | 7/1995 | WO | WO 01/91646 A1 | 12/2001 |
| WO | WO 95/20360 | A1 | 8/1995 | WO | WO 02/07608 A1 | 1/2002 |
| WO | WO 95/23557 | A1 | 9/1995 | WO | WO 02/07618 A1 | 1/2002 |
| WO | WO 95/24865 | A1 | 9/1995 | WO | WO 02/17799 A1 | 3/2002 |
| WO | WO 95/25471 | A3 | 9/1995 | WO | WO 02/19920 A1 | 3/2002 |
| WO | WO 95/26562 | A1 | 10/1995 | WO | WO 02/19932 A1 | 3/2002 |
| WO | WO 95/29639 | A1 | 11/1995 | WO | WO 02/30297 A2 | 4/2002 |
| WO | WO 96/04858 | A1 | 2/1996 | WO | WO 02/32322 A2 | 4/2002 |
| WO | WO 96/19151 | A1 | 6/1996 | WO | WO 02/36028 A1 | 5/2002 |
| WO | WO 96/19152 | A1 | 6/1996 | WO | WO 02/43571 A2 | 6/2002 |
| WO | WO 96/20652 | A1 | 7/1996 | WO | WO 02/058568 A1 | 8/2002 |
| WO | WO 96/21119 | A1 | 7/1996 | WO | WO 02/060328 A1 | 8/2002 |
| WO | WO 96/22055 | A1 | 7/1996 | WO | WO 02/067785 A2 | 9/2002 |
| WO | WO 96/23448 | A1 | 8/1996 | WO | WO 02/098302 A1 | 12/2002 |

| | | | |
|---|---|---|---|
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03090630 A2 * | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/070763 A1 | 6/2008 |
| WO | WO 2008/089404 A2 | 7/2008 |
| WO | WO 2008/109125 A1 | 9/2008 |
| WO | WO 2010/063795 A1 | 6/2010 |
| WO | WO 2012/044844 A2 | 4/2012 |

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 a Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

U.S. Appl. No. 13/488,903, filed Jun. 5, 2012.

European Examination Report, Application No. 08250080.2, dated Jun. 14, 2010 (4 pages).

International Search Report for PCT/US2012/026997, May 7, 2012 (5 pages).

Written Opinion for PCT/US2012/026997, May 7, 2012 (6 pages).

International Search Report for PCT/US2012/039156, Oct. 29, 2012 (4 pages).

Written Opinion for PCT/US2012/039156, Oct. 29, 2012 (6 pages).

European Search Report for Application No. 12173458.6, dated Dec. 6, 2012 (8 pages).

* cited by examiner

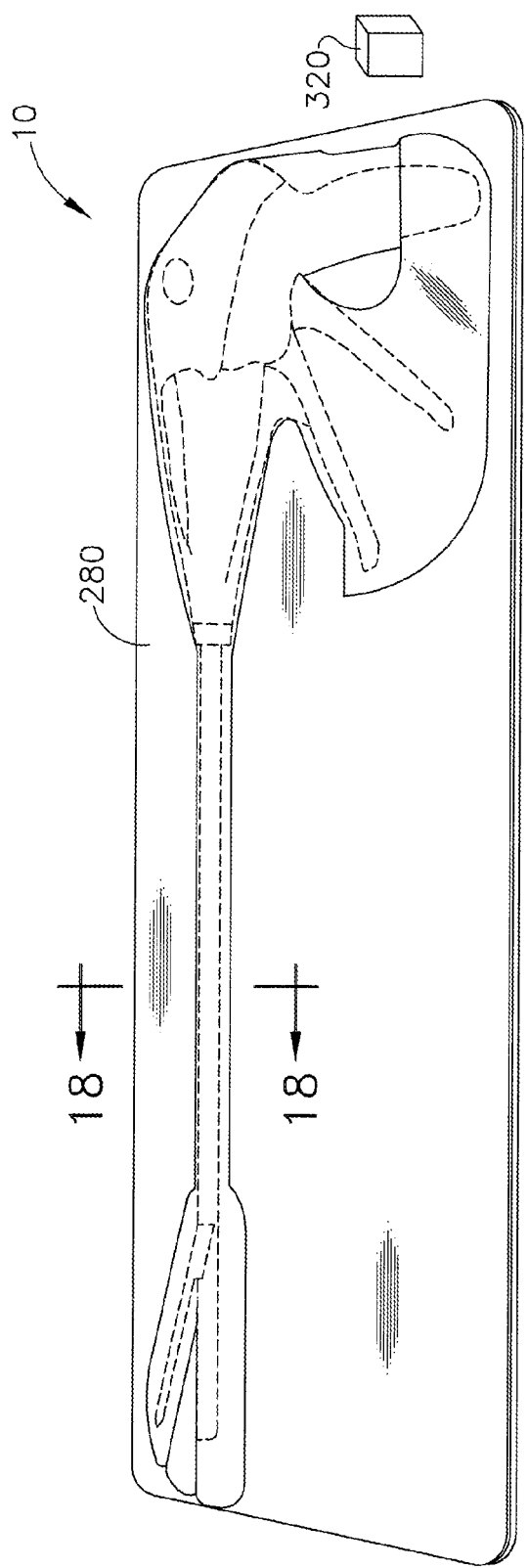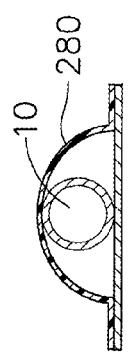
FIG. 17
FIG. 18

SURGICAL INSTRUMENT WITH WIRELESS COMMUNICATION BETWEEN CONTROL UNIT AND REMOTE SENSOR

CROSS REFERENCE TO RELATED APPLICATIONS

The present application is related to the following, concurrently-filed U.S. patent applications, which are incorporated herein by reference:

(1) U.S. patent application Ser. No. 11/651,715, entitled "SURGICAL INSTRUMENT WITH WIRELESS COMMUNICATION BETWEEN CONTROL UNIT AND SENSOR TRANSPONDERS," by J. Giordano et al.;

(2) U.S. patent application Ser. No. 11/651,806, entitled "SURGICAL INSTRUMENT WITH ELEMENTS TO COMMUNICATE BETWEEN CONTROL UNIT AND END EFFECTOR," by J. Giordano et al.;

(3) U.S. patent application Ser. No. 11/651,768, entitled "PREVENTION OF CARTRIDGE REUSE IN A SURGICAL INSTRUMENT," by F. Shelton et al.;

(4) U.S. patent application Ser. No. 11/651,771, entitled "POST-STERILIZATION PROGRAMMING OF SURGICAL INSTRUMENTS," by J. Swayze et al.;

(5) U.S. patent application Ser. No. 11/651,788, entitled "INTERLOCK AND SURGICAL INSTRUMENT INCLUDING SAME," by F. Shelton et al.; and (6) U.S. patent application Ser. No. 11/651,785, entitled "SURGICAL INSTRUMENT WITH ENHANCED BATTERY PERFORMANCE," by F. Shelton et al.

BACKGROUND

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895, which discloses an endocutter with distinct closing and firing actions. A clinician using this device is able to close the jaw members upon tissue to position the tissue prior to firing. Once the clinician has determined that the jaw members are properly gripping tissue, the clinician can then fire the surgical stapler with a single firing stroke, thereby severing and stapling the tissue. The simultaneous severing and stapling avoids complications that may arise when performing such actions sequentially with different surgical tools that respectively only sever and staple.

One specific advantage of being able to close upon tissue before firing is that the clinician is able to verify via an endoscope that the desired location for the cut has been achieved, including that a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing.

Endoscopic staplers/cutters continue to increase in complexity and function with each generation. One of the main reasons for this is the quest to lower force-to-fire (FTF) to a level that all or a great majority of surgeons can handle. One known solution to lower FTF it use $CO_2$ or electrical motors. These devices have not faired much better than traditional hand-powered devices, but for a different reason. Surgeons typically prefer to experience proportionate force distribution to that being experienced by the end effector in the forming of the staple to assure them that the cutting/stapling cycle is complete, with the upper limit within the capabilities of most surgeons (usually around 15-30 lbs). They also typically want to maintain control of deploying the staples and being able to stop at anytime if the forces felt in the handle of the device feel too great or for some other clinical reason.

To address this need, so-called "power-assist" endoscopic surgical instruments have been developed in which a supplemental power source aids in the firing of the instrument. For example, in some power-assist devices, a motor provides supplemental electrical power to the power input by the user from squeezing the firing trigger. Such devices are capable of providing loading force feedback and control to the operator to reduce the firing force required to be exerted by the operator in order to complete the cutting operation. One such power-assist device is described in U.S. patent application Ser. No. 11/343,573, filed Jan. 31, 2006 by Shelton et al., entitled "Motor-driven surgical cutting and fastening instrument with loading force feedback," ("the '573 application") which is incorporated herein by reference.

These power-assist devices often include other components that purely mechanical endoscopic surgical instruments do not, such as sensors and control systems. One challenge in using such electronics in a surgical instrument is delivering power and/or data to and from the sensors, particularly when there is a free rotating joint in the surgical instrument.

SUMMARY

In one general aspect, the present invention is directed to a surgical instrument, such as an endoscopic or laparoscopic instrument. According to one embodiment, the surgical instrument comprises an end effector comprising at least one sensor transponder that is passively powered. The surgical instrument also comprises a shaft having a distal end connected to the end effector and a handle connected to a proximate end of the shaft. The handle comprises a control unit (e.g., a microcontroller) that is in communication with the sensor transponder via at least one inductive coupling. Further, the surgical instrument may comprise a rotational joint for rotating the shaft. In such a case, the surgical instrument may comprise a first inductive element located in the shaft distally from the rotational joint and inductively coupled to the control unit, and a second inductive element located distally in the shaft and inductively coupled to the at least one sensor transponder. The first and second inductive elements may be connected by a wired, physical connection.

That way, the control unit may communicate with the transponder in the end effector without a direct wired connection through complex mechanical joints like the rotating joint where it may be difficult to maintain such a wired connection. In addition, because the distances between the inductive elements may be fixed and known, the couplings could be optimized for inductive transfer of energy. Also, the distances could be relatively short so that relatively low power signals could be used to thereby minimize interference with other systems in the use environment of the instrument.

In another general aspect of the present invention, the electrically conductive shaft of the surgical instrument may serve as an antenna for the control unit to wirelessly communicate signals to and from the sensor transponder. For example, the sensor transponder could be located on or disposed in a nonconductive component of the end effector, such as a plastic cartridge, thereby insulating the sensor from conductive components of the end effector and the shaft. In addition, the control unit in the handle may be electrically coupled to the shaft. In that way, the shaft and/or the end effector may serve as an antenna for the control unit by radiating signals from the control unit to the sensor and/or by receiving radiated signals from the sensor. Such a design is particularly useful in surgical instruments having complex mechanical joints (such as rotary joints), which make it difficult to use a direct wired connection between the sensor and control unit for communicating data signals.

In another embodiment, the shaft and/or components of the end effector could serve as the antenna for the sensor by radiating signals to the control unit and receiving radiated signals from the control unit. According to such an embodiment, the control unit is electrically insulated from the shaft and the end effector.

In another general aspect, the present invention is directed to a surgical instrument comprising a programmable control unit that can be programmed by a programming device after the instrument has been packaged and sterilized. In one such embodiment, the programming device may wirelessly program the control unit. The control unit may be passively powered by the wireless signals from the programming device during the programming operation. In another embodiment, the sterile container may comprise a connection interface so that the programming unit can be connected to the surgical instrument while the surgical instrument is in its sterilized container.

FIGURES

Various embodiments of the present invention are described herein by way of example in conjunction with the following figures wherein.

Figure 12:
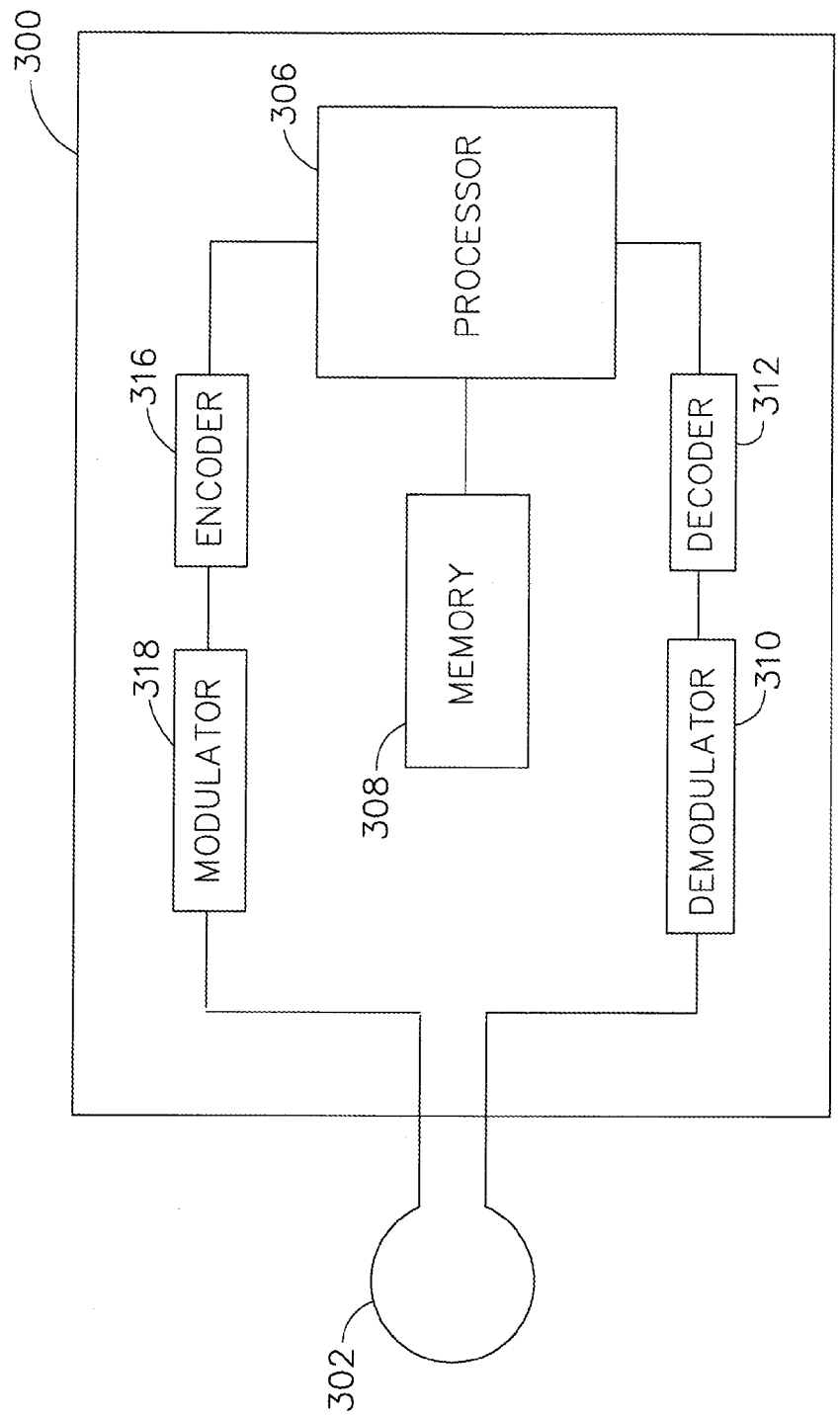
Figure 15:
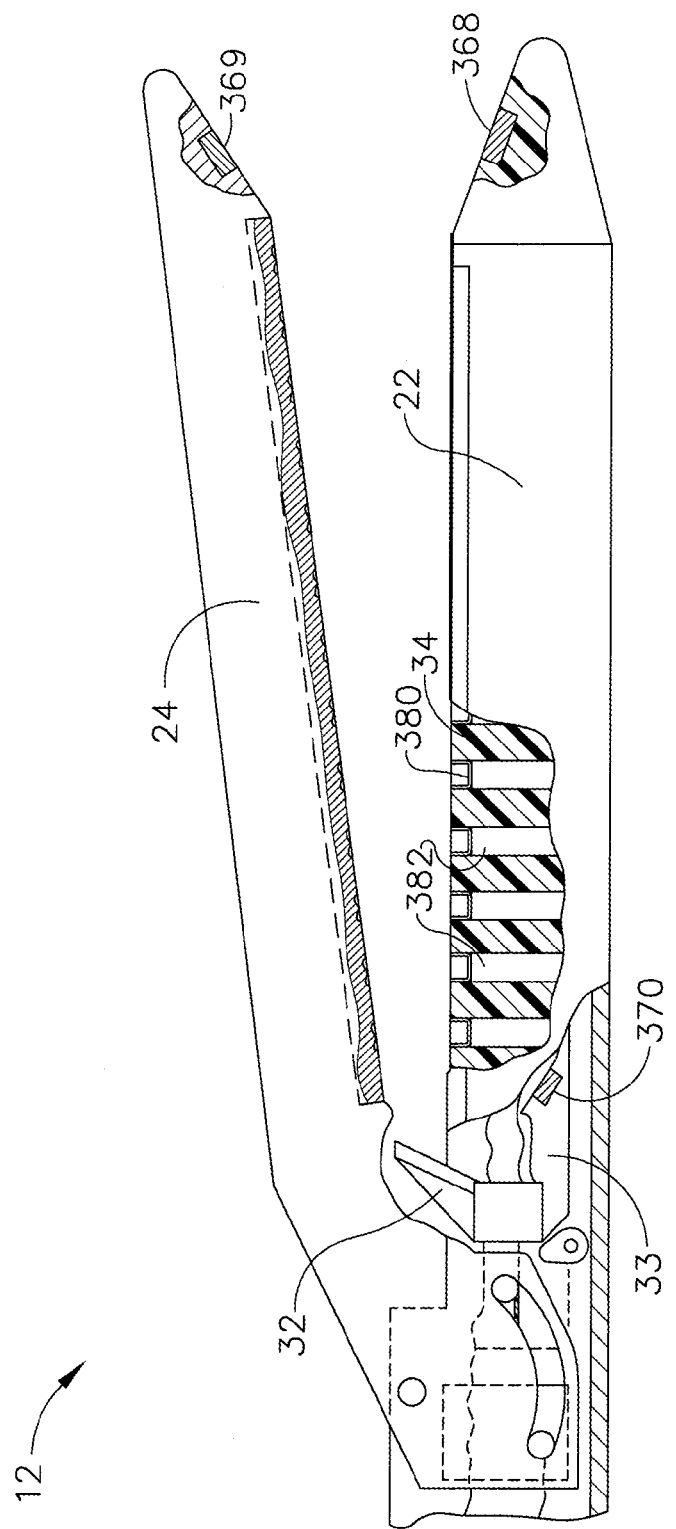
Figure 19:
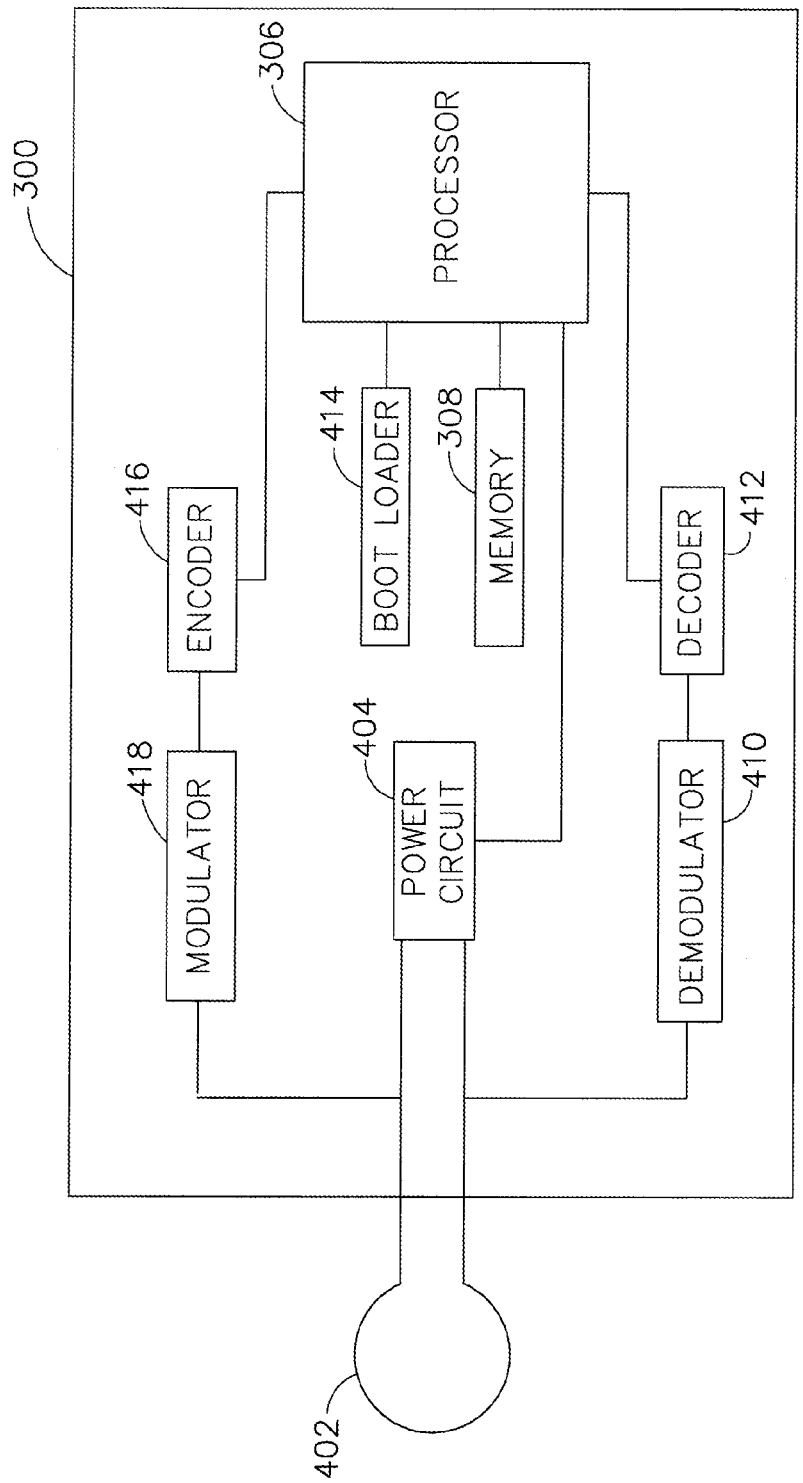
Figure 20:
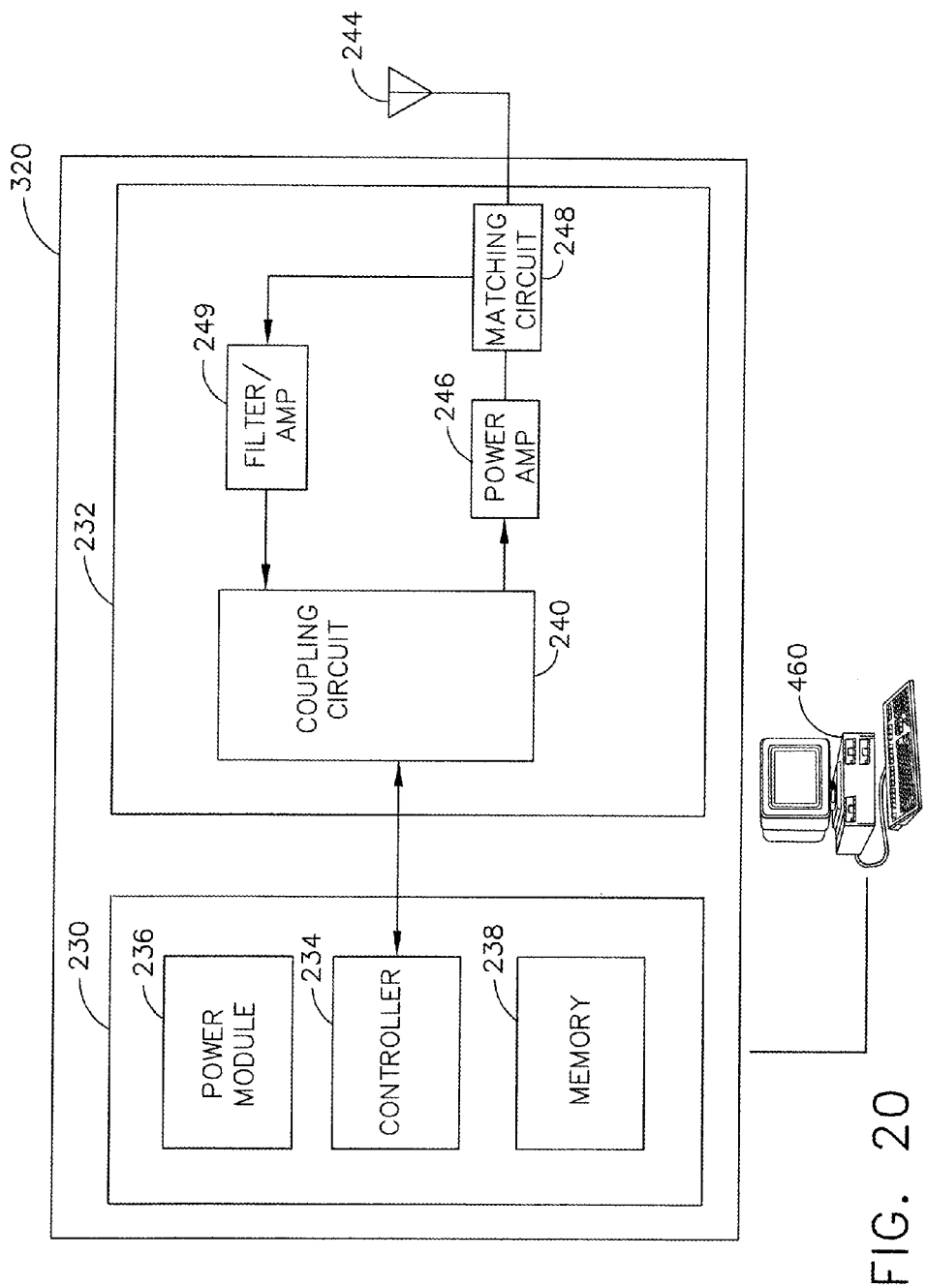
Figure 21:
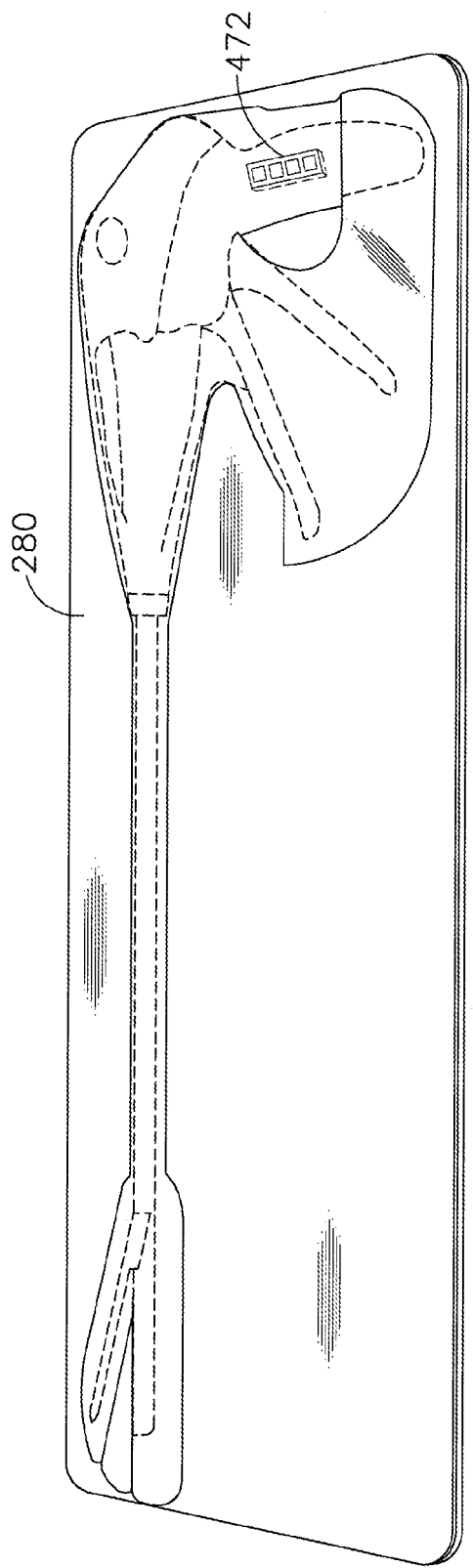

FIGS. 11, 13-14, 16, and 22 are perspective views of a surgical instrument according to various embodiments of the present invention;

FIGS. 12 and 19 are block diagrams of a control unit according to various embodiments of the present invention;

FIG. 15 is a side view of an end effector including a sensor transponder according to various embodiments of the present invention;

FIGS. 17 and 18 show the instrument in a sterile container according to various embodiments of the present invention;

FIG. 20 is a block diagram of the remote programming device according to various embodiments of the present invention; and FIG. 21 is a diagram of a packaged instrument according to various embodiments of the present invention.

DETAILED DESCRIPTION

Various embodiments of the present invention are directed generally to a surgical instrument having at least one remote sensor transponder and means for communicating power and/or data signals to the transponder(s) from a control unit. The present invention may be used with any type of surgical instrument comprising at least one sensor transponder, such as endoscopic or laparoscopic surgical instruments, but is particularly useful for surgical instruments where some feature of the instrument, such as a free rotating joint, prevents or otherwise inhibits the use of a wired connection to the sensor(s). Before describing aspects of the system, one type of surgical instrument in which embodiments of the present invention may be used—an endoscopic stapling and cutting instrument (i.e., an endocutter)—is first described by way of illustration.

Figure 1:
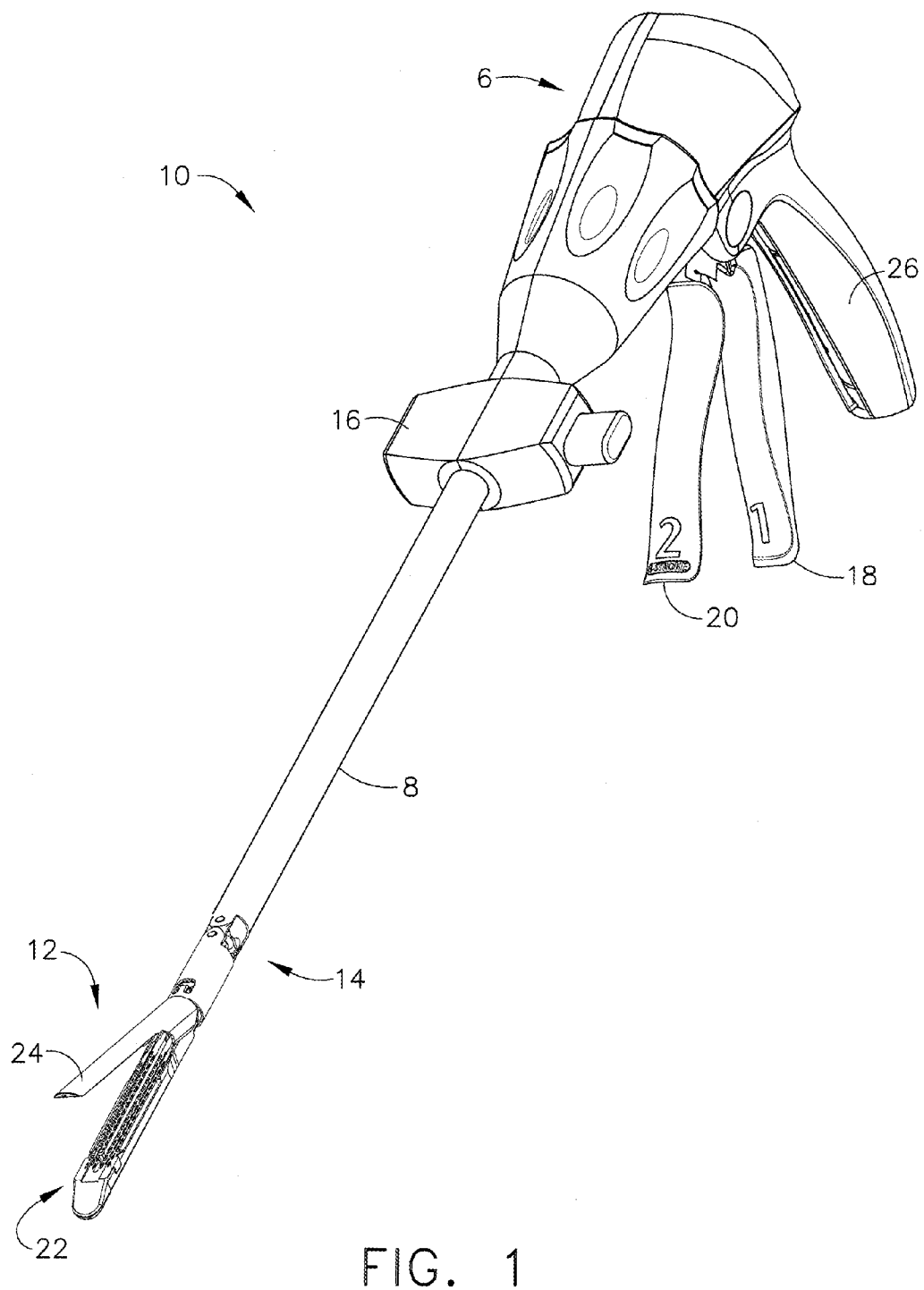
FIGS. 1 and 2 are perspective views of a surgical instrument according to various embodiments of the present invention.
Figure 2:
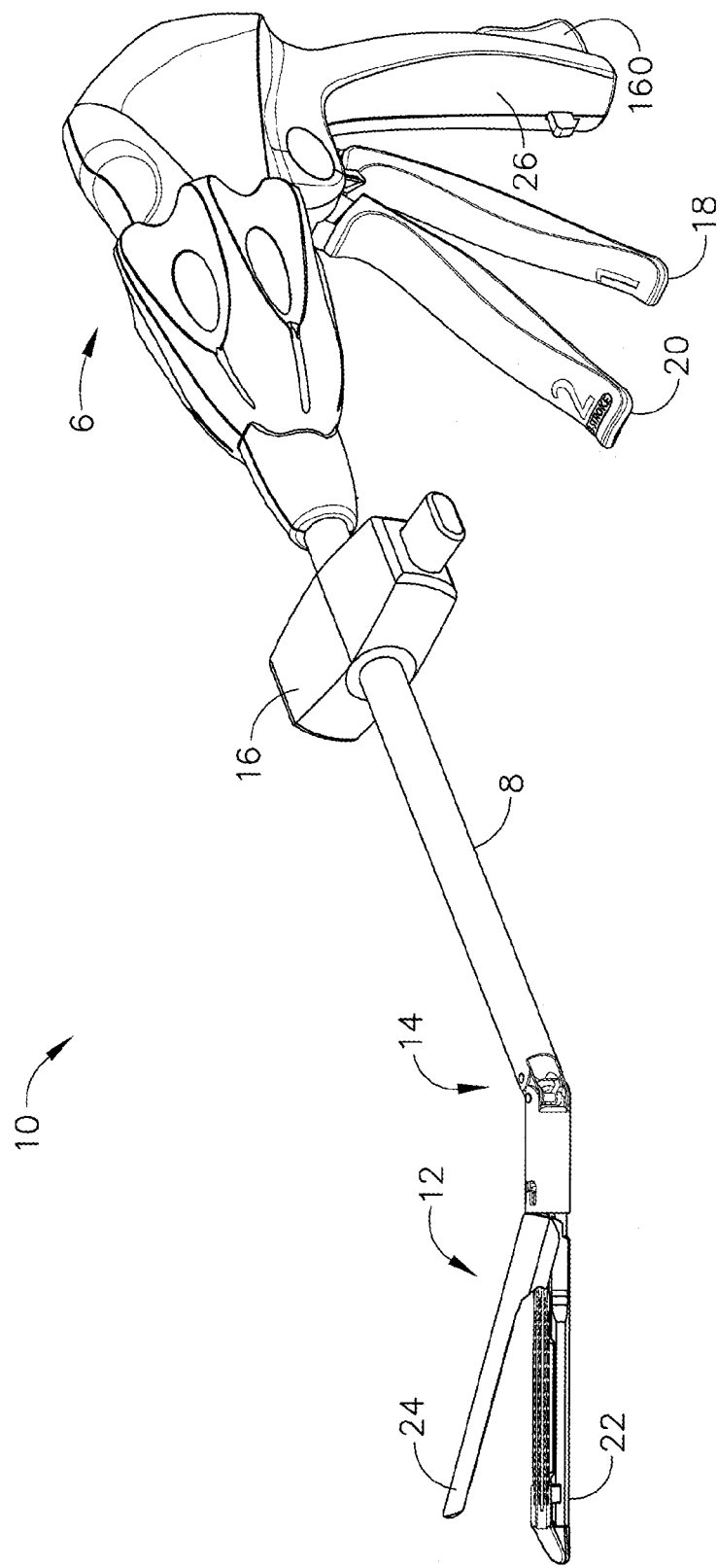

FIGS. 1 and 2 depict an endoscopic surgical instrument 10 that comprises a handle 6, a shaft 8, and an articulating end effector 12 pivotally connected to the shaft 8 at an articulation pivot 14. Correct placement and orientation of the end effector 12 may be facilitated by controls on the hand 6, including (1) a rotation knob 28 for rotating the closure tube (described in more detail below in connection with FIGS. 4-5) at a free rotating joint 29 of the shaft 8 to thereby rotate the end effector 12 and (2) an articulation control 16 to effect rotational articulation of the end effector 12 about the articulation pivot 14. In the illustrated embodiment, the end effector 12 is configured to act as an endocutter for clamping, severing and stapling tissue, although in other embodiments, different types of end effectors may be used, such as end effectors for other types of surgical instruments, such as graspers, cutters, staplers, clip appliers, access devices, drug/gene therapy devices, ultrasound, RF or laser devices, etc.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by the preferably elongate shaft 8. In one embodiment, a clinician or operator of the instrument 10 may articulate the end effector 12 relative to the shaft 8 by utilizing the articulation control 16, as described in more detail in pending U.S. patent application Ser. No. 11/329,020, filed Jan. 10, 2006, entitled "Surgical Instrument Having An Articulating End Effector," by Geoffrey C. Hueil et al., which is incorporated herein by reference.

The end effector 12 includes in this example, among other things, a staple channel 22 and a pivotally translatable clamping member, such as an anvil 24, which are maintained at a spacing that assures effective stapling and severing of tissue clamped in the end effector 12. The handle 6 includes a pistol grip 26 towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position, the firing trigger 20 may rotate slightly toward the pistol grip 26 so that it can be reached by the operator using one hand. Then the operator may pivotally draw the firing trigger 20 toward the pistol grip 12 to cause the stapling and severing of clamped tissue in the end effector 12. The '573 application describes various configurations for locking and unlocking the closure trigger 18. In other embodiments, different types of clamping members besides the anvil 24 could be used, such as, for example, an opposing jaw, etc.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure. A release button 30 on the handle 6, and in this example, on the pistol grip 26 of the handle, when depressed may release the locked closure trigger 18.

Figure 3:
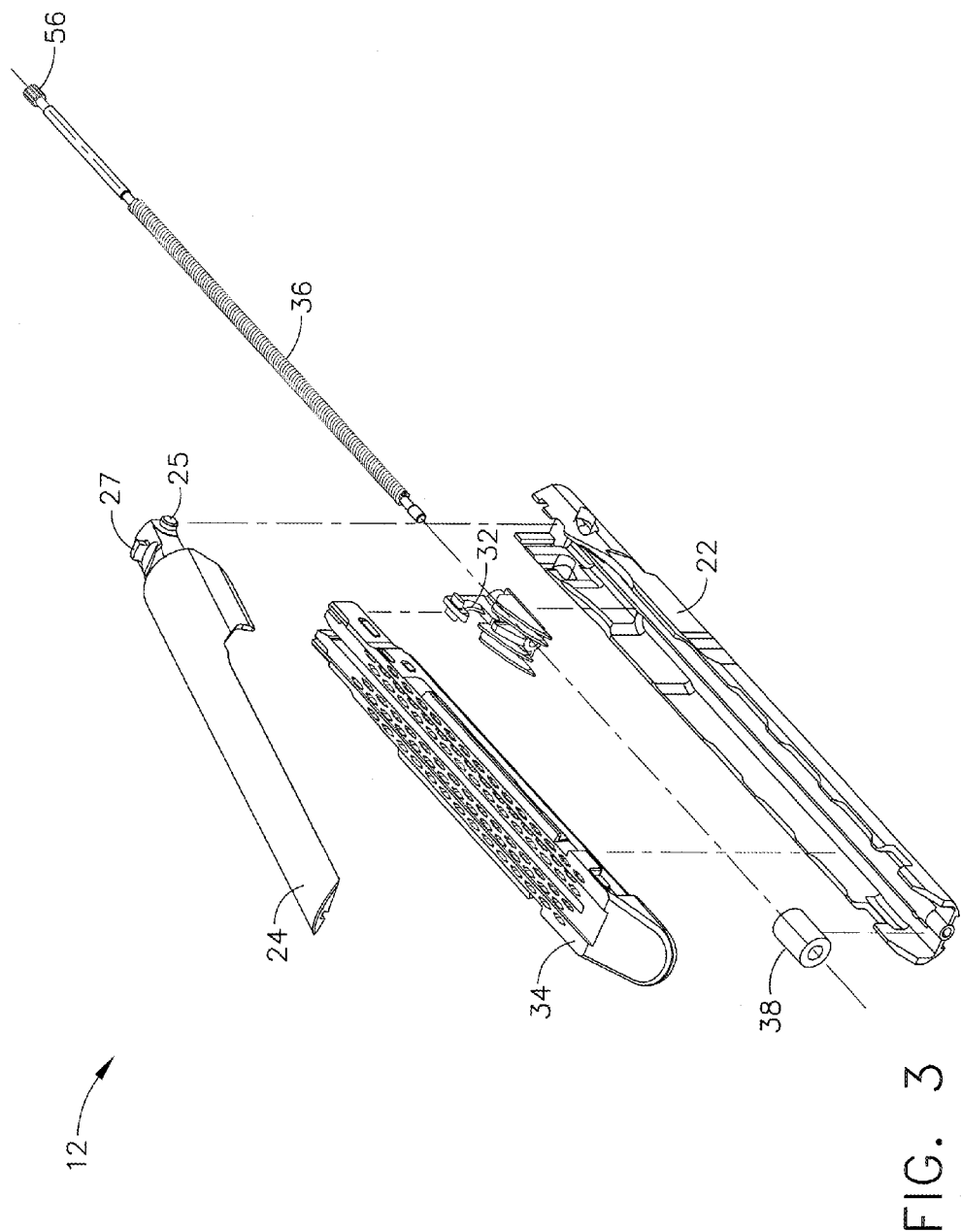
FIGS. 3-5 are exploded views of an end effector and shaft of the instrument according to various embodiments of the present invention.

FIG. 3 is an exploded view of the end effector 12 according to various embodiments. As shown in the illustrated embodiment, the end effector 12 may include, in addition to the previously-mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at a pivot point 25 connected to the proximate end of the channel 22. The anvil 24 may also include a tab 27 at its proximate end that is inserted into a component of the mechanical closure system (described further below) to open and close the anvil 24. When the closure trigger 18 is actuated, that is, drawn in by a user of the instrument 10, the anvil 24 may pivot about the pivot point 25 into the clamped or closed position. If clamping of the end effector 12 is satisfactory, the operator may actuate the firing trigger 20, which, as explained in more detail below, causes the knife 32 and sled 33 to travel longitudinally along the channel 22, thereby cutting tissue clamped within the end effector 12. The movement of the sled 33 along the channel 22 causes the staples of the staple cartridge 34 to be driven through the severed tissue and against the closed anvil 24, which turns the staples to fasten the severed tissue. U.S. Pat. No. 6,978,921, entitled "Surgical stapling instrument incorporating an E-beam firing mechanism," which is incorporated herein by reference, provides more details about such two-stroke cutting and fastening instruments. The sled 33 may be part of the cartridge 34, such that when the knife 32 retracts following the cutting operation, the sled 33 does not retract. The channel 22 and the anvil 24 may be made of an electrically conductive material (such as metal) so that they may serve as part of the antenna that communicates with the sensor(s) in the end effector, as described further below. The cartridge 34 could be made of a nonconductive material (such as plastic) and the sensor may be connected to or disposed in the cartridge 34, as described further below.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,709,680, entitled "Electrosurgical Hemostatic Device" to Yates et al., and U.S. Pat. No. 5,688,270, entitled "Electrosurgical Hemostatic Device With Recessed And/Or Offset Electrodes" to Yates et al., which are incorporated herein by reference, discloses cutting instruments that use RF energy to fasten the severed tissue. U.S. patent application Ser. No. 11/267,811 to Morgan et al. and U.S. patent application Ser. No. 11/267,383 to Shelton et al., which are also incorporated herein by reference, disclose cutting instruments that use adhesives to fasten the severed tissue. Accordingly, although the description herein refers to cutting/stapling operations and the like, it should be recognized that this is an exemplary embodiment and is not meant to be limiting. Other tissue-fastening techniques may also be used.

Figure 4:
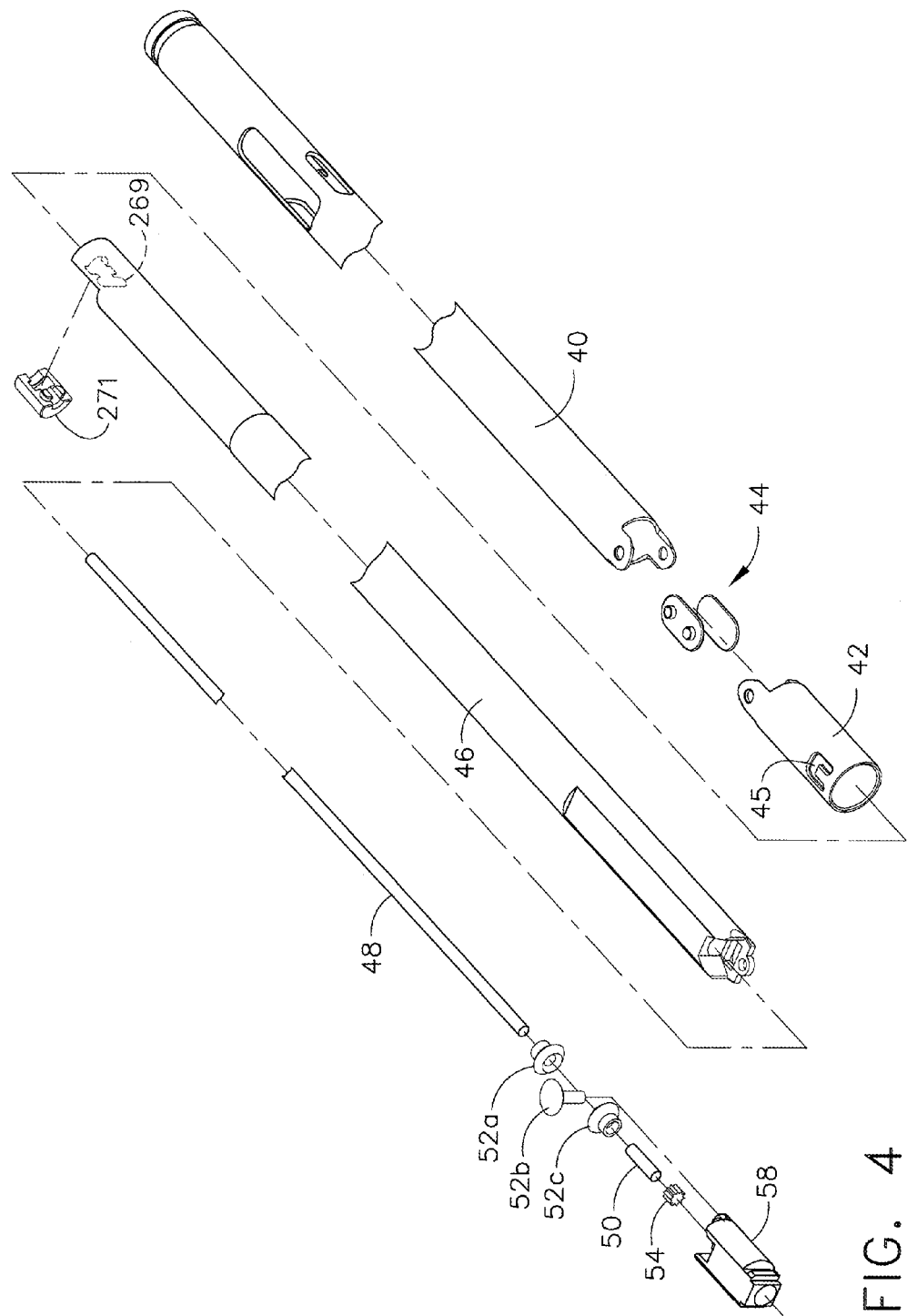
Figure 5:
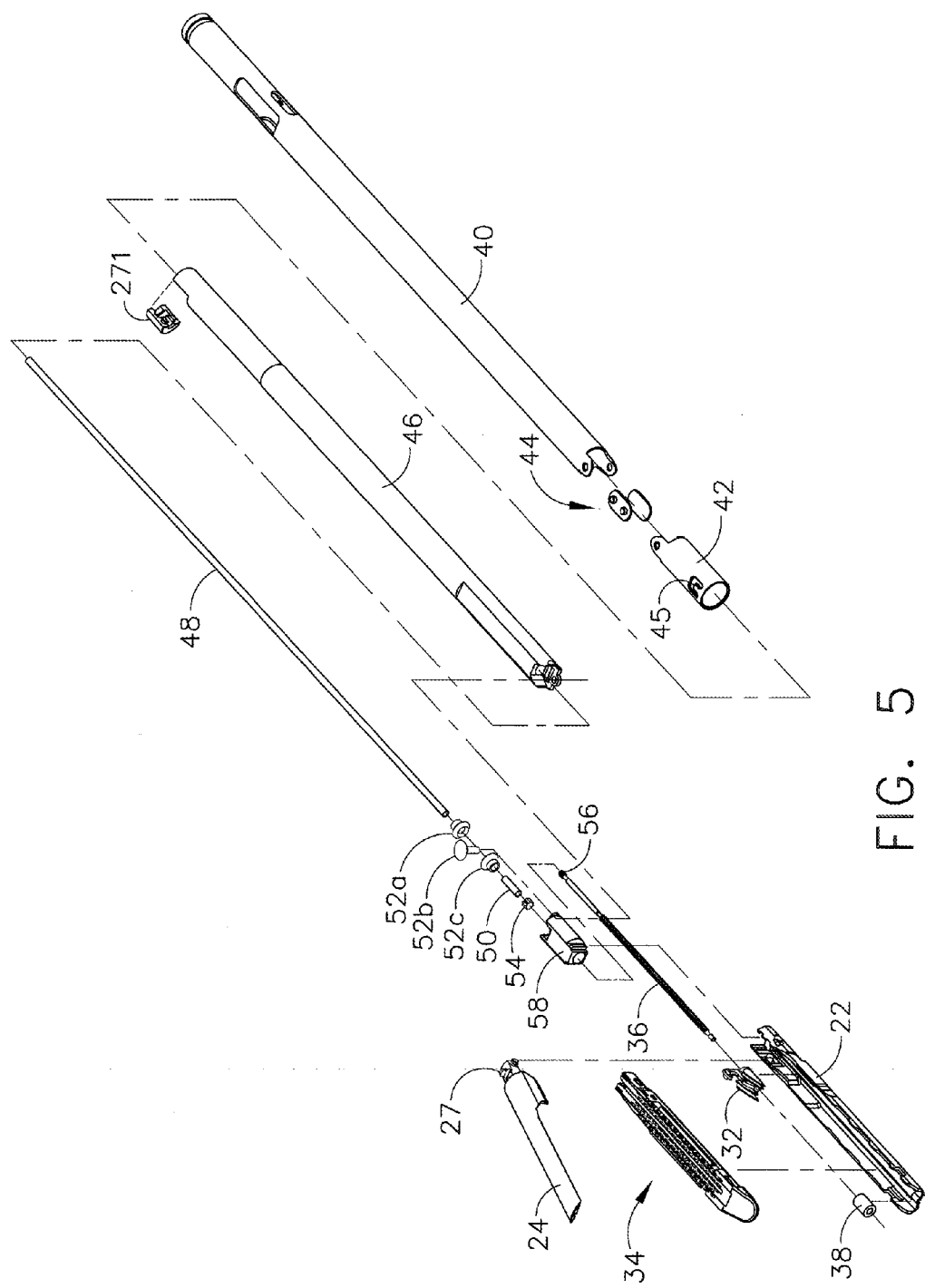
Figure 6:
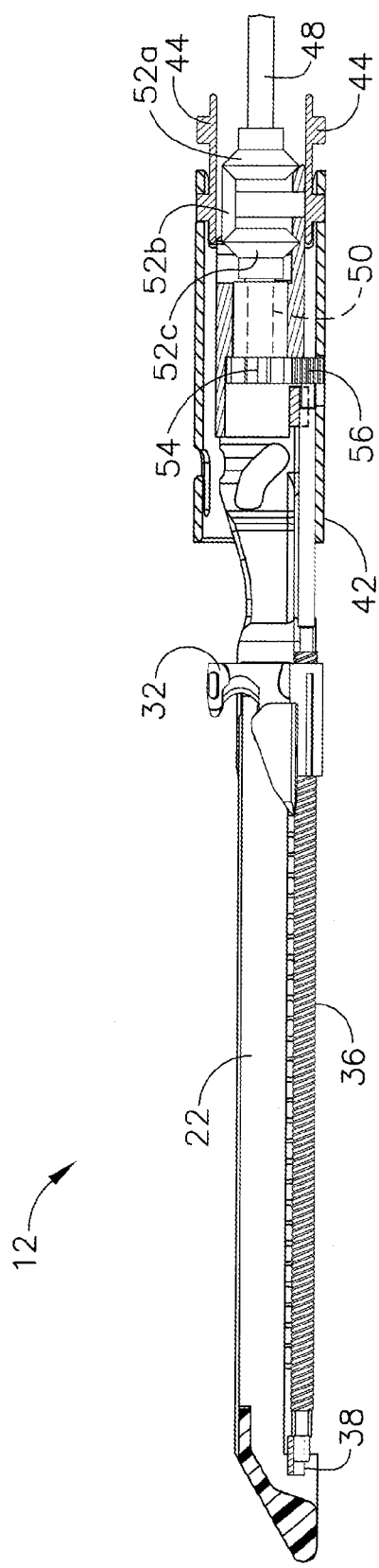
FIG. 6 is a side view of the end effector according to various embodiments of the present invention.
Figure 7:
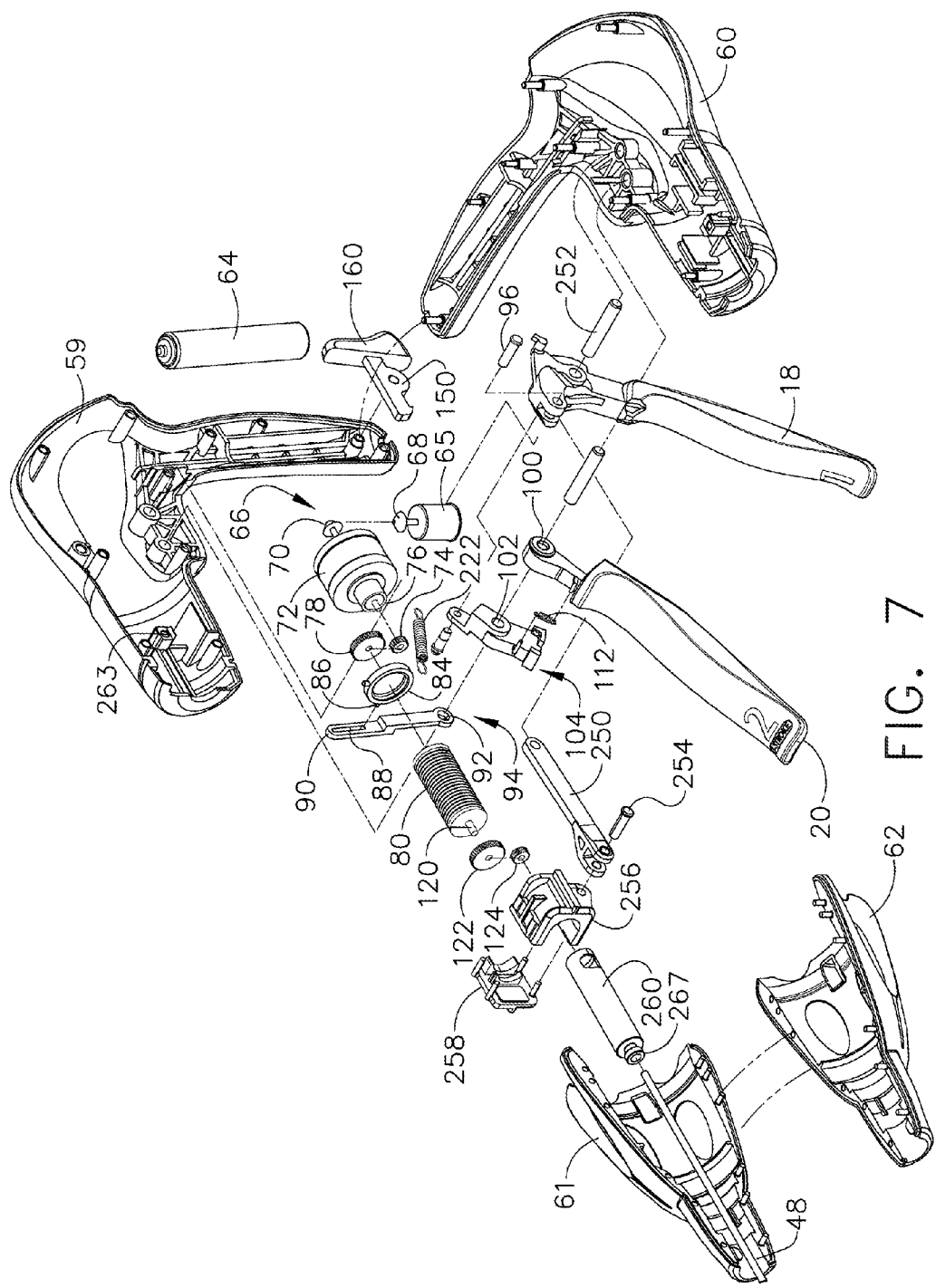
FIG. 7 is an exploded view of the handle of the instrument according to various embodiments of the present invention.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot links 44. The distal closure tube 42 includes an opening 45 into which the tab 27 on the anvil 24 is inserted in order to open and close the anvil 24. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c), are sometimes referred to herein as the "main drive shaft assembly." The closure tubes 40, 42 may be made of electrically conductive material (such as metal) so that they may serve as part of the antenna, as described further below. Components of the main drive shaft assembly (e.g., the drive shafts 48, 50) may be made of a nonconductive material (such as plastic).

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate by actuation of the firing trigger 20 (as explained in more detail below), the bevel gear assembly 52a-c causes the secondary drive shaft 50 to rotate, which in turn, because of the engagement of the drive gears 54, 56, causes the helical screw shaft 36 to rotate, which causes the knife 32 to travel longitudinally along the channel 22 to cut any tissue clamped within the end effector. The sled 33 may be made of, for example, plastic, and may have a sloped distal surface. As the sled 33 traverses the channel 22, the sloped forward surface may push up or drive the staples in the staple cartridge 34 through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

According to various embodiments, as shown FIGS. 7-10, the surgical instrument may include a battery 64 in the handle 6. The illustrated embodiment provides user-feedback regarding the deployment and loading force of the cutting instrument in the end effector 12. In addition, the embodiment may use power provided by the user in retracting the firing trigger 18 to power the instrument 10 (a so-called "power assist" mode). As shown in the illustrated embodiment, the handle 6 includes exterior lower side pieces 59, 60 and exterior upper side pieces 61, 62 that fit together to form, in general, the exterior of the handle 6. The handle pieces 59-62 may be made of an electrically nonconductive material, such as plastic. A battery 64 may be provided in the pistol grip portion 26 of the handle 6. The battery 64 powers a motor 65 disposed in an upper portion of the pistol grip portion 26 of the handle 6. The battery 64 may be constructed according to any suitable construction or chemistry including, for example, a Li-ion chemistry such as $LiCoO_2$ or $LiNiO_2$, a Nickel Metal Hydride chemistry, etc. According to various embodiments, the motor 65 may be a DC brushed driving motor having a maximum rotation of, approximately, 5000 RPM to 100,000 RPM. The motor 64 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72 and ring gear 78.

The handle 6 may also include a run motor sensor 110 in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat or variable resistor. When the firing trigger 20 is drawn in, the sensor 110 detects the movement, and sends an electrical signal indicative of the voltage (or power) to be supplied to the motor 65. When the sensor 110 is a variable resistor or the like, the rotation of the motor 65 may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation. In another embodiment, for example, the control unit (described further below) may output a PWM control signal to the motor 65 based on the input from the sensor 110 in order to control the motor 65.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby remove force from the sensor 100, to thereby stop the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 at its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130, when activated, sends a signal to the control unit which sends a signal to the motor 65 to reverse its rotation direction, thereby withdrawing the knife 32 of the end effector 12 following the cutting operation.

The stop motor sensor 142 may be, for example, a normally-closed limit switch. In various embodiments, it may be located at the proximate end of the helical gear drum 80 so that the ring 84 trips the switch 142 when the ring 84 reaches the proximate end of the helical gear drum 80.

In operation, when an operator of the instrument 10 pulls back the firing trigger 20, the sensor 110 detects the deployment of the firing trigger 20 and sends a signal to the control unit which sends a signal to the motor 65 to cause forward rotation of the motor 65 at, for example, a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to traverse the channel 22 longitudinally, thereby cutting tissue clamped in the end effector 12. Also, the stapling operation of the end effector 12 is caused to happen in embodiments where a stapling-type end effector is used.

By the time the cutting/stapling operation of the end effector 12 is complete, the ring 84 on the helical gear drum 80 will have reached the distal end of the helical gear drum 80, thereby causing the reverse motor sensor 130 to be tripped, which sends a signal to the control unit which sends a signal to the motor 65 to cause the motor 65 to reverse its rotation. This in turn causes the knife 32 to retract, and also causes the ring 84 on the helical gear drum 80 to move back to the proximate end of the helical gear drum 80.

Figure 8:
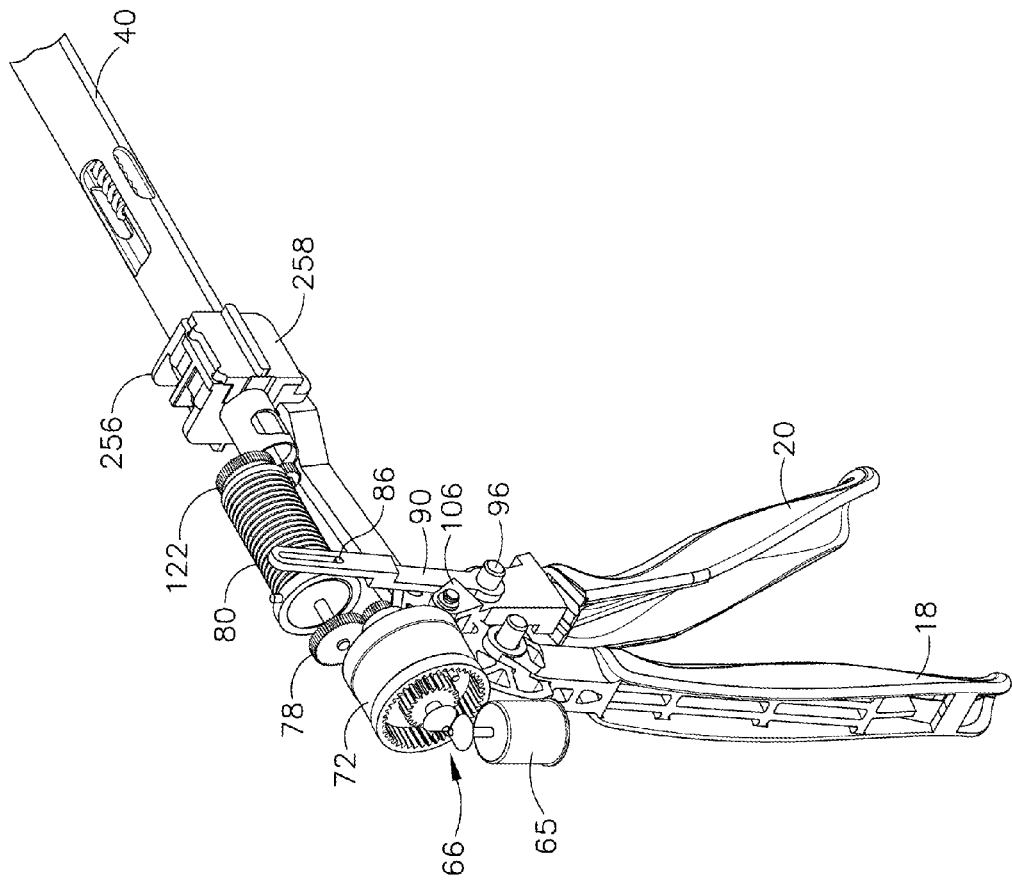
FIGS. 8 and 9 are partial perspective views of the handle according to various embodiments of the present invention.
Figure 9:
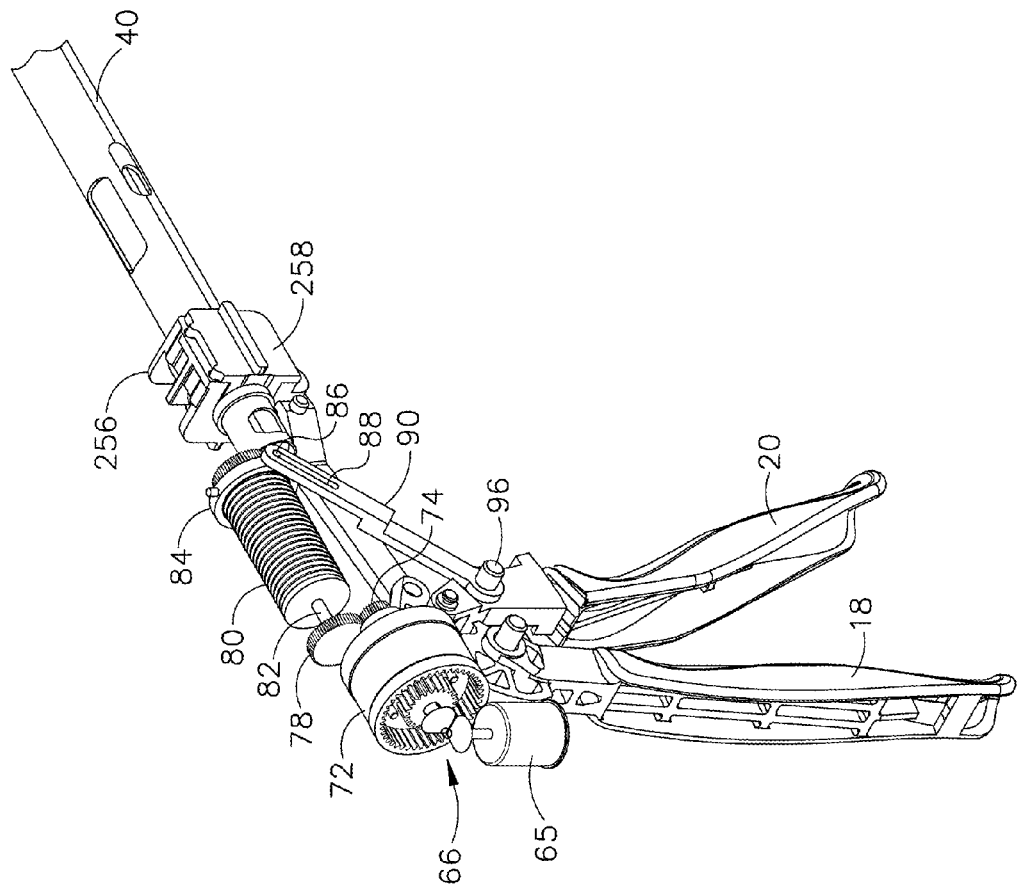
Figure 10:
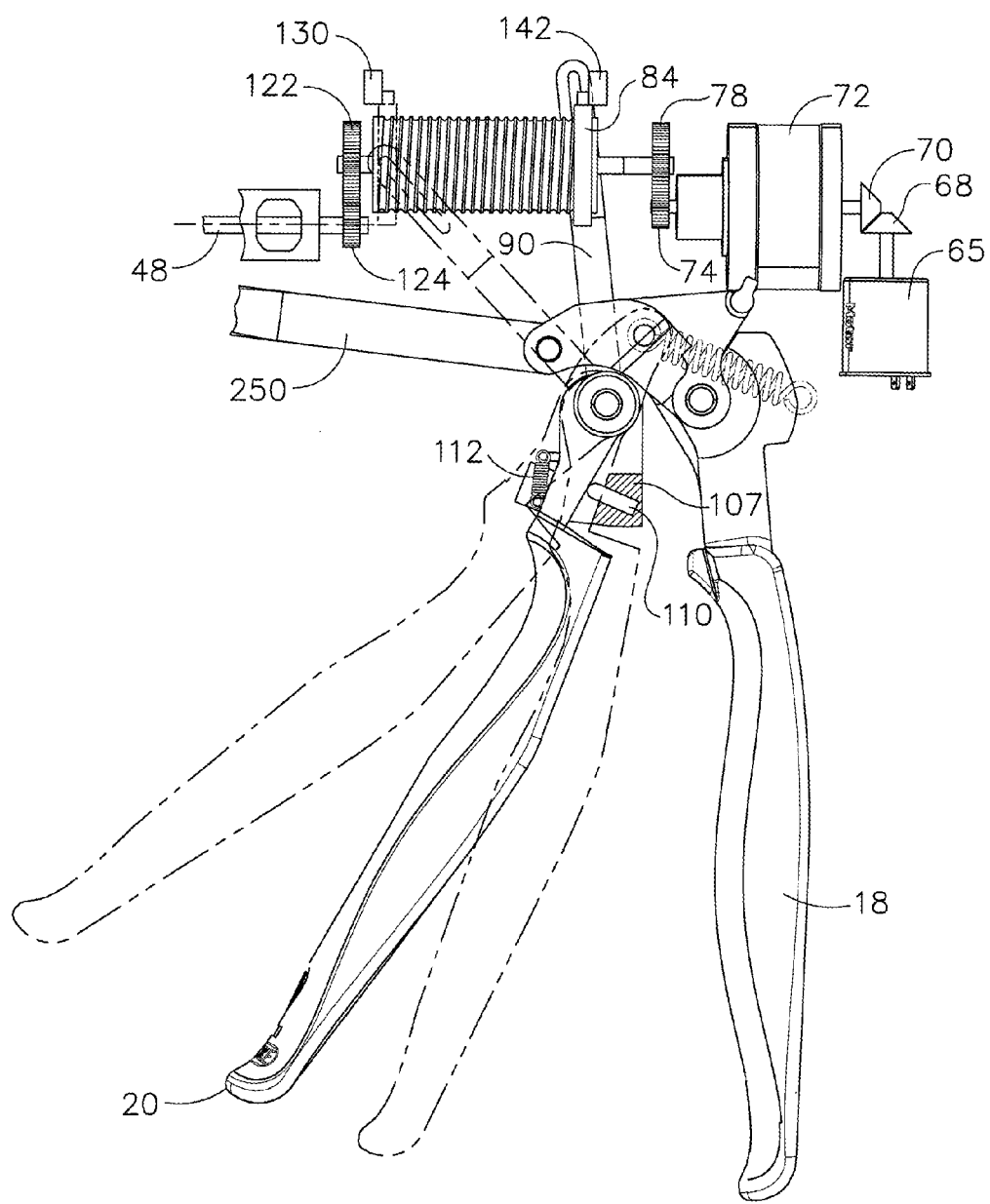
FIG. 10 is a side view of the handle according to various embodiments of the present invention.

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates CCW as the ring 84 travels from the proximate end of the helical gear drum 80 to the distal end, the middle handle piece 104 will be free to rotate CCW. Thus, as the user draws in the firing trigger 20, the firing trigger 20 will engage the forward motion stop 107 of the middle handle piece 104, causing the middle handle piece 104 to rotate CCW. Due to the backside shoulder 106 engaging the slotted arm 90, however, the middle handle piece 104 will only be able to rotate CCW as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate CCW due to the slotted arm 90.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pin 251 that is inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate CCW. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot point 25 into the clamped or closed position. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot about the pivot point 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 18 from the locked position.

The control unit (described further below) may receive the outputs from end-of-stroke and beginning-of-stroke sensors 130, 142 and the run-motor sensor 110, and may control the motor 65 based on the inputs. For example, when an operator initially pulls the firing trigger 20 after locking the closure trigger 18, the run-motor sensor 110 is actuated. If the staple cartridge 34 is present in the end effector 12, a cartridge lockout sensor (not shown) may be closed, in which case the control unit may output a control signal to the motor 65 to cause the motor 65 to rotate in the forward direction. When the end effector 12 reaches the end of its stroke, the reverse motor sensor 130 will be activated. The control unit may receive this output from the reverse motor sensor 130 and cause the motor 65 to reverse its rotational direction. When the knife 32 is fully retracted, the stop motor sensor switch 142 is activated, causing the control unit to stop the motor 65.

In other embodiments, rather than a proportional-type sensor 110, an on-off type sensor could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

Figure 11:
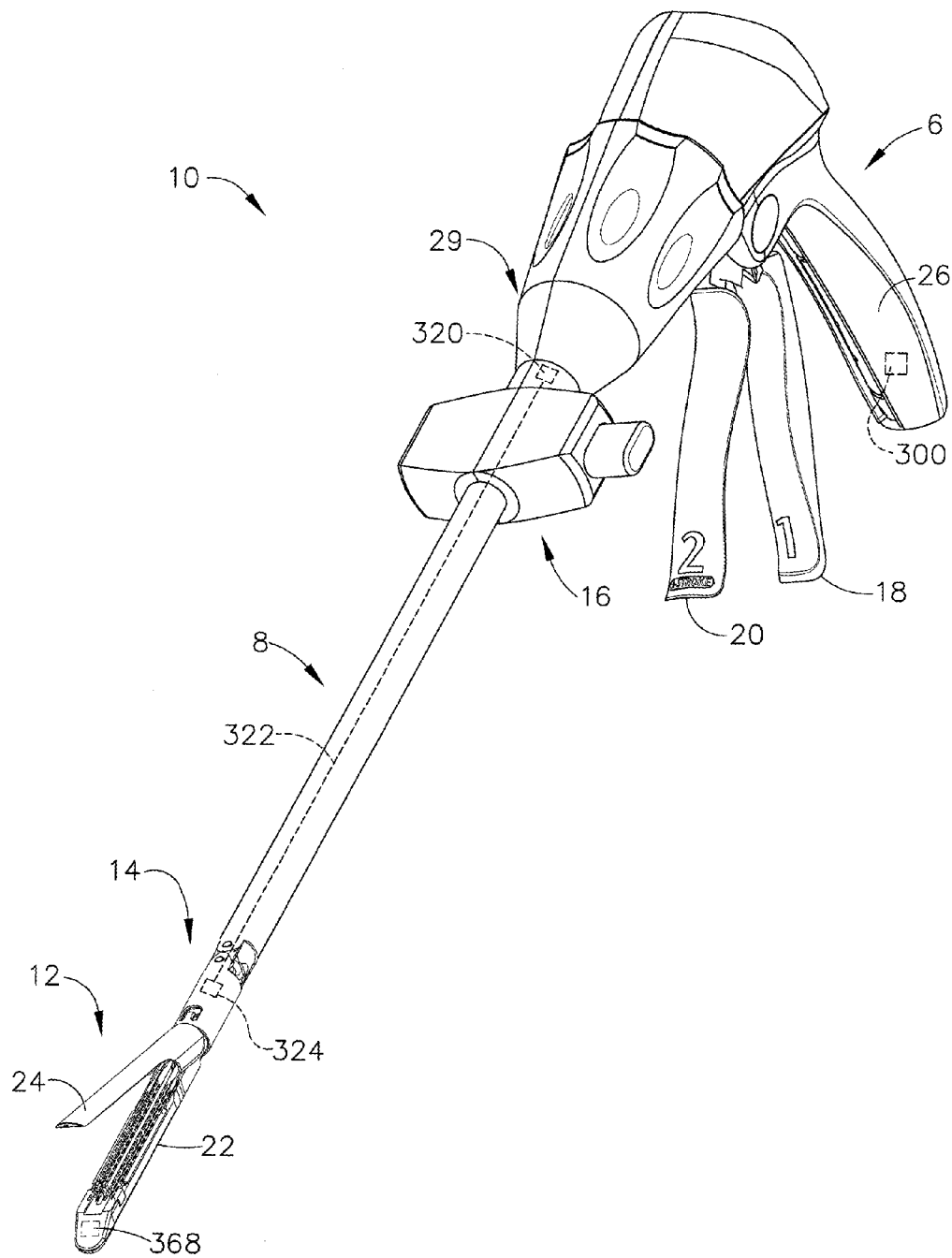

The instrument 10 may include a number of sensor transponders in the end effector 12 for sensing various conditions related to the end effector 12, such as sensor transponders for determining the status of the staple cartridge 34 (or other type of cartridge depending on the type of surgical instrument), the progress of the stapler during closure and firing, etc. The sensor transponders may be passively powered by inductive signals, as described further below, although in other embodiments the transponders could be powered by a remote power source, such as a battery in the end effector 12, for example. The sensor transponder(s) could include magnetoresistive, optical, electromechanical, RFID, MEMS, motion or pressure sensors, for example. These sensor transponders may be in communication with a control unit 300, which may be housed in the handle 6 of the instrument 10, for example, as shown in FIG. 11.

As shown in FIG. 12, according to various embodiments the control unit 300 may comprise a processor 306 and one or more memory units 308. By executing instruction code stored in the memory 308, the processor 306 may control various components of the instrument 10, such as the motor 65 or a user display (not shown), based on inputs received from the various end effector sensor transponders and other sensor(s) (such as the run-motor sensor 110, the end-of-stroke sensor 130, and the beginning-of-stroke sensor 142, for example). The control unit 300 may be powered by the battery 64 during surgical use of instrument 10. The control unit 300 may comprise an inductive element 302 (e.g., a coil or antenna) to pick up wireless signals from the sensor transponders, as described in more detail below. Input signals received by the inductive element 302 acting as a receiving antenna may be demodulated by a demodulator 310 and decoded by a decoder 312. The input signals may comprise data from the sensor transponders in the end effector 12, which the processor 306 may use to control various aspects of the instrument 10.

To transmit signals to the sensor transponders, the control unit 300 may comprise an encoder 316 for encoding the signals and a modulator 318 for modulating the signals according to the modulation scheme. The inductive element 302 may act as the transmitting antenna. The control unit 300 may communicate with the sensor transponders using any suitable wireless communication protocol and any suitable frequency (e.g., an ISM band). Also, the control unit 300 may transmit signals at a different frequency range than the frequency range of the received signals from the sensor transponders. Also, although only one antenna (inductive element 302) is shown in FIG. 12, in other embodiments the control unit 300 may have separate receiving and transmitting antennas.

According to various embodiments, the control unit 300 may comprise a microcontroller, a microprocessor, a field programmable gate array (FPGA), one or more other types of integrated circuits (e.g., RF receivers and PWM controllers), and/or discrete passive components. The control units may also be embodied as system-on-chip (SoC) or a system-in-package (SIP), for example.

As shown in FIG. 11, the control unit 300 may be housed in the handle 6 of the instrument 10 and one or more of the sensor transponders 368 for the instrument 10 may be located in the end effector 12. To deliver power and/or transmit data to or from the sensor transponders 368 in the end effector 12, the inductive element 302 of the control unit 300 may be inductively coupled to a secondary inductive element (e.g., a coil) 320 positioned in the shaft 8 distally from the rotation joint 29. The secondary inductive element 320 is preferably electrically insulated from the conductive shaft 8.

The secondary inductive element 320 may be connected by an electrically conductive, insulated wire 322 to a distal inductive element (e.g., a coil) 324 located near the end effector 12, and preferably distally relative to the articulation pivot 14. The wire 322 may be made of an electrically conductive polymer and/or metal (e.g., copper) and may be sufficiently flexible so that it could pass though the articulation pivot 14 and not be damaged by articulation. The distal inductive element 324 may be inductively coupled to the sensor transponder 368 in, for example, the cartridge 34 of the end effector 12. The transponder 368, as described in more detail below, may include an antenna (or coil) for inductive coupling to the distal coil 324, a sensor and integrated control electronics for receiving and transmitting wireless communication signals.

The transponder 368 may use a portion of the power of the inductive signal received from the distal inductive element 326 to passively power the transponder 368. Once sufficiently powered by the inductive signals, the transponder 368 may receive and transmit data to the control unit 300 in the handle 6 via (i) the inductive coupling between the transponder 368 and the distal inductive element 324, (ii) the wire 322, and (iii) the inductive coupling between the secondary inductive element 320 and the control unit 300. That way, the control unit 300 may communicate with the transponder 368 in the end effector 12 without a direct wired connection through complex mechanical joints like the rotating joint 29 and/or without a direct wired connection from the shaft 8 to the end effector 12, places where it may be difficult to maintain such a wired connection. In addition, because the distances between the inductive elements (e.g., the spacing between (i) the transponder 368 and the distal inductive element 324, and (ii) the secondary inductive element 320 and the control unit 300) and fixed and known, the couplings could be optimized for inductive transfer of energy. Also, the distances could be relatively short so that relatively low power signals could be used to thereby minimize interference with other systems in the use environment of the instrument 10.

Figure 13:
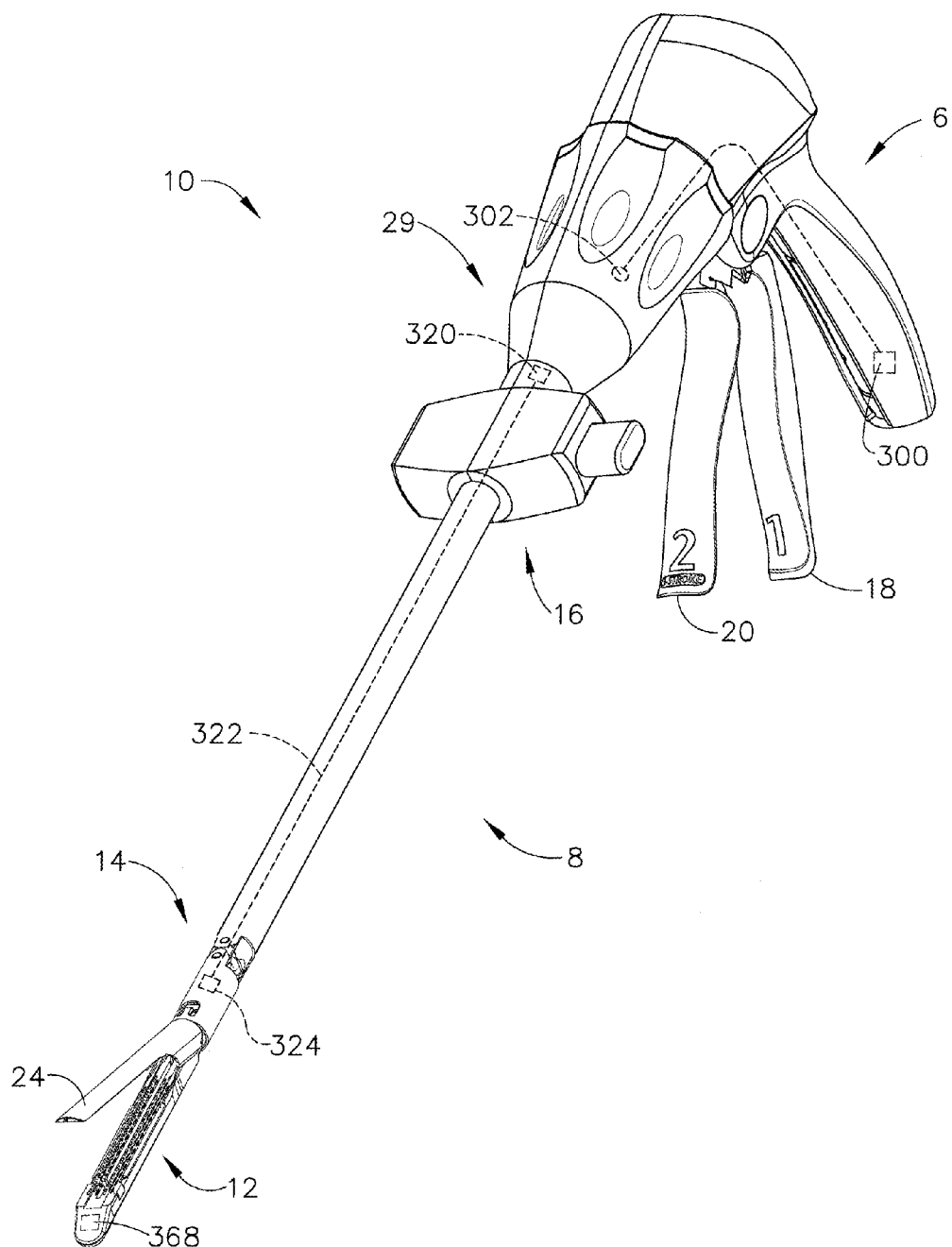

In the embodiment of FIG. 12, the inductive element 302 of the control unit 300 is located relatively near to the control unit 300. According to other embodiments, as shown in FIG. 13, the inductive element 302 of the control unit 300 may be positioned closer to the rotating joint 29 to that it is closer to the secondary inductive element 320, thereby reducing the distance of the inductive coupling in such an embodiment. Alternatively, the control unit 300 (and hence the inductive element 302) could be positioned closer to the secondary inductive element 320 to reduce the spacing.

Figure 14:
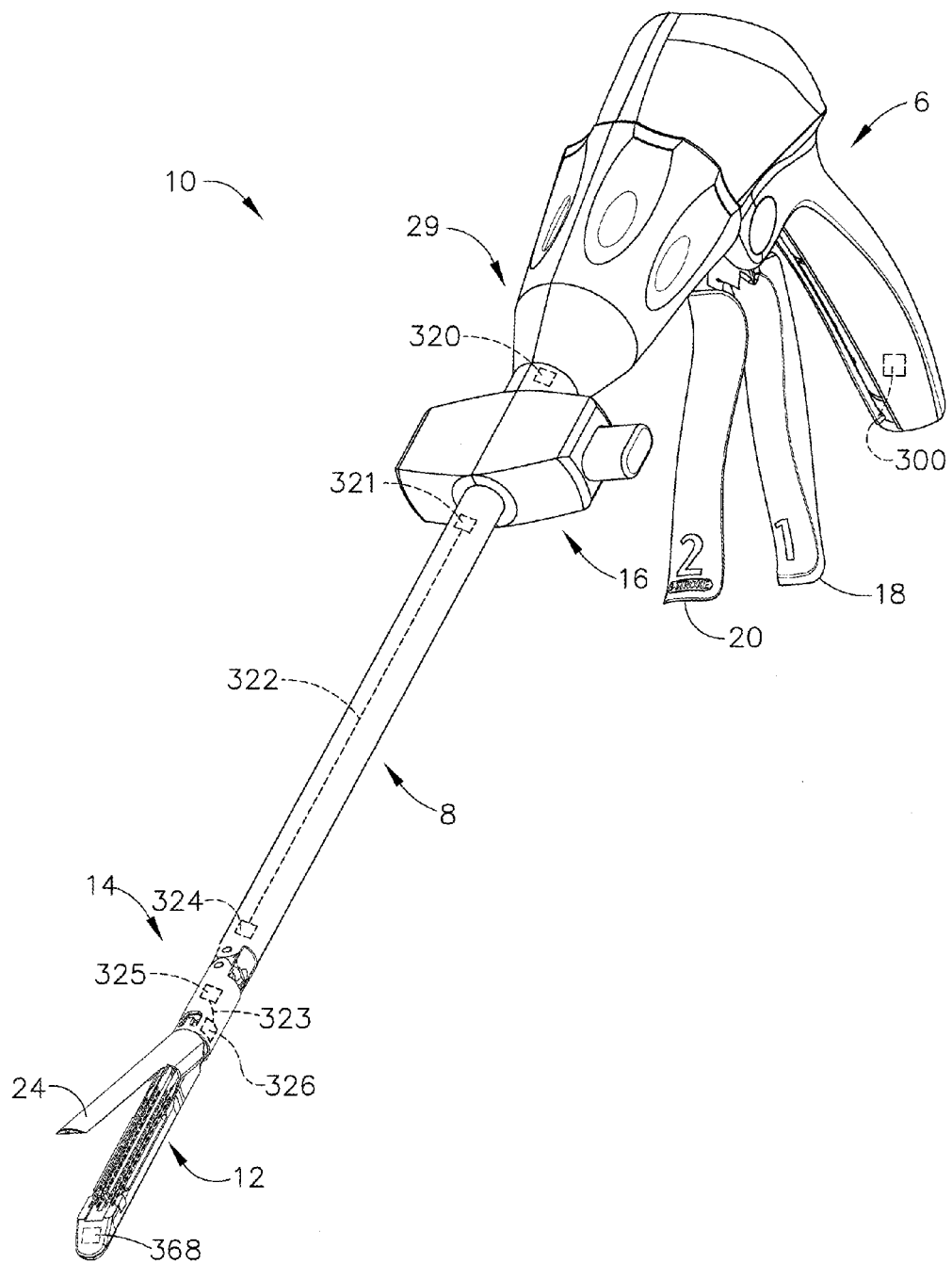

In other embodiments, more or fewer than two inductive couplings may be used. For example, in some embodiments, the surgical instrument 10 may use a single inductive coupling between the control unit 300 in the handle 6 and the transponder 368 in the end effector 12, thereby eliminating the inductive elements 320, 324 and the wire 322. Of course, in such an embodiment, a stronger signal may be required due to the greater distance between the control unit 300 in the handle 6 and the transponder 368 in the end effector 12. Also, more than two inductive couplings could be used. For example, if the surgical instrument 10 had numerous complex mechanical joints where it would be difficult to maintain a direct wired connection, inductive couplings could be used to span each such joint. For example, inductive couplers could be used on both sides of the rotary joint 29 and both sides of the articulation pivot 14, with the inductive element 321 on the distal side of the rotary joint 29 connected by a wire 322 to the inductive element 324 of the proximate side of the articulation pivot, and a wire 323 connecting the inductive elements 325, 326 on the distal side of the articulation pivot 14 as shown in FIG. 14. In this embodiment, the inductive element 326 may communicate with the sensor transponder 368.

In addition, the transponder 368 may include a number of different sensors. For example, it may include an array of sensors. Further, the end effector 12 could include a number of sensor transponders 368 in communication with the distal inductive element 324 (and hence the control unit 300). Also, the inductive elements 320, 324 may or may not include ferrite cores. As mentioned before, they are also preferably insulated from the electrically conductive outer shaft (or frame) of the instrument 10 (e.g., the closure tubes 40, 42), and the wire 322 is also preferably insulated from the outer shaft 8.

FIG. 15 is a diagram of an end effector 12 including a transponder 368 held or embedded in the cartridge 34 at the distal end of the channel 22. The transponder 368 may be connected to the cartridge 34 by a suitable bonding material, such as epoxy. In this embodiment, the transponder 368 includes a magnetoresistive sensor. The anvil 24 also includes a permanent magnet 369 at its distal end and generally facing the transponder 368. The end effector 12 also includes a permanent magnet 370 connected to the sled 33 in this example embodiment. This allows the transponder 368 to detect both opening/closing of the end effector 12 (due to the permanent magnet 369 moving further or closer to the transponder as the anvil 24 opens and closes) and completion of the stapling/cutting operation (due to the permanent magnet 370 moving toward the transponder 368 as the sled 33 traverses the channel 22 as part of the cutting operation).

FIG. 15 also shows the staples 380 and the staple drivers 382 of the staple cartridge 34. As explained previously, according to various embodiments, when the sled 33 traverses the channel 22, the sled 33 drives the staple drivers 382 which drive the staples 380 into the severed tissue held in the end effector 12, the staples 380 being formed against the anvil 24. As noted above, such a surgical cutting and fastening instrument is but one type of surgical instrument in which the present invention may be advantageously employed. Various embodiments of the present invention may be used in any type of surgical instrument having one or more sensor transponders.

In the embodiments described above, the battery 64 powers (at least partially) the firing operation of the instrument 10. As such, the instrument may be a so-called "power-assist" device. More details and additional embodiments of power-assist devices are described in the '573 application, which is incorporated herein. It should be recognized, however, that the instrument 10 need not be a power-assist device and that this is merely an example of a type of device that may utilize aspects of the present invention. For example, the instrument 10 may include a user display (such as a LCD or LED display) that is powered by the battery 64 and controlled by the control unit 300. Data from the sensor transponders 368 in the end effector 12 may be displayed on such a display.

In another embodiment, the shaft 8 of the instrument 10, including for example, the proximate closure tube 40 and the distal closure tube 42, may collectively serve as part of an antenna for the control unit 300 by radiating signals to the sensor transponder 368 and receiving radiated signals from the sensor transponder 368. That way, signals to and from the remote sensor in the end effector 12 may be transmitted via the shaft 8 of the instrument 10.

The proximate closure tube 40 may be grounded at its proximate end by the exterior lower and upper side pieces 59-62, which may be made of a nonelectrically conductive material, such as plastic. The drive shaft assembly components (including the main drive shaft 48 and secondary drive shaft 50) inside the proximate and distal closure tubes 40, 42 may also be made of a nonelectrically conductive material, such as plastic. Further, components of end effector 12 (such as the anvil 24 and the channel 22) may be electrically coupled to (or in direct or indirect electrical contact with) the distal closure tube 42 such that they may also serve as part of the antenna. Further, the sensor transponder 368 could be positioned such that it is electrically insulated from the components of the shaft 8 and end effector 12 serving as the antenna. For example, the sensor transponder 368 may be positioned in the cartridge 34, which may be made of a nonelectrically conductive material, such as plastic. Because the distal end of the shaft 8 (such as the distal end of the distal closure tube 42) and the portions of the end effector 12 serving as the antenna may be relatively close in distance to the sensor 368, the power for the transmitted signals may be held at low levels, thereby minimizing or reducing interference with other systems in the use environment of the instrument 10.

Figure 16:
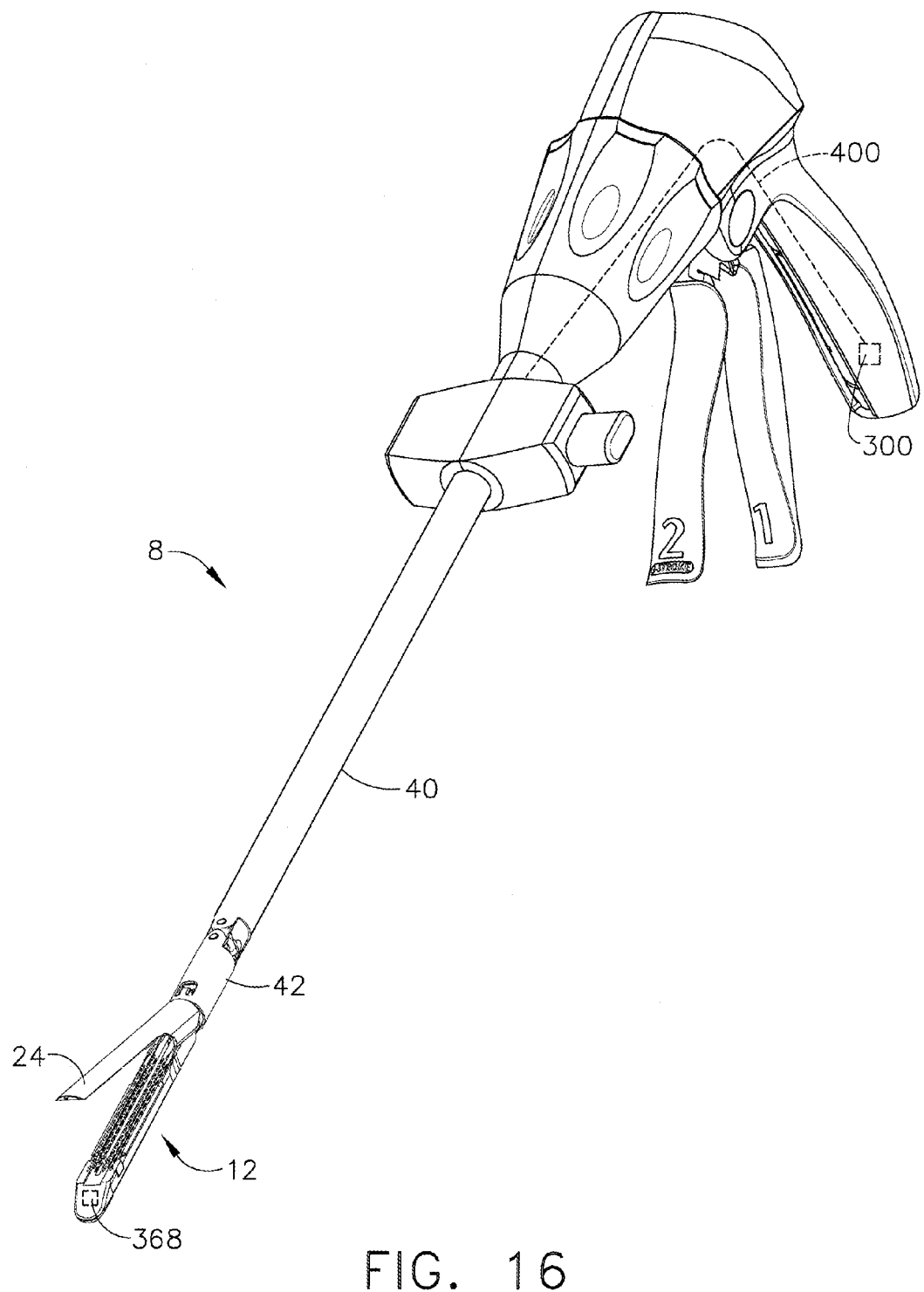

In such an embodiment, as shown in FIG. 16, the control unit 300 may be electrically coupled to the shaft 8 of the instrument 10, such as to the proximate closure tube 40, by a conductive link 400 (e.g., a wire). Portions of the outer shaft 8, such as the closure tubes 40, 42, may therefore act as part of an antenna for the control unit 300 by radiating signals to the sensor 368 and receiving radiated signals from the sensor 368. Input signals received by the control unit 300 may be demodulated by the demodulator 310 and decoded by the decoder 312 (see FIG. 12). The input signals may comprise data from the sensors 368 in the end effector 12, which the processor 306 may use to control various aspects of the instrument 10, such as the motor 65 or a user display.

To transmit data signals to or from the sensors 368 in the end effector 12, the link 400 may connect the control unit 300 to components of the shaft 8 of the instrument 10, such as the proximate closure tube 40, which may be electrically connected to the distal closure tube 42. The distal closure tube 42 is preferably electrically insulated from the remote sensor 368, which may be positioned in the plastic cartridge 34 (see FIG. 3). As mentioned before, components of the end effector 12, such as the channel 22 and the anvil 24 (see FIG. 3), may be conductive and in electrical contact with the distal closure tube 42 such that they, too, may serve as part of the antenna.

With the shaft 8 acting as the antenna for the control unit 300, the control unit 300 can communicate with the sensor 368 in the end effector 12 without a direct wired connection. In addition, because the distances between shaft 8 and the remote sensor 368 is fixed and known, the power levels could be optimized for low levels to thereby minimize interference with other systems in the use environment of the instrument 10. The sensor 368 may include communication circuitry for radiating signals to the control unit 300 and for receiving signals from the control unit 300, as described above. The communication circuitry may be integrated with the sensor 368.

In another embodiment, the components of the shaft 8 and/or the end effector 12 may serve as an antenna for the remote sensor 368. In such an embodiment, the remote sensor 368 is electrically connected to the shaft (such as to distal closure tube 42, which may be electrically connected to the proximate closure tube 40) and the control unit 300 is insulated from the shaft 8. For example, the sensor 368 could be connected to a conductive component of the end effector 12 (such as the channel 22), which in turn may be connected to conductive components of the shaft (e.g., the closure tubes 40, 42). Alternatively, the end effector 12 may include a wire (not shown) that connects the remote sensor 368 the distal closure tube 42.

Typically, surgical instruments, such as the instrument 10, are cleaned and sterilized prior to use. In one sterilization technique, the instrument 10 is placed in a closed and sealed container 280, such as a plastic or TYVEK container or bag, as shown in FIGS. 17 and 18. The container and the instrument are then placed in a field of radiation that can penetrate the container, such as gamma radiation, x-rays, or high-energy electrons. The radiation kills bacteria on the instrument 10 and in the container 280. The sterilized instrument 10 can then be stored in the sterile container 280. The sealed, sterile container 280 keeps the instrument 10 sterile until it is opened in a medical facility or some other use environment. Instead of radiation, other means of sterilizing the instrument 10 may be used, such as ethylene oxide or steam.

When radiation, such as gamma radiation, is used to sterilize the instrument 10, components of the control unit 300, particularly the memory 308 and the processor 306, may be damaged and become unstable. Thus, according to various embodiments of the present invention, the control unit 300 may be programmed after packaging and sterilization of the instrument 10.

As shown in FIG. 17, a remote programming device 320, which may be a handheld device, may be brought into wireless communication with the control unit 300. The remote programming device 320 may emit wireless signals that are received by the control unit 300 to program the control unit 300 and to power the control unit 300 during the programming operation. That way, the battery 64 does not need to power the control unit 300 during the programming operation. According to various embodiments, the programming code downloaded to the control unit 300 could be of relatively small size, such as 1 MB or less, so that a communications protocol with a relatively low data transmission rate could be used if desired. Also, the remote programming unit 320 could be brought into close physical proximity with the surgical instrument 10 so that a low power signal could be used.

Referring back to FIG. 19, the control unit 300 may comprise an inductive coil 402 to pick up wireless signals from a remote programming device 320. A portion of the received signal may be used by a power circuit 404 to power the control unit 300 when it is not being powered by the battery 64.

Input signals received by the coil 402 acting as a receiving antenna may be demodulated by a demodulator 410 and decoded by a decoder 412. The input signals may comprise programming instructions (e.g., code), which may be stored in a non-volatile memory portion of the memory 308. The processor 306 may execute the code when the instrument 10 is in operation. For example, the code may cause the processor 306 to output control signals to various sub-systems of the instrument 10, such as the motor 65, based on data received from the sensors 368.

The control unit 300 may also comprise a non-volatile memory unit 414 that comprises boot sequence code for execution by the processor 306. When the control unit 300 receives enough power from the signals from the remote control unit 320 during the post-sterilization programming operation, the processor 306 may first execute the boot sequence code ("boot loader") 414, which may load the processor 306 with an operating system.

The control unit 300 may also send signals back to the remote programming unit 320, such as acknowledgement and handshake signals, for example. The control unit 300 may comprise an encoder 416 for encoding the signals to then be sent to the programming device 320 and a modulator 418 for modulating the signals according to the modulation scheme. The coil 402 may act as the transmitting antenna. The control unit 300 and the remote programming device 320 may communicate using any suitable wireless communication protocol (e.g., Bluetooth) and any suitable frequency (e.g., an ISM band). Also, the control unit 300 may transmit signals at a different frequency range than the frequency range of the received signals from the remote programming unit 320.

FIG. 20 is a simplified diagram of the remote programming device 320 according to various embodiments of the present invention. As shown in FIG. 20, the remote programming unit 320 may comprise a main control board 230 and a boosted antenna board 232. The main control board 230 may comprise a controller 234, a power module 236, and a memory 238. The memory 238 may stored the operating instructions for the controller 234 as well as the programming instructions to be transmitted to the control unit 300 of the surgical instrument 10. The power module 236 may provide a stable DC voltage for the components of the remote programming device 320 from an internal battery (not shown) or an external AC or DC power source (not shown).

The boosted antenna board 232 may comprise a coupler circuit 240 that is in communication with the controller 234 via an I²C bus, for example. The coupler circuit 240 may communicate with the control unit 300 of the surgical instrument via an antenna 244. The coupler circuit 240 may handle the modulating/demodulating and encoding/decoding operations for transmissions with the control unit. According to other embodiments, the remote programming device 320 could have a discrete modulator, demodulator, encoder and decoder. As shown in FIG. 20, the boost antenna board 232 may also comprise a transmitting power amp 246, a matching circuit 248 for the antenna 244, and a filter/amplifier 249 for receiving signals.

According to other embodiments, as shown in FIG. 20, the remote programming device could be in communication with a computer device 460, such as a PC or a laptop, via a USB and/or RS232 interface, for example. In such a configuration, a memory of the computing device 460 may store the programming instructions to be transmitted to the control unit 300. In another embodiment, the computing device 460 could be configured with a wireless transmission system to transmit the programming instructions to the control unit 300.

In addition, according to other embodiments, rather than using inductive coupling between the control unit 300 and the remote programming device 320, capacitively coupling could be used. In such an embodiment, the control unit 300 could have a plate instead of a coil, as could the remote programming unit 320.

Figure 22:
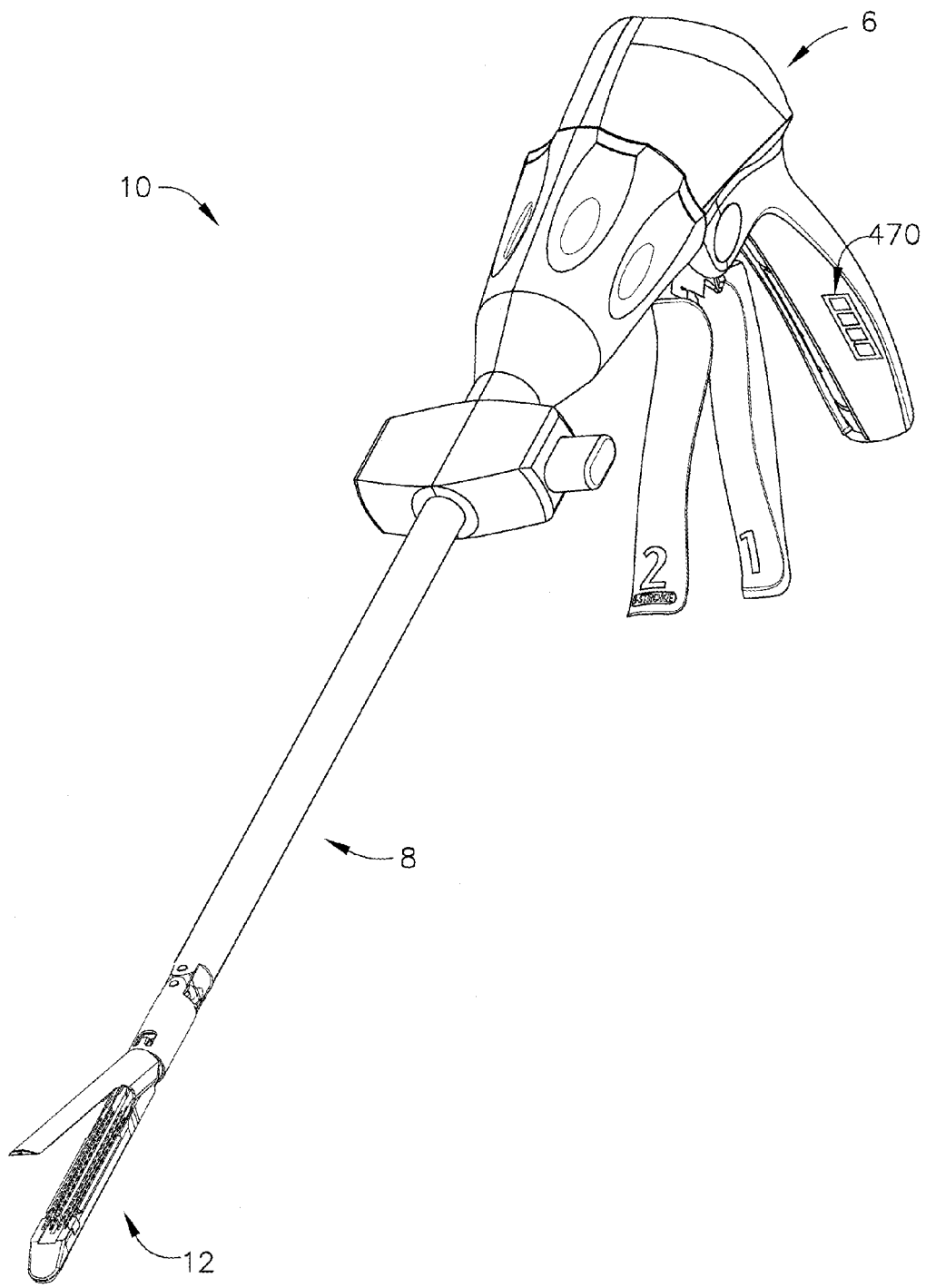

In another embodiment, rather than using a wireless communication link between the control unit 300 and the remote programming device 320, the programming device 320 may be physically connected to the control unit 300 while the instrument 10 is in its sterile container 280 in such a way that the instrument 10 remains sterilized. FIG. 21 is a diagram of a packaged instrument 10 according to such an embodiment. As shown in FIG. 22, the handle 6 of the instrument 10 may include an external connection interface 470. The container 280 may further comprise a connection interface 472 that mates with the external connection interface 470 of the instrument 10 when the instrument 10 is packaged in the container 280. The programming device 320 may include an external connection interface (not shown) that may connect to the connection interface 472 at the exterior of the container 280 to thereby provide a wired connection between the programming device 320 and the external connection interface 470 of the instrument 10.

The various embodiments of the present invention have been described above in connection with cutting-type surgical instruments. It should be noted, however, that in other embodiments, the inventive surgical instrument disclosed herein need not be a cutting-type surgical instrument, but rather could be used in any type of surgical instrument including remote sensor transponders. For example, it could be a non-cutting endoscopic instrument, a grasper, a stapler, a clip applier, an access device, a drug/gene therapy delivery device, an energy device using ultrasound, RF, laser, etc. In addition, the present invention may be in laparoscopic instruments, for example. The present invention also has application in conventional endoscopic and open surgical instrumentation as well as robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although the present invention has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument comprising:
   an end effector comprising at least one sensor;
   a shaft having a distal end connected to the end effector, wherein the shaft comprises:
      at least one electrically conductive outer tube, wherein the sensor is electrically insulated from the at least one electrically conductive outer tube; and
      a drive shaft disposed at least partially within the at least one electrically conductive outer tube;
   a handle connected to a proximate end of the shaft, the handle housing a control unit, wherein the control unit is electrically coupled to the at least one electrically conductive outer tube such that the at least one electrically conductive outer tube wirelessly radiates communication signals from the control unit to the sensor and receives wirelessly radiated communication signals from the sensor.

2. The surgical instrument of claim 1, wherein the handle further houses:
   a motor in communication with the control unit and for powering the end effector; and
   a battery for powering the motor.

3. The surgical instrument of claim 1, wherein the at least one sensor comprises a magnetoresistive sensor.

4. The surgical instrument of claim 1, wherein the at least one sensor comprises a pressure sensor.

5. The surgical instrument of claim 1, wherein the at least one sensor comprises a RFID sensor.

6. The surgical instrument of claim 1, wherein the at least one sensor comprises a MEMS sensor.

7. The surgical instrument of claim 1, wherein the at least one sensor comprises an electromechanical sensor.

8. The surgical instrument of claim 1, wherein the at least one sensor is connected to a plastic cartridge of the end effector.

9. The surgical instrument of claim 1, wherein the end effector comprises an electrically conductive component coupled to the at least one electrically conductive outer tube, wherein the electrically conductive component is configured to radiate communication signals to and from the sensor.

10. The surgical instrument of claim 1, wherein the surgical instrument comprises an endoscopic surgical instrument.

11. The surgical instrument of claim 1, wherein the surgical instrument comprises a cutting and fastening surgical instrument.

12. The surgical instrument of claim 11, wherein the end effector comprises a cutting instrument.

13. The surgical instrument of claim 12, wherein the end effector comprises a plastic cartridge and the at least one sensor is disposed in the cartridge.

14. The surgical instrument of claim 1, wherein the communication signals radiated wirelessly from the shaft use a wireless communication protocol.

15. The surgical instrument of claim 1, wherein the wireless signals comprise RF wireless signals.

16. A surgical instrument comprising:
   an end effector comprising at least one sensor;
   an electrically conductive shaft having a distal end connected to the end effector wherein the shaft comprises at least one electrically conductive outer tube, wherein the sensor is electrically insulated from the at least one electrically conductive outer tube; and
   a control unit electrically coupled to the shaft such that the at least one electrically conductive outer tube wirelessly radiates communication signals from the control unit to the sensor and to receives wirelessly radiated communication signals from the sensor.

17. The surgical instrument of claim 16, further comprising:
   a motor in communication with the control unit and for powering the end effector; and
   a battery for powering the motor.

18. The surgical instrument of claim 16, wherein the at least one sensor is connected to a plastic cartridge of the end effector.

19. The surgical instrument of claim 16, wherein the end effector comprises an electrically conductive component coupled to the at least one electrically conductive outer tube, wherein the electrically conductive component is configured to radiate wireless communication signals to and from the sensor.

20. The surgical instrument of claim 19, wherein the end effector comprises a plastic staple cartridge and the at least one sensor is disposed in the staple cartridge.

21. A surgical instrument comprising:
   an end effector comprising at least one sensor;
   an electrically conductive shaft having a distal end connected to the end effector, wherein the shaft comprises at least one electrically conductive outer tube, wherein the sensor is electrically coupled to the at least one electrically conductive outer tube; and
   a control unit electrically insulated from the at least one electrically conductive outer tube, such that the at least one electrically conductive outer tube radiates wireless communication signals from the sensor to the control unit and receives wirelessly radiated communication signals from the control unit.

* * * * *

UNITED STATES PATENT AND TRADEMARK OFFICE
CERTIFICATE OF CORRECTION

| | | |
|---|---|---|
| PATENT NO. | : 8,459,520 B2 | Page 1 of 1 |
| APPLICATION NO. | : 11/651807 | |
| DATED | : June 11, 2013 | |
| INVENTOR(S) | : James R. Giordano et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1106 days.

Signed and Sealed this
Twenty-third Day of December, 2014

Michelle K. Lee
*Deputy Director of the United States Patent and Trademark Office*